(12) United States Patent
Thilmony et al.

(10) Patent No.: US 8,841,434 B2
(45) Date of Patent: Sep. 23, 2014

(54) ISOLATED RICE LP2 PROMOTERS AND USES THEREOF

(75) Inventors: Roger L Thilmony, El Cerrito, CA (US); Mara E Guttman, Kensington, CA (US); James G Thomson, El Cerrito, CA (US)

(73) Assignee: The United States of America, as represented by the Secretary of Agriculture, Washington, DC (US)

( * ) Notice: Subject to any disclaimer, the term of this patent is extended or adjusted under 35 U.S.C. 154(b) by 776 days.

(21) Appl. No.: 12/890,974

(22) Filed: Sep. 27, 2010

(65) Prior Publication Data

US 2011/0179511 A1 Jul. 21, 2011

Related U.S. Application Data

(60) Provisional application No. 61/247,531, filed on Sep. 30, 2009.

(51) Int. Cl.
*C07H 21/04* (2006.01)
*C12N 15/00* (2006.01)
*C12N 5/10* (2006.01)
*C12N 15/82* (2006.01)

(52) U.S. Cl.
CPC ........ *C12N 15/8239* (2013.01); *C12N 15/8237* (2013.01)
USPC ........ 536/24.1; 435/320.1; 435/419; 800/278

(58) Field of Classification Search
None
See application file for complete search history.

(56) References Cited

U.S. PATENT DOCUMENTS

| 6,455,672 | B1 * | 9/2002 | Benfey et al. | 530/350 |
| 2007/0020621 | A1 * | 1/2007 | Boukharov et al. | 435/6 |
| 2007/0101454 | A1 * | 5/2007 | Jiang et al. | 800/278 |

OTHER PUBLICATIONS

Saha et al., Plant Mol Biol Rep 29:265-77 (2011).*
Wahl_Meth Enzymol_152:399 (1987).*
Hartzell et al., Proc Natl Acad Sci 81:23 (1984).*
Arguello-Astorga, G.R. and L.R. Herrera-Estrella, "Ancestral Multipartite Units in Light-Responsive Plant Promoters Have Structural Features Correlating with Specific Phototransduction Pathways" (1996) Plant Physiology 112:1151-1166.
Cai, M. et al., "A rice promoter containing both novel positive and negative cis-elements for regulation of green tissue-specific gene expression in transgenic plants" (2007) Plant Biotechnology 5:664-674.
Conley, T.R. et al., "Characterization of cis-acting elements in light regulation of the nuclear gene encoding the A subunit of chloroplast isozymes of glyceraldehyde-3-phosphate dehydrogenase from *Arabidopsis thaliana*" (1994) Molecular and Cellular Biology 14(4):2525-2533.
Dardick, C. and P. Ronald, "Plant and Animal Pathogen Recognition Receptors Signal through Non-RD Kinases" (2006) PLoS Pathogens 2(1):14-28.
Ding, X. et al., "A Rice Kinase-Protein Interaction Map" (2009) Plant Physiology 149:1478-1492.
Kikuchi, S. et al., "Collection, Mapping, and Annotation of Over 28,000 cDNA Clones from japonica Rice" (2003) Science 301:376-379.
Kim, D. et al., Gene Transcription in the Leaves of Rice Undergoing Salt-induced Morphological Changes (*Oryza sativa* L) (2007) Molecules and Cells 24(1):45-59.
Kuhlemeier, C. et al., "Localization and conditional redundancy of regulatory elements in rbcS-3A, a pea gene encoding the small subunit of ribulose-bisphosphate carboxylase" (1988) Proceedings of the National Academy of Sciences, USA 85:4662-4666.
Lam, E. and Chua, N., "ASF-2: A Factor That Binds to the Cauliflower Mosaic Virus 35S Promoter and a Conserved GATA Motif in Cab Promoters" (1989) The Plant Cell 1:1147-1156.
Lee, S. et al., "Localizome: a server for identifying transmembrane topologies and TM helices of eukaryotic proteins utilizing domain information" (2006) Nucleic Acids Research 34:W99-W103.
McNally, K.L. et al., "Sequencing Multiple and Diverse Rice Varieties. Connecting Whole-Genome Variation with Phenotypes" (2006) Plant Physiology 141:26-31.
Ono, A. et al., "The rab16B Promoter of Rice Contains Two Distinct Abscisic Acid-Responsive Elements" (1996) Plant Physiology 112:483-491.
Park, S. et al., "Cis-Acting Elements Essential for Light Regulation of the Nuclear Gene Encoding the A Subunit of Chloroplast Glyceraldehyde 3-Phosphate Dehydrogenase in *Arabidopsis thaliana*" (1996) Plant Physiology 112:1563-1571.
Pastuglia, M. et al., "A Functional S Locus Anther Gene Is Not Required for the Self-Incompatibility Response in Brassica oleracea" (1997) The Plant Cell 9:2065-2076.
Quackenbush, J. et al., "The TIGR Gene Indices: analysis of gene transcript sequences in highly sampled eukaryotic species" (2001) Nucleic Acids Research 29(1):159-164.
Rose, A.B., "Intron-Mediated Regulation of Gene Expression" (2008) Academic Paper University of California, Davis 277-290.
Shah, J. and D.F. Klessig, "Identification of a salicylic acid-responsive element in the promoter of the tobacco pathogenesis-related SS-1,3-glucanase gene, PR-2d" (1996) The Plant Journal 10(6):1089-1101.
Shimono, M. et al., "cDNA microarray anlysis of gene expression in rice plants treated with probenazole, a chemical inducer of disease resistance" (2003) Journal of General Plant Pathology 69:76-82.
Song, W. et al., "A Receptor Kinase-Like Protein Encoded by the Rice Disease Resistance Gene, Xa21" (1995) Science 270:1804-1806.
Sun, X. et al., "Xa26, a gene conferring resistance to *Xanthomonas oryzae* pv. oryzae in rice, encodes an LRR receptor kinase-like protein" (2004) The Plant Journal 37:517-527.
Xiang, Y. et al., "Xa3, conferring resistance for rice bacterial blight and encoding a receptor kinase-like protein, is the same as Xa26" (2006) Theoretical and Applied Genetics 113:1347-1355.

* cited by examiner

*Primary Examiner* — Medina A Ibrahim
*Assistant Examiner* — Russell Boggs
(74) *Attorney, Agent, or Firm* — Elizabeth R. Sampson; John Fado; Lesley Shaw

(57) ABSTRACT

The present invention relates to isolated rice LP2 promoter sequences and uses thereof.

24 Claims, 10 Drawing Sheets
(4 of 10 Drawing Sheet(s) Filed in Color)

SEQ ID NO:1

ATTGAATCCATGAGGATGGTGGGGTGGACACCAGCATACCTAAGAAAATAAAAAAGAAGTTATGGTATAAACTATGTATCAAT
GGCCCAAAAGATTTGATCGGATACTGCACAAACTGAACTACAAGAGGCACGAACCAGCTTTGTGGGCATAATAGCAACAAGAA
AAATAAATATTAGGCAAAATATAAAAGAAAAATATTAGGCAGATTTCACGAGAAAAAAAGCAAAAATATTCGGCCTTAAATT
TTCGAATTAACTTGGTCTAATTTTTTTTTTGCTACCATTATATATGGCTTATGATGGTTTAAAAAAACGTGAATATTAAGGAA
AGACCTAATATCAAATAAATATAAGAGGTGATGTTTCGAATCTATACCAACTAGTCCACTACCTTGTGAAGCTAGCCAGAAGA
TCTCTGGGCCTTTCTCTGTCTTACGATGGTTAACACATCGTCGTCATGGCACCAAAATTAGCTAGACAAT░░░░░░░░░░░░░░
░░░░░░░░░░░░░░░░░░░░░░░░░░░░░░░░░░░░░░░░░░░░░░░░░░░░░░░░░░░░░░░░░░░░░░░░░░░░░░
░░░░░░░░░░░░░░░░░░░░░░░░░░░░░░░░░░░░░░░░░░░░░░░░░░░░░░░░░░░░░░░░░░░░░░░░░░░░░░
░░░░░░░░░░░░░░░░░░░░░░░░░░░░░░░░░░░░░░░░░░░░░░░░░░░░░░░░░░░░░░░░░░░░░░░░░░░░░░
░░░░░░░░░░░░░░░░░░░░░░░░░░░░░░░░░░░░░░░░░░░░░░░░░░░░░░░░░░░░░░░░░░░░░░░░░░░░░░
░░░░░░░░CCCTCGAAAAC░░░░░░░░░░░░░░░░░░░░░░░░░░░░░░░░░░░░░░░░░░░░░░░░░░░░░░░░░░░░
░░░░░░░░░░░░░░░░░░░░░░░░░░░░░░░░░░░░░░░░░░░░░░░░░░░░░░░░░░░░░░░░░░░░░░░░░░░░░░
░░░░░░░░░░░░░░░░░░░░░░░░░░░TTCTCTCGCCTTTTCTTCTCCTGTCATTAATATGAACTTGATT
TTTATAAATGTGATGAACTACGCCAAGACTATGCACGCAACTATTTCCAGACATCTGGTATTGATTTCATATTCAAACCAACG
TGCTTTCGACCTGTTCATTGGGTTGGTGGTCACGGCTGATATTTCACCACTTCCTGAGATATTCATATAATCAGTATGGTGAC
ATAGCCGTGCATGACACGGCATTCGTATGTAGCACTGCTATCCAAATCGAATACATACAAGTTTGCTAGACCCGCTGCTCTGT
CAACGAACGAATCCTGACCGCAGAAACAAATTCTGGAAGAACCAAAATGAATTTGTGGAACGAGAATCTTGAAAGGTAAACCG
TTCATGTGCTCAAAGCTTATCTGCATACAAGCCTTCGAGACCGGTCGCGGCTGTCGCATATCAGCGCAGAATTTCTCTGTCCG
GTTCCGGCTGAAAAGTAGGCGGGATAGATGAATAGTACGGCCATCGGATTCGAGGTTCGAGCTGGACATGCCGCAACAACCTTG
TCCAGATCAAACAGGGACAGCAGCGTTTGGTGATGAGCCGACGAGGTGAAAAGTTGCAGTAACTGGCAGGTTTGACGGACTCC
AGGTCTTGCCTCTAGTGGCGGTCAAGCTGAGATAAGG

+1
AGTGACAATTAAGTGAGTGGATGCGACAATGCTGTAAAACCGTTTTTAAACCCCCGGGACCTGGGAGGCTGCTGAGCAAAGTT
CAGAGTTCACAAACCACCACACCCAGCGGCACCATAGACACCAAGCAGAACAGGCTGCTGAGCTCCGGCCGACCGAAGgtgct
cca|ttctctctcctc|atcattattgatatttgcaggatcgatcacttgag*gtaaatcatagaagctcaaagtgaagtgcgaat*
*atttttgaaaaattgagttttgttctgcttttaagctttgaaaagtcagatgtgttcgtggatgatcacataagcgaccattt*
*gcctcgatcggttagcataggcagcatgccataatgttcatggttgtatattttttgcag*GTAACATGGGCCTCACGT

FIG. 1

SEQ ID NO:2

```
TTCTCTCGCCTTTTCTTCTCCTGTCATTAATATGAACTTGATTTTTATAAATGTGATCAACTACGCCAAGACTATGCACGCAA
CTATTCCAGACATCTGGTATTGATTTCATATTCAAACCAACGTGCTTTCGACCTGTTCATTCGGTTGGTGGTCACGGCTGAT
ATTTCACCACTTCCTGAGATATTCATATAATCAGTATGGTCACATAGCCGTGGATGACACGGCATTCGTATGTAGCACTCCTA
TCCAAATCGAATACATACAAGTTTGCTAGACCCGCTGCTCTGTCAACGAACGAATCCTGACCGCAGAAACAAATTCTGGAAGA
ACCAAAATGAATTTGTGGAACGAGAATCTTGAAAGGTAAACCGTTCATGTGCTCAAAGCTTATCTGCATACAAGCCTTCCAGA
CCGGTCGCGGCTGTCGCATATCAGCGCAGAATTTCTCTGTCCGGTCCGGCTGAAAAGTAGGGGGATAGATGAATAGTACGGC
CATCGGATTCGAGGTTCGAGCTGGACATGCCGCAACAACCTTGTCCAGATCAAACAGGGACAGCAGCGTTTGGTGATGAGCCG
ACGAGGTGAAAAGTTGCAGTAACTGGCAGGTTTGACGGACTCCAGGTCTTGCCTCTAGTGGCGGTCAAGCTGAGATAAGGAGT
GACAATTAAGTGAGTGGATGCGACAATGCTGTAAAACCG TTTTTAAA CCCCGGGACCTGGGAGGCTGCTGAGCAAAGTTCAG
AGTTCACAAACCACCACACCCAGCGGCACCATAGACACCAAGCAGAACAGGCTGCTGAGCTCCGGCCGACCGAAG
```

FIG. 2

SEQ ID NO:3

```
ATTGAATCCATGAGGATGGTGGGGTGGACACCAGCATACCTAAGAAAATAAAAAAGAAGTTATGGTATAAACTATGTATCAAT
GGCCCAAAAGATTTGATGGGATACTGCACAAACTGAACTACAAGAGGCACGAACCAGCTTTGTGGGCATAATAGCAAGAAGAA
AAATAAATATTAGGCAAAATATAAAAAGAAAAATATTAGGCAGATTTCACGAGAAAAAAAGCAAAAATATTCGGCCTTAAATT
TTCGAATTAACTTGGTCTAATTTTTTTTTTGCTACCATTATATATGGCTTATGATGGTTAAAAAAACGTGAATATTAAGGAA
AGACCTAATATCAAATAAATATAAGAGGTGATGTTTCGAATCTATACCAACTAGTCCACTACCTTGTGAAGCTAGCCAGAAGA
TCTCTGGGCGTTTCTCTGTCTTACGATCGTTAACACATCGTCGTCATGGCACCAAAATTAGCTAGACAAT░░░░░░░░░░░░░
░░░░░░░░░░░░░░░░░░░░░░░░░░░░░░░░░░░░░░░░░░░░░░░░░░░░░░░░░░░░░░░░░░░░░░░░░░░░░░░░░░
░░░░░░░░░░░░░░░░░░░░░░░░░░░░░░░░░░░░░░░░░░░░░░░░░░░░░░░░░░░░░░░░░░░░░░░░░░░░░░░░░░
░░░░░░░░░░░░░░░░░░░░░░░░░░░░░░░░░░░░░░░░░░░░░░░░░░░░░░░░░░░░░░░░░░░░░░░░░░░░░░░░░░
AAAAAACACCCTCGAAAAC░░░░░░░░░░░░░░░░░░░░░░░░░░░░░░░░░░░░░░░░░░░░░░░░░░░░░░░░░░░░░░░░
░░░░░░░░░░░░░░░░░░░░░░░░░░░░░░░░░░░░░░░░░░░░░░░░░░░░░░░░░░░TTCTCTCGCCTTTTCTTCTCCTGTCATTAATATGAACTTGATT
TTTATAAATGTGATGAACTACGCCAAGACTATGCACGCAACTATTTCCAGACATCTGGTATTGATTTCATATTCAAACCAACG
TGCTTTCGACCTGTTCATTGGGTTGGTGGTCACGGCTGATATTTCACCACTTCCTGAGATATTCATATAATCAGTATGGTGAC
ATAGCCGTGGATGACACGGCATTCGTATGTAGCACTGCTATCCAAATCGAATACATACAAGTTTGCTAGACCCGCTGCTCTGT
CAACGAACGAATCCTGACCGCAGAAACAAATTCTGGAAGAACCAAAATGAATTTGTGGAACGAGAATCTTGAAAGGTAAACCG
TTCATGTGCTCAAAGCTTATCTGCATACAAGCCTTCGAGACCGGTCGCGGCTGTCGCATATCAGCGCAGAATTTCTCTGTCCG
GTTCCGGCTGAAAAGTAGGGGGATAGATGAATAGTACGGCCATCGGATTCGAGGTTCGAGCTGGACATGCCGCAACAACCTTG
TCCAGATCAAACAGGGACAGCAGCGTTTGGTGATGAGCCGACGAGGTGAAAAGTTGCAGTAACTGGCAGGTTTGACGGACTCC
AGGTCTTGCCTCTAGTGGCGGTCAAGCTGAGATAAGGAGTGACAATTAAGTGAGTGGATGCGACAATGCTGTAAAACCG[TTTT
TAAA]CCCCGGGACCTGGGAGGCTGCTGAGCAAAGTTCAGAGTTCACAAACCACCACACCCAGCGGCACCATAGACACCAAGC
AGAACAGGCTGCTGAGCTCCGGCCGACCGAAGgtgctcca[ttctctctcctc]atcattattgatatttgcaggatcgatcact
tgaggtaaatcatagaagctcaaagtgaagtgcgaatattttttgaaaaattgagttttgttctgcttttaagctttgaaaagt
cagatgtgttcgtggatgatcacataagcgaccatttgcctcgatcggttagcataggcagcatgccataatgttcatggttg
tatattttgcagGTAACATGGGCCTCACGTGTGATACACAAACTGCAAAACTGGCCATTATACTACTAGCATTCATACTGCT
ATGTCATGGGATTGGCAACGTCGATT
```

FIG. 3

SEQ ID NO:4

```
ATTGAATCCATGAGGATGGTGGGGTGGACACCAGCATACCTAAGAAAATAAAAAAGAAGTTATGGTATAAACTATGTATCAAT
GGCCCAAAAGATTTGATGGGATACTGCACAAACTGAACTACAAGAGGCACGAACCAGCTTTGTGGGCATAATAGCAAGAAGAA
AAATAAATATTAGGCAAAATATAAAAAGAAAAATATTAGGCAGATTTCACGAGAAAAAAAGCAAAAATATTCGGCCTTAAATT
TTCGAATTAACTTGGTCTAATTTTTTTTTTGCTACCATTATATATGGCTTATGATGGTTTAAAAAAACGTGAATATTAAGGAA
AGACCTAATATCAAATAAATATAAGAGCTGATGTTTCCAATCTATACCAACTAGTCCACTACCTTGTGAAGCTAGCCAGAACA
TCTCTGGGCGTTTCTCTCTCTTACCATGGTTAACACATCGTCGTCATGGCACCAAAATTAGCTAGACAAT
```

[highlighted/obscured region containing sequence]

```
                                           TTCTCTCGCCTTTCTTCTCCTGTCATTAATATGAACTTGATT
TTTATAAATGTGATGAACTACGCCAAGACTATGCACGCAACTATTCCAGACATCTGGTATTGATTTCATATTCAAACCAACG
TGCTTTCGACCTGTTCATTGGGTTGGTGGTCACGGCTGATATTTCACCACTTCCTGAGATATTCATATAATCAGTATGGTGAC
ATAGCCGTGGATGACACGGCATTCGTATGTAGCACTGCTATCCAAATCGAATACATACAAGTTTGCTAGACCCGCTGCTCTGT
CAACGAACGAATCCTGACCGCAGAAACAAATTCTGGAAGAACCAAAATGAATTTGTGGAACGAGAATCTTGAAAGGTAAACCG
TTCATGTGCTCAAAGCTTATCTGCATACAAGCCTTCGAGACCGGTCGCGGCTGTCGCATATCAGCGCAGAATTTCTCTGTCCG
GTTCCGGCTGAAAAGTAGGGGATAGATGAATAGTACGGCCATCGGATTCGAGGTTCGAGCTGGACATGCCGCAACAACCTTG
TCCAGATCAAACAGGGACAGCAGCGTTTGGTGATGAGCCGACGAGGTGAAAAGTTGCAGTAACTGGCAGGTTTGACGGACTCC
AGGTCTTGCCTCTAGTGGCGGTCAAGCTGAGATAAGG
                                                                              +1
AGTGACAATTAAGTGAGTGGATGCGACAATGCTGTAAAACCGTTTTTAAACCCCGGGACCTGGAGGCTGCTGAGCAAAGTT
CAGAGTTCACAAACCACCACACCCAGCGGCACCATAGACACCAAGCAGAACAGGCTGCTGAGCTCCGGCCGACCGAAG
```

FIG. 4

ATTGAATCCATGAGGATGGTGGGGTGGACACCAGCATACCTAAGAAAATAAAAAAGAAGTTATGGTATAAACTATGTATCA░░░C
░░AAAGATTTGATGGGATACTGCACAAACTGAACTACAAGAGGCACGAACCAGCTTTGTGGGCATAATAGCAAGAAGAAAAATAA
ATATTAGGCAAAATATAAAAAGAAAAATATTAGGCAGATTTCACGAGAAAAAAAGCAAAAATATTCGGCCTTAAATTTTCGAATTA
ACTTGGTCTAATTTTTTTTTTGCTACCATTATATATGGCTTATG░T░░░░AAA░░░░░░GA░TATTAAGGAAAGACCTAATATC
AAATAAATATAAGAGGTGATGTTTCGAATCTATACCAACTAGTCCACTACCTTGTGAAGCTAGCCAGAAGATCTCTGGGCGTTTCT
CTG░░░░GATG░TTAACACATCGTCGTCATGGCACCAAAATTAGCTAGACAAT░░░░░░░░░░░░░░░░░░░░░░░░░░░░░░
░░░░░░░░░░░░░░░░░░░░░░░░░░░░░░░░░░░░░░░░░░░░░░░░░░░░░░░░░░░░░░░░░░░░░░░░░░░░░░░
░░░░░░░░░░░░░░░░░░░░░░░░░░░░░░░░░░░░░░░░░░░░░░░░░░░░░░░░░░░░░░░░░░░░░░░░░░░░░░░
░░░░░░░░░░░░░░░░░░░░░░░░░░░░░░░░░░░░░░░░░░░░░░░░░░░░░░░░░░░░░░░░░░░░░CCCTCC░░░░
CTCTCGCC░T░░░░░░CTGTC░░░░░TATGAACTTGATTTTTATAAATGTGATGAACTACCCAAGACTATGCACGCAACTATT
TCCA░░░░░░░░ATTGATTTCATATTCAAACCAACGTGCTT░░░░░░CTGTTCATTGGTTGCTGGTCACGGCTCATATTTCACC
ACTTCCTGAGATATTCATATAATCAGTATGGTGACATAGCCGTG░░GACA░░░░░░░GTATGTAGCACT░░░░░░CAAATCGAA
TACATACAAGTTTGCTAGACCCGCTGCTCTGTCAACGAACGAATCCTGACCGC░░░░░░░░ATTCTGGAAGAACCAAAATGAATTT
GTGGAACGAGAATCTTGAAAGGT░░░░G░TCATGTGCTCAAAG░TTATC░GCATACAAGCCTTCGAGACCGGTCGCGGCTGTCGC
ATATCAGCGCAGAATTTCTCTGTCCGGTTCCGGCTGAAAAGTAGGCGGGATAGATGAATAGTACGG░░░░░░░░TCGAGGTTCGAG
CTGGACATGCCGCAACAACCTTCTCCAGATCAAACAGGGACAGC░░░░░░GGTG░░░A░░░░GACGAGGTGAAAAGTTCCAG░░░
░░GCAGGTTTGACGGACTCCAGGTCTTGCCTCTAGTGCCGGTCAAGCTGACATAACG

AGTGACAATTAAGTGAGTGGATGCGACAATGCTGTA░░░░G░TTTT░░░░░CCGGGACCTGGGAGGCTGCTGAGCAAAGTTCAG
AGTTCACAAACCACCACACCCAGCGGCACCATAGACACCAAGCAGAACAGGCTGCTGAGCTCCGGCCGACCGAAGgtgctccattc
tctctcctcatcattgatatttgcaggc░░░░░░░░░░░gtaaatcatagaagctcaaagtgaagtgcgaatatttttgaa
aattgagttttgttctgcttttaagc░░░░░░agtcagatgtgttcgtggatgatcacataagcgaccatttgcc░░░░░ggt
tagcataggcagcatgccataatgttcatggttgtatattttttgcagGTAAC░░░░░TCACGT

FIG. 6A

| Site Name | Start Position | Strand | Matrix score | Sequence | Description |
|---|---|---|---|---|---|
| PBX Protein box FORC^ element | -1855, -161, 324 | +, +, + | 6, 6, 7 | ATGCGCC | A.t. PBX diurnal/circadian midnight response element, FORC^ defense/light signaling response element |
| TBX Tata-box | -1634, -1154 -740, -365, -172, -37, -26 | -, +, +, +, -, +, + | 6, 6, 6, 6, 6, 6, 6 | AAACCCT | A.t. diurnal/circadian midnight response element |
| GT1-motif | -1503, -904 | +, + | 6, 6 | KGTTAC | A.t. part of a light responsive element |
| GT1-motif | -1494 | + | 6 | GGTTAA | A.t. light responsive element |
| ATCT-motif | -1366, -1003, -237 | +, +, - | 8, 9, 8 | AATCTGATCC | Z.m. part of a conserved DNA module involved in light responsiveness |
| LPSE2 motif | -1351 | + | 11 | TTGATATATTTGT | O.s. cis-acting element involved in light responsiveness |
| GATA-motif | -1334, -969 | +, + | 9, 10 | AAGATAAGATT | A.t. part of a light responsive element |
| ABRE | -1248, -883 | -, - | 9, 9 | GCCGCGTGGC | O.s. cis-acting element involved in the abscisic acid responsiveness |
| I-box binding site | -1276 -1215, -850 | -, -, - | 9, 10, 8 | AAGATATATT | S.t. light responsive element |
| ACE | -1624 -1092 | +, + | 8, 9 | AAAACGTTTA | P.c. cis-acting element involved in light responsiveness |
| TCCC-motif | -771 | - | 7 | TCTCCCT | S.o. part of a light responsive element |
| TCA element | -724 | - | 9 | GAGAAGAATA | B.o. cis-acting element involved in salicylic acid responsiveness |
| Box 4 | -709 | + | 6 | ATTAAT | P.c. part of a conserved DNA module involved in light responsiveness |
| G-box | -642 | + | 9 | GACATGTCGT | Z.m. cis-acting regulatory element involved in light responsiveness |
| EIRE | -604 | + | 7 | TTCGACC | N.t. elicitor-responsive element |
| Circadian | -516 | - | 6 | CAANNNNATC | L.e. cis-acting regulatory element involved in circadian control |
| GATT-motif | -507 | + | 6 | GCATTC | Z.m. part of a light responsive element |
| ATC-motif | -490 | + | 9 | TGCTATCCA | P.s. part of a conserved DNA module involved in light responsiveness |
| AE-box | -421 | + | 8 | AGAAACAA | A.t. part of a module for light response |
| I-box | -345, -81 | -, + | 7, 8 | AGATAAGG | T.e. part of a light responsive element |
| MBS | -134 | + | 6 | TAACTG | A.t. MYB binding site involved in drought-inducibility |
| Box-W1 | -91 | - | 6 | TTGACC | P.c. fungal elicitor responsive element |
| as-2-box | 108 | - | 9 | GATAatGATG | N.t. involved in shoot-specific expression and light responsiveness |
|  | 131, 263 | +, + | 6, 6 |  | O.s. Intron mediated enhancement motif |
| circ-DMA2a | 135 | + | 8 | TGACTTGA | P.c. part of a light responsive element |
| Box I | 180, 213 | -, - | 7, 7 | TTTCAAA | P.s. light responsive element |

FIG. 6B

SEQ ID NO:5

```
[illegible]GTGGACACCAGCATACCTAAGAAAATAAAAAAGAAGTTATGGTATAAACTATGTATCAATGGCCCAAAAGATTTGATGGGA
TACTGCACAAACTGAACTACAAGAGGCACGAACCAGCTTTGTGGGCATAATAGCAAGAAGAAAAATAAATATTAGGCAAAATATAAAAAGAAAAATATTAGGCA
GATTTCACGAGAAAAAAAGCAAAAATATTCGGCCTTAAATTTTCGAATTAACTTGGTCTAATTTTTTTTTTGCTACCATTATATATGGCTTATGATGGTTTAAA
AAAACGTGAATATTAAGGAAAGACCTAATATCAAATAAATATAAGAGGTGATGTTTCGAATCTATACCAACTAGTCCACTACCTTGTGAAGCTAGCCAGAAGAT
CTCTGGGCGTTTCTCTGTCTTACGATGGTTAACACATCGTCGTCATGGCACCAAAATTAGCTAGACAATGTTTGCTCTAGTCACTCGAAATTATTATCCTAATA
GAGAAAAAAAAGAAAGCATTATATCGTGTGATATAAATAGTTCATATTACAATCTGGTTGATCGATTTATATAATTGTATATAAGATGTGATTGTACTTAATTT
AGTTAGCATAATTTACATGATACTATCTACTACCTAAAATAGATCTTAACACGCATTTGCACATGCCACGCTGCTAGTTAAAGTGATACAATAACAAAAATATT
TCTTGTAGTGTAACACTTAATTGAATTCAATCTCCAACTTGATTGTGAAGTACAAAACCATAGGTCCAGAGTAGTGAAAGCAATATAAGGGACTTGGAAAAAAA
AAACCACCCTCGAAAACGTTTGCTCTAGTCACTCAAAATTATTATCTTAATAGAGCAAAAAAGAAAGCATTATATCGTGTGATATAAATAATTCATATTACAAT
CTGATAGATCAATCTATATATAATTGTATATAAGATATGATTGTACTTAATTTAGTTAGCATAATTTGCATGATACTACCTACTACCTAAAATAGATCTTACCA
CGCATTTGCACAGGCCACGCTGCTAGTTAAACTGATACAATAACAAAGGTATTTCTTGTAGTGTAACACTTAATTGAATTCAATCTCCAACTTGACTGTGAAGT
ACAAAACCAGAGATCCAGAGTAGGGAGAGCAATATAAGGGACTTGGAAAAAAAAACCATTCTCTCGCCTTTTCTTCTCCTGTCATTAATATGAACTTGATTTTT
ATAAATGTGATGAACTACGCCAAGACTATGCACGCAACTATTTCCAGACATCTGGTATTGATTTCATATTCAAACCAACGTGCTTTCGACCTGTTCATTGGGTT
GGTGGTCACGGCTGATATTTCACCACTTCCTGAGATATTCATATAATCAGTATGGTGACATAGCCGTGGATGACACGGCATTCGTATGTAGCACTGCTATCCAA
ATCGAATACATACAAGTTTGCTAGACCCGCTGCTCTGTCAACGAACGAATCCTGACCGCAGAAACAAATTCTGGAAGAACCAAAATGAATTTGTGGAACGAGAA
TCTTGAAAGGTAAACCGTTCATGTGCTCAAAGCTTATCTGCATACAAGCCTTCGAGACCGGTCGCGGCTGTCGCATATCAGCGCAGAATTTCTCTGTCCGGTTC
CGGCTGAAAAGTAGGGGGATAGATGAATAGTACGGCCATCGGATTCGAGGTTCGAGCTGGACATGCCGCAACAACCTTGTCCAGATCAAACAGGGACAGCAGCG
TTTGGTGATGAGCCGACGAGGTGAAAAGTTGCAGTAACTGGCAGGTTTGACGGACTCCAGGTCTTGCCTCTAGTGGCGGTCAAGCTGAGATAAGGAGTGACAAT
TAAGTGAGTGGATGCGACAATGCTGTAAAACCGTTTTTAAACCCCCGGGACCTGGGAGGCTGCT[illegible]
[illegible]
[illegible]ATCCCCCTCACGTCTGATACACAAACTGC
AAAACTGGCCATTATACTACTAGCATTCATACTGCTATGTCATGGGATTGGCAACGTCGATTGCCGTGGGAACAGAGCCGATCAGCTCTCACTGCTTGATTTCA
AGAAGCGCATCACCAACGATCCATATGGAGCCTTGGCCACTTGGAACACCAGCACACATTTCTGTAGGTGGCAAGGTGTCAAGTGCACCTCCACTGGGCCATGG
CGCGTCATGGCGCTCAATCTCTCCAGCCAAAGTTTGACAGGCCAAATAAGGTCCTCTCTCGGAAACCTATCCTTCCTTAATATACTTGACCTCGGCGATAATAA
CTTACTTGGCTCCTTACCTGCCTTGGCAATCTTAGGCAACTTCAGGCACTCTATCTGTATAAAAACAATTTGACAGGGATAATTGCTGATGAACTTACAAATT
GTTCCAGCTTAACGTACATAGACCTCTCAGGGAAATGCCCTAACTGGTGCACTTCCTCCAAATTTAGGCTCTCTGTCCAATCTAGCTTATCTTTATCTTTCTGCG
AACAAGCTAACTGGAACCATCCCGCAGGCCCTTGGCAACATCACCACCTTGGTAGAAATCTATCTTGATACAAATCGATTCGAAGGGGGCATTCCAGACAAGCT
TTGGCAATTGCCGAACTTGACAATTTTGGCCTAGGTCAAAACATGCTATTCGGGTTGATATCCCATTTAACTTCTCCAGCCTTTCTCTTCAACTTTTTAAGCTTGG
AATACAATATGTTCGGCAAGGTATTGCCACAAAACATTAGTCGATATGGTACCCTAATCTCCAAATTCTTCGCTTGGATTACAATATGTTCCAAGGTCAAATCCCA
TCTTCTCTAGGAAATGCTTTGCAGCTAACAGAAATAAGTATGGCAAACAACTACTTCACCGGGCAAATTCCTAGCTCTTTTCGGAAACGTTTCTAAACTCTCCTA
TATTACTCTCCAAAATAATACCCTAGACGCTTCTCATGGCCAAGGCTGCCACTTCCTACACCGCGTTCACAAACTGTAGTAATCTACAACTGTTGTCACTGGCTC
AAAATCAGCTACAAGGAGAAATACCGAATTCAATTGGGGACCTTCCCGCTCAAACTTCAACAGCTAGTGCTGAGTGAAAATAAGCTATCAGGAGAAGTTCCAGCA
AGCATAGGAAACCTTCAGGGCCTGTTTAGGTTAAGCTCTAGATTTGAACAATCTTACTGGCAAAATAGATGAGTGGGTTCCAAAGCTTACAAAACTGCAAAAATT
ACTTCTCCACAGGAACAACTTTAGCGGGCTCGATTCCATCGTCTATAGGCAGAGCTTCCTGGTTTGTCAACGCTTTCATTAGCATATAATGCATTTGATGGTCCCA
TACCATCCTCATTGGGAAACCTTTCAGGACTCCAGAAGTTATATCTAAGTCATAATAATCTCGAACGTGTCATACCTCCAGAGCTTAGTTACCTTAAACAACTA
ATAAATCTAAGTTTATCACAGAAAACAAGCTTACTCGGGAGATCCCTGGCACTTTGAGCCAGTGTAAACACCTGCCAAACATCCAAATCGGCAATAACTTCCTTAC
TGGCAATATCCCAGTAACTTTTGGCGACCTAAAGAGCCTGGGCGTACTCAATCTTTCCCATAACAGCTTGTCGGGCACAATTCCGACTACACTAAATGATCTAC
CAGTCATGAGCAAACTGGACCTTTCATACAATCGTCTCCAAGCGAAAAATACCAATGACTGGAATATTTGCAAATCCTACTGTTGTTTCGGTCCAGGGAAACATA
GGACTATGTGGAGGAGTGATGGATCTCCGTATGCCCCATGCCAAGTTGTTTCCCAGAGAAGAAAAACACAGTACTATTTGATTAGAGTATTGATCCCTATATT
TGGCTTCATGCACCCATATTAGTGGTCTACTTCTTACTTCTTGAGAAATATAAGCCAAGAAAAATATAATCCTCGCAATCTTTTGGTGAGAATTTCCTTA
AAGTCTCATATAATCATCTACCTCAAGCCACAACAAACTTCTCCCACCCTAACCTTATTGGCAAAGGAAGCTATGCTACCCTGTACACAGCTAACTTCAACCAA
TGTAAGGTGGAAGTAGCCGTGAAGGTTTTTGACCTTGAGATGCGAGGTGCCGAAAGAAGCTTCATATCGGAATGTGAAGCTCTCAGAAGCATTCAACATAGAAA
TCTTCTTCCAATCATAACTGCATGCTCGACCGTGGACAGTACGGGCAACGTTTCAAAGCTTAGTTTACGAGTACATGCCTAATGGCAACTTGGACACTTGGA
TACATGACAAAGACGGGTGGGAAAGCTCCCCGGACCTTTGGGTTTAAGACAAACAATTAGCATATGTGTTAACATAGCCGATGCCACTGGACTATTTACACCATGAA
TGCGGAAGAATAACTATCCATTGTGATTGAAAACCCAGCAATATACTTTAGCTGATGACATGAATGCTCTTTGGGAGATTTTGGCATTGCAAGATTTTATAT
CGACTCTTGGTCGACATCAACAGGTTCGAATAGTACAGTCCTCGTTAACCCTACCATAGGGTATATTCCTCAG[illegible]
[illegible]AGTACGCGGGAGGTGGTCATCCATCTACTTCTGGGGATGTTTAT
AGTTTCGGGATAGTGATCCTGGAGCTTATAACAGGAAAAAGACCGACTCGATCCTATGTTCAAAGACCGGACTCGACATTATCAGCTTTGTCGAGAGTAACTTTCC
ACACCAGATATTTCAAGTGATTGATGCTCGACTCGCAGAAAAGTCCATGGACTCCAATCAAACAAATATGACACTGGAAAATGCTGTCCACCAGTGCTTGATAT
CTCTGCTACAACTTGCGCTTTCTTGTACGGGCAAATTACCAAGTGATCGCATGAACATGAAACAAATAGCCAACAAGATGCATTCAATCAAGACGACATATGTT
GGATTGGAAGCTAAGAAATATGGTCCGGCAGTAATGAACAAGATGCATGAAACCCCACGCGTTATTACAGGCGACCCTGAGTCGCGCAACAATTGCAACAT
ATTGATAAGTGTATAGTCCAACAAGAAGAAAATGGTTCTTGTGTGTTAGAAGTTAAGATAATTAAGGTGATAATATGAAGCACTAAAGCGTACCTTCTAACGGT
GATAAATATGAAGATTGTCGATTGTGACTTTATGTCATGGTTTATTTATAACAATATATTACTTCAATAATGTAATAGTATATGTATACGTAGATAATGATGTTG
TACCTAGCATGATCTTGTATTATATGCAAGTTGAACTAAAAAAAACCATTTCTGCAGGCACCCCTGCTTTATTTTC
```

ISOLATED RICE LP2 PROMOTERS AND USES THEREOF

RELATED APPLICATIONS

This application is claims priority to U.S. Provisional Patent Application Ser. No. 61/247,531, filed Sep. 30, 2009 the contents of which are incorporated herein by reference in their entirety.

FIELD OF THE INVENTION

The invention relates to isolated rice LP2 promoter sequences and uses thereof.

BACKGROUND OF THE INVENTION

Plant genetic engineering allows plant breeders to modify the genetic makeup of a plant precisely and predictably. Both alone and in combination with traditional plant breeding techniques, genetic engineering facilitates the creation of improved varieties faster, and with greater ease, than is possible when only traditional plant-breeding techniques are available.

Isolated plant promoters are instrumental for constructing genetically engineered plants. Typically, to produce transgenic plants, an isolated plant promoter is inserted into a vector and operably linked to a heterologous DNA sequence, thereby creating an expression construct. Plant cells are then transformed with the expression construct by any of a number of art recognized methods. The result of transformation is that the plant promoter operably linked to the heterologous DNA, is inserted into the genome of the transformed plant cell, and regulation of the heterologous DNA expression in the transformed plant cell is controlled by the promoter.

There are a variety of different approaches for producing a desired phenotype in a transgenic plant. The chosen approach typically depends on the nature of the heterologous sequences coupled to the isolated plant promoter. For example, expression of a novel gene that is not normally expressed in plant, or in a particular tissue of a plant, may confer a phenotypic change. Alternatively, the expression of a sense or an antisense construct introduced into transgenic plants can cause the inhibition of expression of endogenous plant genes. This inhibition of expression can, in turn, produce a desired phenotypic change.

Unfortunately however, promoter elements capable of directing high levels of transgene expression are difficult to isolate and relatively few promoter control elements have been demonstrated to perform well in crop plants. Thus, promoters useful for the genetic engineering of plants, particularly crop plants, remain limited in number, and as a result, there is a continuing demand for new promoters.

To facilitate the production of precise phenotypes, it is advantageous to have available a variety of different promoters for the genetic engineering of plants. Furthermore, since most of the well-characterized promoters that are currently available confer constitutive expression, novel promoters with reliable organ-specific expression in transgenic plants are needed in the art.

Fortunately, as will be clear from the following disclosure, the present invention provides for these and other needs.

SUMMARY OF THE INVENTION

In an exemplary embodiment, the invention provides an isolated rice LP2 promoter consisting of a nucleic acid sequence that is at least about 90% identical to SEQ ID NO:3 and which is able to control transcription of operably linked nucleic acids in a plant. In one embodiment, the isolated rice LP2 promoter has a nucleic acid sequence is at least about 95% identical to SEQ ID NO:3. In another embodiment, the isolated rice LP2 promoter has a nucleic acid that is capable of hybridizing to SEQ ID NO:2 under stringent hybridization conditions. In another embodiment, the isolated rice LP2 promoter is SEQ ID NO:1. In another embodiment, the isolated rice LP2 promoter is SEQ ID NO:3. In another embodiment, the isolated rice LP2 promoter is SEQ ID NO:4.

In another exemplary embodiment, the invention provides an expression cassette comprising an isolated rice LP2 promoter operably linked to a heterologous nucleic acid sequence. In another embodiment, an expression vector comprises the expression cassette comprising an isolated rice LP2 promoter operably linked to a heterologous nucleic acid sequence.

In another exemplary embodiment, the invention provides a method for making a transgenic plant, the method comprising: (i) transforming a plant, plant part, or plant cell with an expression vector comprising an isolated rice LP2 promoter operably linked to a heterologous nucleic acid sequence, wherein the isolated rice LP2 promoter is capable of controlling transcription of the heterologous nucleic acid in a plant, (ii) selecting transformants comprising the expression vector which comprises the isolated rice LP2 promoter operably linked to a heterologous nucleic acid sequence, and (ii) growing the transformed plant, plant part, or plant cell into a whole plant, thereby producing a transgenic plant. In one embodiment the method further comprises: (iv) conducting a sexual cross with the transgenic plant, (v) obtaining seed from the sexual cross, (vi) growing the seed from the sexual cross, and (vii) selecting plants grown from the seed of the sexual cross which comprise the expression vector comprising an isolated rice LP2 promoter sequence operably linked to a heterologous nucleic acid sequence, thereby producing a transgenic plant.

In another exemplary embodiment, the invention provides a transgenic plant comprising an isolated rice LP2 promoter operably linked to a heterologous nucleic acid sequence. In one embodiment, the plant is a dicotyledonous plant. In another embodiment, the dicotyledonous plant is a member selected from the group consisting of: alfalfa (*Medicago saliva*), sunflower (*Helianthus annus*), soybean (*Glycine max*), tobacco (*Nicotiana tabacum*), potato (*Solanum tuberosum*), peanuts (*Arachis hypogaea*), cotton (*Gossypium hirsutum*), sugar beets (*Beta vulgaris*), apple (*Malus pumila*), blackberry (*Rubus*), strawberry (*Fragaria*), walnut (*Juglans regia*), grape (*Vitis vinifera*), apricot (*Prunus armeniaca*), cherry (*Prunus*), peach (*Prunus persica*), plum (*Prunus domestica*), pear (*Pyrus communis*), watermelon (*Citrullus vulgaris*), tomatoes; (*Solanum lycopersicum*), and lettuce (e.g., *Lactuea sativa*). In another exemplary embodiment, the invention provides the transgenic descendants of the transgenic dicotyledonous plant. In another exemplary embodiment, the invention provides a transgenic plant that is a monocotyledonous plant. In one embodiment the monocotyledonous plant is a member selected from the group consisting of: rice (*Oryza sativa*), wheat (*Triticum aestivum*), durum (*Triticum durum*), barley (*Hordeum vulgare*), switchgrass (*Panicum virgatum*), corn (*Zea mays*), sorghum, (*Sorghum bicolor*), sugarcane (*Saccharum* sp.), rye (*Secale cereale*), oat (*Avena sativa*), banana (*Musa* sp.), millet (*Pennisetum* sp.), onion (*Allium cepa*) and garlic (*Allium sati-* vum). In another exemplary embodiment, the invention provides the transgenic descendants of the transgenic monocotyledonous plant.

In another exemplary embodiment the invention provides a method for controlling transcription of a heterologous nucleic acid sequence in a plant or plant cell, the method comprising: (i) transforming a plant or plant cell with an expression vector comprising an isolated rice LP2 promoter operably linked to the heterologous nucleic acid sequence thereby producing a transformed plant or plant cell; and (ii) growing the transformed plant or plant cell under conditions where the isolated rice LP2 promoter controls transcription of the heterologous nucleic acid in the plant or plant cell. In one embodiment, transcription of a heterologous nucleic acid sequence in a plant or plant cell is induced in response to light. In one embodiment, transcription of a heterologous nucleic acid sequence in a plant or plant cell is induced in response to pest attack. In one embodiment the heterologous nucleic encodes an antimicrobial gene product. In another embodiment, expression of the heterologous nucleic acid up-regulates the expression of a nucleic acid that encodes a gene product that functions in photosynthesis. In another embodiment, the expression of the heterologous nucleic acid down-regulates the expression of an endogenous nucleic acid.

Other features, objects and advantages of the invention will be apparent from the detailed description which follows.

BRIEF DESCRIPTION OF THE DRAWINGS

The patent or application file contains at least one drawing executed in color. Copies of this patent or patent application publication with color drawing(s) will be provided by the Office upon request and payment of the necessary fees.

FIG. 1. Illustrates SEQ ID NO:1 an exemplary isolated rice LP2 promoter comprising an intron sequence. The 2272 bp sequence of the LP2 promoter and coding sequence from −1936 to +336 is shown (GenBank Accession FJ831442). Direct repeat sequences are highlighted in light and dark gray. The LP2 transcription start site is designated +1 and the direction of transcription is shown with an arrow. The putative TATA box is boxed in bold text. The pyrimidine-rich "Y patch" is boxed lower case text. The larger 5' intron sequence is shown in lower case letters with the alternatively spliced smaller intron shown in bold italic lowercase text. The LP2 start codon is underlined.

FIG. 2. Shows SEQ ID NO:2. SEQ ID NO:2 is an exemplary minimal rice LP2 promoter sequence. The "minimal" LP2 promoter sequence, includes the 5' UTR but no 5' intron or Signal Peptide (comprises nucleotides −734 to +88 of SEQ ID NO:1).

FIG. 3. Illustrates SEQ ID NO:3, an exemplary isolated rice LP2 promoter sequence comprising a full length LP2 promoter +5' intron (shown in lowercase)+Signal Peptide coding sequence (underlined), and 5' UTR (comprises nucleotides −1936 to +414 which is SEQ ID NO:1 plus more nucleotides).

FIG. 4 Shows SEQ ID NO:4. SEQ ID NO:4 is an exemplary rice LP2 promoter sequence having the intron sequence deleted.

FIG. 6. FIG. 6A: Cis regulatory motifs within the LP2 sequence. The 2272 bp sequence of the LP2 promoter, intron and coding sequence from −1936 to +336 (GenBank Accession FJ831442) is shown. Direct repeat sequences are highlighted in light and dark gray backshading. The LP2 transcription start site is designated +1 and the direction of transcription is shown with an arrow. The larger 5' intron sequence is shown in lower case letters with the alternatively spliced smaller intron shown in bold italic lowercase text. The LP2 start codon is boxed in bold text. Cis elements are underlined in colored text or highlighted in color with backshading (any LP2 nucleotides that do not match the known cis element sequence remain uncolored). Each cis element is listed in the table in FIG. 6B in the same color as shown in the LP2 sequence. The location of each element relative to the +1 transcription start site, its strand orientation, matrix score, sequence, and corresponding description (including the abbreviation of the species of origin) is shown in FIG. 6B. The cis elements that match the negative DNA strand (−) are highlighted as the reverse complement in the positive strand promoter sequence shown. The matrix score equals the total number of nucleotides that match the known cis element sequence. A.t. *Arabidopsis thaliana*, B.o. *Brassica oleracea*, L.e. *Lycopersicon esculentum*, O.s. *Oryza sativa*, P.c. *Petroselinum crispum*, P.s. *Pisum sativum*, N.t. *Nicotiana tabacum*, S.o. *Spinacia oleracea*, S.t. *Solanum tuberosum*, T.e. *Triticum aestivum*, and Z.m. *Zea mays*.

FIG. 9. Shows an exemplary "isolated rice LP2 gene". The Figure shows the genomic LP2 gene sequence including the promoter, 5' intron, the 5' UTR and the entire coding sequence (including a second intron) and the 3' and terminator sequence (rice genomic gene sequence of LOC_Os02g40240; SEQ ID NO:5).

DETAILED DESCRIPTION OF THE INVENTION

Definitions

Figure 5:
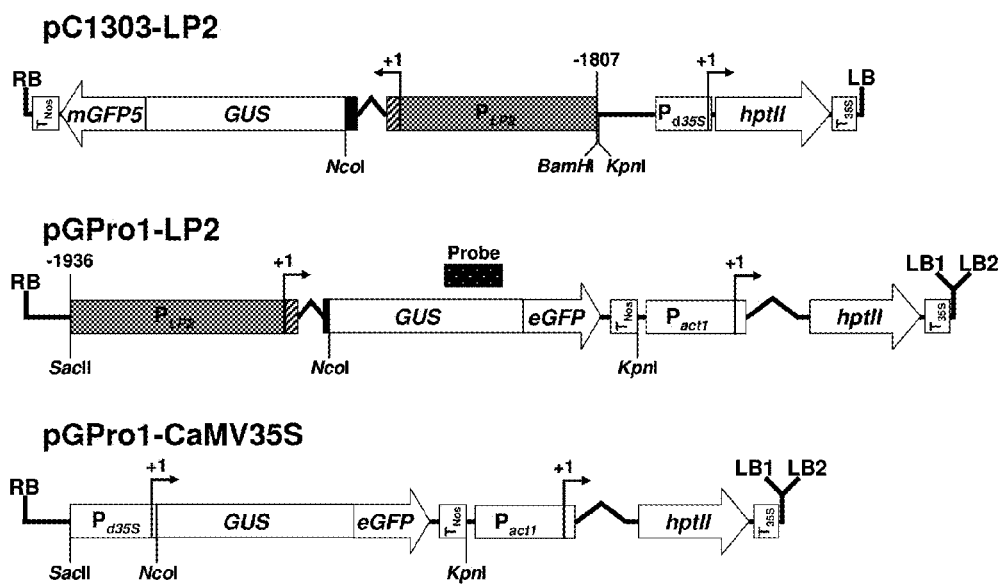
FIG. 5. Shows the pC1303-LP2 binary vector which is a derivative of pCAMBIA1303, while the pGPro1-LP2 and pGPro1-CaMV35S binary vectors are derivatives of the pGreen binary vector pGPro1. Both vectors contain a GUS::GFP gene fusion which encodes a bifunctional reporter protein. RB Right Border, LB Left border (the pGPro1 constructs have two left borders in tandem), $P_{LP2}$ rice Leaf Panicle2 promoter, $P_{d35S}$ double enhanced CaMV35S promoter, $P_{act1}$ rice Actin1 promoter, $T_{35S}$ CaMV35S terminator, $T_{nos}$ nopalene synthase terminator, hptII hygromycin phosphotransferase II gene, GUS β-glucuronidase gene, mGFP5 modified green fluorescent protein gene 5, eGFP enhanced green fluorescent protein gene. Transcription start sites are designated +1 and the direction of transcription is shown with an arrow. The LP2 promoter (gray), 5' UTR (hashed box) is translationally fused to the reporter gene (the partial LP2 coding region is shown as a black rectangle). The 5' LP2 and Actin1 introns are drawn as diagonal lines. The locations of unique restriction sites used for promoter cloning and genomic DNA digestion for DNA blot hybridization are shown. The 496 bp GUS region used as a probe for DNA and RNA blot hybridization is shown as a black stippled box.

The term "plant" as used herein refers to whole plants, plant bodies, plant organs (e.g., leaves, stems, flowers, roots, etc.), seeds, plant tissues, plant cells and progeny of same. In an exemplary embodiment, a plant cell includes callus. In another exemplary embodiment, a plant organ includes a root, a leaf, a flower and/or the like. The term "plant" refers to the broad class of higher plants amenable to transformation techniques. The term "plant" also includes plants of any variety of ploidy levels, including polyploid, diploid, haploid and hemizygous.

Some exemplary plants include, but are not limited, to alfalfa (*Medicago saliva*), sunflower (*Helianthus annus*), soybean (*Glycine max*), tobacco (*Nicotiana tabacum*), potato (*Solanum tuberosum*), peanuts (*Arachis hypogaea*), cotton (*Gossypium hirsutum*), sweet potato (*Ipomoea batatus*), cassava (*Manihot esculenta*), wheat (*Triticum* spp), rice (*Oryza sativa*), barley (*Hordeum vulgare*), oats (*Avena sativa*), maize (*Zea mays*), rye (*Secale cereale*), onion (*Allium* spp), pineapple (*Ananas comosus*), citrus trees (*Citrus* spp.), cocoa (*Theobroma cacao*), tea (*Camellia sinensis*), banana (*Musa* spp.), avocado (*Persea americana*), fig (*Ficus casica*), papaya (*Carica papaya*), almond (*Prunus amygdalus*), sugar beets (*Beta vulgaris*), apple (*Malus pumila*), blackberry (*Rubus*), strawberry (*Fragaria*), walnut (*Juglans regia*), grape (*Vitis vinifera*), apricot (*Prunus armeniaca*), cherry (*Prunus*), peach (*Prunus persica*), plum (*Prunus domestica*), pear (*Pyrus communis*), watermelon (*Citrullus vulgaris*), tomatoes; (*Solanum lycopersicum*), lettuce (e.g., *Lactuea sativa*), carrots (*Caucuis carota*), cauliflower (*Brassica oleracea*), celery (*apium graveolens*), eggplant (*Solanum melongena*), asparagus (*Asparagus officinalis*), ochra (*Abelmoschus esculentus*), green beans (*Phaseolus vulgaris*), lima beans (*Phaseolus limensis*), peas (*Lathyrus* spp.), members of the genus *Cucurbita* e.g., Hubbard squash (*C. Hubbard*), Butternut squash (*C. moschtata*), Zucchini (*C. pepo*), Crookneck squash (*C. crookneck*), *C. argyrosperma*, *C. argyrosperma* ssp *sororia*, *C. digitata*, *C. ecuadorensis*, *C. foetidissima*, *C. lundelliana*, and *C. martinezii*, and members of the genus *Cucumis* such as cucumber (*Cucumis sativus*), cantaloupe (*C. cantalupensis*), and musk melon (*C. melo*). Ornamental plants e.g., azalea (*Rhododendron* spp.), hydrangea (*Macrophylla hydrangea*), hibiscus (*Hibiscus rosasanensis*), roses (*Rosa* spp.), tulips (*Tulipa* spp.), daffodils (*Narcissus* spp.), petunias (*Petunia hybrida*), carnation (*Dianthus caryophyllus*), poinsettia (*Euphorbia pulcherima*), and chrysanthemum, and laboratory plants, e.g., *Arabidopsis*.

The term "transgenic plant" as used herein refers to a plant comprising at least one heterologous nucleic acid sequence that was introduced into the plant, at some point in its lineage, by genetic engineering techniques. In an exemplary embodiment, a transgenic plant is a plant that is transformed with an expression vector comprising an isolated rice LP2 promoter nucleic acid. In another exemplary embodiment, a transgenic plant is a plant that is the progeny or descendant of a plant that is transformed with an expression vector comprising an isolated rice LP2 promoter nucleic acid and which comprises the expression vector comprising an isolated rice LP2 promoter nucleic acid. Thus, the term "transgenic plant" refers to plants which are the direct result of transformation with a heterologous nucleic acid or transgene, and the progeny and descendants of transformed plants which comprise the introduced heterologous nucleic acid or transgene.

The terms "isolated," "purified," or "biologically pure" as used herein, refer to material that is substantially or essentially free from components that normally accompany it as found in its native state. In an exemplary embodiment, purity and homogeneity are determined using analytical chemistry techniques such as polyacrylamide gel electrophoresis or high performance liquid chromatography. A nucleic acid that is the predominant species present in a preparation is substantially purified. In one exemplary embodiment, an isolated rice LP2 promoter nucleic acid is separated from open reading frames and/or other nucleic acid sequences that flank the isolated rice LP2 promoter in its native state. In some exemplary embodiments, an isolated rice LP2 promoter comprises a 5' intron. In other exemplary embodiments, an isolated rice LP2 promoter does not comprise a 5' intron. In an exemplary embodiment, the term "purified" denotes that a nucleic acid or protein gives rise to essentially one band in an electrophoretic gel. Typically, isolated nucleic acids or proteins have a level of purity expressed as a range. The lower end of the range of purity for the component is about 60%, about 70% or about 80% and the upper end of the range of purity is about 70%, about 80%, about 90% or more than about 90%.

The term "nucleic acid" as used herein, refers to a polymer of ribonucleotides or deoxyribonucleotides. Typically, "nucleic acid" polymers occur in either single- or double-stranded form, but are also known to form structures comprising three or more strands. The term "nucleic acid" includes naturally occurring nucleic acid polymers as well as nucleic acids comprising known nucleotide analogs or modified backbone residues or linkages, which are synthetic, naturally occurring, and non-naturally occurring, which have similar binding properties as the reference nucleic acid, and which are metabolized in a manner similar to the reference nucleotides. Examplary analogs include, without limitation, phosphorothioates, phosphoramidates, methyl phosphonates, chiral-methyl phosphonates, 2-O-methyl ribonucleotides, peptide-nucleic acids (PNAs).

Unless otherwise indicated, a particular nucleic acid sequence also implicitly encompasses conservatively modified variants thereof (e.g., degenerate codon substitutions) and complementary sequences, as well as the sequence explicitly indicated. Specifically, degenerate codon substitutions may be achieved by generating sequences in which the third position of one or more selected (or all) codons is substituted with mixed-base and/or deoxyino sine residues (see e.g., Batzer et al., Nucleic Acid Res. 19:5081 (1991); Ohtsuka et al., J. Biol. Chem. 260:2605-2608 (1985); and Rossolini et al., Mol. Cell. Probes 8:91-98 (1994)).

The terms "polypeptide," "peptide" and "protein" are used interchangeably herein to refer to a polymer of amino acid residues. The terms apply to naturally occurring amino acid polymers and non-naturally occurring amino acid polymers as well as amino acid polymers in which one or more amino acid residues is an artificial chemical mimetic of a corresponding naturally occurring amino acid.

The term "amino acid" refers to naturally occurring and synthetic amino acids, as well as amino acid analogs and amino acid mimetics that function in a manner similar to the naturally occurring amino acids. Naturally occurring amino acids are those encoded by the genetic code, as well as those amino acids that are later modified, e.g., hydroxyproline, γ-carboxyglutamate, and O-phosphoserine. Amino acid analogs refers to compounds that have the same basic chemical structure as a naturally occurring amino acid, i.e., an α carbon that is bound to a hydrogen, a carboxyl group, an amino group, and an R group, e.g., homoserine, norleucine, methionine sulfoxide, methionine methyl sulfonium. Such analogs have modified R groups (e.g., norleucine) or modified peptide backbones, but retain the same basic chemical structure as a naturally occurring amino acid. Amino acid mimetics refers to chemical compounds that have a structure that is different from the general chemical structure of an amino acid, but that functions in a manner similar to a naturally occurring amino acid.

Amino acids are referred to herein by either their commonly known three letter symbols or by the one-letter symbols recommended by the IUPAC-IUB Biochemical Nomenclature Commission. Nucleotides, likewise, may be referred to by their commonly accepted single-letter codes.

"Conservatively modified variants" applies to both amino acid and nucleic acid sequences. With respect to particular nucleic acid sequences, conservatively modified variants refers to those nucleic acids which encode identical or essentially identical amino acid sequences, or where the nucleic acid does not encode an amino acid sequence, to essentially identical sequences. Because of the degeneracy of the genetic code, a large number of functionally identical nucleic acids encode any given protein. For instance, the codons GCA, GCC, GCG and GCU all encode the amino acid alanine. Thus, at every position where an alanine is specified by a codon, the codon can be altered to any of the corresponding codons described without altering the encoded polypeptide. Such nucleic acid variations are "silent variations," which are one species of conservatively modified variations. Every nucleic acid sequence herein which encodes a polypeptide also describes every possible silent variation of the nucleic acid. One of skill will recognize that each codon in a nucleic acid (except AUG, which is ordinarily the only codon for methionine, and TGG, which is ordinarily the only codon for tryptophan) can be modified to yield a functionally identical molecule. Accordingly, each silent variation of a nucleic acid which encodes a polypeptide is implicit in each described sequence.

As to amino acid sequences, one of skill will recognize that individual substitutions, deletions or additions to a nucleic acid, peptide, polypeptide, or protein sequence which alters, adds or deletes a single amino acid or a small percentage of amino acids in the encoded sequence is a "conservatively modified variant" where the alteration results in the substitution of an amino acid with a chemically similar amino acid. Conservative substitution tables providing functionally similar amino acids are well known in the art (see, e.g., Creighton, Proteins (1984)). Such conservatively modified variants are in addition to and do not exclude polymorphic variants, interspecies homologs, and alleles.

The following eight groups illustrate some exemplary amino acids that are conservative substitutions for one another:
 1) Alanine (A), Glycine (G);
 2) Aspartic acid (D), Glutamic acid (E);
 3) Asparagine (N), Glutamine (Q);
 4) Arginine (R), Lysine (K);
 5) Isoleucine (I), Leucine (L), Methionine (M), Valine (V);
 6) Phenylalanine (F), Tyrosine (Y), Tryptophan (W);
 7) Serine (S), Threonine (T); and
 8) Cysteine (C), Methionine (M)

Macromolecular structures such as polypeptide structures are described in terms of various levels of organization. For a general discussion of this organization, see, e.g., Alberts et al., Molecular Biology of the Cell (3$^{rd}$ ed., 1994) and Cantor and Schimmel, Biophysical Chemistry Part I: The Conformation of Biological Macromolecules (1980). "Primary structure" refers to the amino acid sequence of a particular peptide. "Secondary structure" refers to locally ordered, three dimensional structures within a polypeptide. These structures are commonly known as domains. Domains are portions of a polypeptide that form a compact unit of the polypeptide and are typically 50 to 350 amino acids long. Typical domains are made up of sections of lesser organization such as stretches of β-sheet and α-helices. "Tertiary structure" refers to the complete three dimensional structure of a polypeptide monomer. "Quaternary structure" refers to the three dimensional structure formed by the noncovalent association of independent tertiary units. Anisotropic terms are also known as energy terms.

The term "label" as used herein, refers to a composition detectable by spectroscopic, photochemical, biochemical, immunochemical, or chemical means. Exemplary labels include $^{32}$P, fluorescent dyes, electron-dense reagents, enzymes (e.g., as commonly used in an ELISA), biotin, digoxigenin, or haptens and proteins for which antisera or monoclonal antibodies are available.

As used herein a "nucleic acid probe or oligonucleotide" refers to a nucleic acid capable of binding to a target nucleic acid of complementary sequence through one or more types of chemical bonds, usually through complementary base pairing, usually through hydrogen bond formation. As used herein, a probe may include natural (i.e., A, G, C, or T) or modified bases (e.g., 7-deazaguanosine, inosine, etc.). In addition, the bases in a probe may be joined by a linkage other than a phosphodiester bond, so long as it does not interfere with hybridization. Thus, for example, probes may be peptide nucleic acids in which the constituent bases are joined by peptide bonds rather than phosphodiester linkages. It will be understood by one of skill in the art that probes may bind target sequences lacking complete complementarity with the probe sequence depending upon the stringency of the hybridization conditions. In one exemplary embodiment, probes are directly labeled as with isotopes, chromophores, lumiphores, chromogens etc. In other exemplary embodiments probes are indirectly labeled e.g., with biotin to which a streptavidin complex may later bind. By assaying for the presence or absence of the probe, one can detect the presence or absence of the select sequence or subsequence.

Thus, the term "labeled nucleic acid probe or oligonucleotide" as used herein refers to a probe that is bound, either covalently, through a linker or a chemical bond, or noncovalently, through ionic, van der Waals, electrostatic, or hydrogen bonds to a label such that the presence of the probe may be detected by detecting the presence of the label bound to the probe.

The term "primer" as used herein, refers to short nucleic acids, typically DNA oligonucleotides of at least about 15 nucleotides in length. In an exemplary embodiment, primers are annealed to a complementary target DNA strand by nucleic acid hybridization to form a hybrid between the primer and the target DNA strand. Annealed primers are then extended along the target DNA strand by a DNA polymerase enzyme. Primer pairs can be used for amplification of a nucleic acid sequence, e.g., by the polymerase chain reaction (PCR) or other nucleic-acid amplification methods known in the art.

PCR primer pairs are typically derived from a known sequence, for example, by using computer programs intended for that purpose such as Primer (Version 0.5 ©1991, Whitehead Institute for Biomedical Research, Cambridge, Mass.). One of skill in the art will appreciate that the specificity of a particular probe or primer increases with its length. Thus, for example, a primer comprising 20 consecutive nucleotides of an isolated rice LP2 promoter complex sequence will anneal to a related target sequence with a higher specificity than a corresponding primer of only 15 nucleotides. Thus, in an exemplary embodiment, greater specificity of a nucleic acid primer or probe is attained with probes and primers selected to comprise 20, 25, 30, 35, 40, 50 or more consecutive nucleotides of a selected sequence.

Nucleic acid probes and primers are readily prepared based on the nucleic acid sequences disclosed herein. Methods for preparing and using probes and primers and for labeling and guidance in the choice of labels appropriate for various purposes are discussed, e.g., in Sambrook et al., *Molecular Cloning, A Laboratory Manual* 2nd ed. 1989, Cold Spring Harbor Laboratory; and *Current Protocols in Molecular Biology*, Ausubel et al., eds., 1994, John Wiley & Sons). The term "recombinant" when used with reference, e.g., to a cell, or nucleic acid, protein, or vector, indicates that the cell, nucleic acid, protein or vector, has been modified by the introduction of a heterologous nucleic acid or protein or the alteration of a native nucleic acid or protein, or that the cell is derived from a cell so modified. Thus, for example, recombinant cells express genes that are not found within the native (non-recombinant) form of the cell or express native genes that are otherwise abnormally expressed, over expressed, under expressed or not expressed at all.

The term "promoter" or "promoter complex" or "promoter sequence" as used herein refers to an array of nucleic acid expression control sequences that direct transcription of a nucleic acid. As used herein, a "promoter" or "promoter complex" or "promoter sequence" comprises necessary nucleic acid sequences near the start site of transcription, such as, e.g., a polymerase II type promoter, a TATA element etc to "control" transcription of an operably linked nucleic acid. In some exemplary embodiments, a "promoter complex" or "promoter sequence" also includes distal enhancer or repressor elements, which can be, but are not necessarily located as much as several thousand base pairs from the start site of transcription. In other exemplary embodiments, "promoter" or "promoter complex" or "promoter sequence" includes sequences that facilitate transcription of an operably linked heterologous nucleic acid and/or expression of the final protein product of the heterologous nucleic acid e.g., intron sequence and/or intron and ubiquitin monomer sequences as disclosed herein.

As is well known in the art, a "constitutive" promoter is a promoter that is active under most environmental and developmental conditions. An "inducible" promoter is a promoter that is active under environmental conditions e.g., in response to light, or developmental regulation, e.g., upregulation in selected plant tissues e.g., upregulation in mesophyll cells. Promoters may be derived in their entirety from a native gene, may comprise one or more a segments or fragments of a native gene, or may be composed of different elements derived from different promoters found in nature, or even comprise synthetic DNA segments. It is understood by those skilled in the art that different promoters may direct the expression of a gene in different tissues or cell types, or at different stages of development, or in response to different environmental or physiological conditions. It is further understood that the same promoter may be differentially expressed in different tissues and/or differentially expressed under different conditions.

The term "isolated rice LP2 promoter" or "isolated rice LP2 promoter sequence" or "isolated rice LP2 promoter nucleic acid" or "isolated rice LP2 promoter complex" or "LP2 promoter", or "isolated LP2 promoter" as used herein, refers to isolated plant promoters which consist essentially of a nucleotide sequences identical to or substantially identical to SEQ ID NO:3 or segment or fragment thereof wherein the nucleotide sequences identical to or substantially identical to SEQ ID NO:3 or segment or fragment thereof comprise a nucleotide sequence identical to or substantially identical to SEQ ID NO:2 and which are able to control transcription of operably linked nucleic acids in plants. Thus, an exemplary isolated rice LP2 promoter consists of a nucleotide sequence as shown in SEQ ID NO:3 or segment or fragment thereof. In one exemplary embodiment, an "isolated LP2 promoter" refers to isolated plant promoters consisting of a nucleotide sequence identical to or substantially identical to SEQ ID NO:3 which comprise a nucleotide sequence identical to or substantially identical to SEQ ID NO:2, and which are able to control transcription of operably linked nucleic acids in plants. Thus, an exemplary isolated rice LP2 promoter sequence is as SEQ ID NO:1. Another exemplary isolated rice LP2 promoter is SEQ ID NO:2. Still another exemplary isolated rice LP2 promoter is illustrated as SEQ ID NO:4. Typically, isolated rice LP2 promoter sequences are derived from the Leaf Panicle 2 (LP2) gene of japonica rice. However, isolated rice LP2 promoter sequences can be isolated from any source and/or can be synthetically made, by methods known on the art (see e.g., U.S. Pat. No. 5,942,609) as long as they are substantially identical to isolated rice LP2 promoter sequences as disclosed herein. Methods for determining nucleotide sequence identity and "substantial identity" are described below. However, in general, two nucleic acid sequences are considered to be substantially identical when the two molecules or their complements hybridize to each other under stringent hybridization conditions, as described below.

The term "capable of hybridizing under stringent hybridization conditions" as used herein, refers to annealing a first nucleic acid to a second nucleic acid under stringent hybridization conditions (defined below). In an exemplary embodiment, the first nucleic acid is a test sample, and the second nucleic acid is the sense or antisense strand of an isolated rice LP2 promoter. Hybridization of the first and second nucleic acids is conducted under standard stringent conditions, e.g., high temperature and/or low salt content, which tend to disfavor hybridization of dissimilar nucleotide sequences.

The expression "control transcription", "controlling transcription" or "control of transcription" or other grammatically equivalent phrases or expressions as used herein refers to the ability of an "expression control sequence" typically a promoter, e.g., an isolated rice LP2 promoter, to direct transcription of an operably linked nucleic acid sequence. Methods for testing the activity of promoters and putative promoters in plant cells are known in the art see e.g., L. Szabados et al. (1995) Molecular Breeding 1(4):419-423 and Y. Yang et al. (2000) The Plant Journal, 22(6): 543-551. A promoter that is "able to control transcription of operably linked nucleic acids in plants" refers to promoters that can direct transcription of an operably linked nucleic acid sequence in a plant cell. In an exemplary embodiment, "controlling transcription" refers to initiating transcription. In another exemplary embodiment, "controlling transcription" refers to up-regulating transcription over a basal constitutive level of transcription.

The term "operably linked" refers to a functional linkage between a nucleic acid expression control sequence (such as e.g., an isolated rice LP2 promoter, or array of transcription factor binding sites) and a second nucleic acid sequence, wherein the expression control sequence directs expression e.g., transcription, of the nucleic acid corresponding to the second sequence. In an exemplary embodiment, a promoter e.g., an isolated rice LP2 promoter, that is "operably linked" to a heterologous nucleic acid is located upstream of and in-frame with the heterologous nucleic acid.

The term "heterologous" when used with reference to portions of a nucleic acid indicates that the nucleic acid comprises two or more subsequences that are not found in the same relationship to each other in nature. For instance, the nucleic acid is typically recombinantly produced, having two or more sequences from unrelated genes arranged to make a new functional nucleic acid, e.g., a promoter from one source and a coding region from another source. Similarly, a heterologous protein indicates that the protein comprises two or more subsequences that are not found in the same relationship to each other in nature (e.g., a fusion protein).

An "expression cassette" as used herein, refers to a nucleic acid construct, typically generated recombinantly or synthetically, which comprises a series of specified nucleic acid elements that permit transcription of a particular nucleic acid in a host cell. In an exemplary embodiment, an expression cassette comprises a heterologous nucleic acid to be transcribed, operably linked to a promoter e.g., an isolated rice LP2 promoter.

Typically, an "expression cassette" is part of an "expression vector". The term "vector" as used herein, refers to nucleic acid capable of replicating in a selected host cell or organism. A vector can replicate as an autonomous structure, or alternatively can integrate into the host cell chromosomes and thus replicate along with the host cell genome. Thus, an "expression vector" is a nucleic acids capable of replicating in a selected host cell or organism e.g., a plasmid, virus, artificial chromosome, nucleic acid fragment, or any suitable construct known in the art, which comprises an "expression cassette".

The term "transformation" as used herein encompasses any and all techniques by which a nucleic acid molecule might be introduced into a cell, including but not limited to, transfection with viral vectors, transformation with plasmid vectors, and introduction of naked DNA by electroporation, lipofection, *Agrobacterium* infection, and particle gun acceleration.

The following terms are used to describe the sequence relationships between two or more nucleic acids or polynucleotides: "reference sequence", "comparison window", "sequence identity", "percentage of sequence identity", and "substantial identity". A "reference sequence" is a defined sequence used as a basis for a sequence comparison; a reference sequence may be a subset of a larger sequence, for example, as a segment of a full-length isolated rice LP2 promoter sequence or gene sequence given in a sequence listing, or may comprise a complete isolated rice LP2 promoter sequence or gene sequence.

The terms "identical" or percent "identity," in the context of two or more nucleic acids or polypeptide sequences, refer to two or more sequences or subsequences that are the same or have a specified percentage of amino acid residues or nucleotides that are the same (e.g., 85% identity, 90% identity, 99%, or 100% identity), when compared and aligned for maximum correspondence over a comparison window, or designated region as measured using a sequence comparison algorithm or by manual alignment and visual inspection.

The phrase "substantially identical", in the context of two nucleic acids or polypeptides, refers to two or more sequences or subsequences that have at least about 85%, identity, at least about 86%, 87%, 88%, 89%, 90%, 91%, 92%, 93%, 94%, 95%, 96%, 97%, 98%, 99%, or 100% nucleotide or amino acid residue identity, when compared and aligned for maximum correspondence, as measured using a sequence comparison algorithm or by visual inspection. In an exemplary embodiment, the substantial identity exists over a region of the sequences that is at least about 50 residues in length. In another exemplary embodiment, the substantial identity exists over a region of the sequences that is at least about 100 residues in length. In still another exemplary embodiment, the substantial identity exists over a region of the sequences that is at least about 150 residues or more, in length. In one exemplary embodiment, the sequences are substantially identical over the entire length of nucleic acid or protein sequence.

For sequence comparison, typically one sequence acts as a reference sequence, to which test sequences are compared. When using a sequence comparison algorithm, test and reference sequences are entered into a computer, subsequence coordinates are designated, if necessary, and sequence algorithm program parameters are designated. Default program parameters can be used, or alternative parameters can be designated. The sequence comparison algorithm then calculates the percent sequence identities for the test sequences relative to the reference sequence, based on the program parameters.

A "comparison window", as used herein, includes reference to a segment of any one of the number of contiguous positions selected from the group consisting of from 20 to 600, usually about 50 to about 200, more usually about 100 to about 150 in which a sequence may be compared to a reference sequence of the same number of contiguous positions after the two sequences are optimally aligned. Methods of alignment of sequences for comparison are well-known in the art. Optimal alignment of sequences for comparison can be conducted, e.g., by the local homology algorithm of Smith & Waterman, Adv. Appl. Math. 2:482 (1981), by the homology alignment algorithm of Needleman & Wunsch, J. Mol. Biol. 48:443 (1970), by the search for similarity method of Pearson & Lipman, Proc. Nat'l. Acad. Sci. USA 85:2444 (1988), by computerized implementations of these algorithms (GAP, BESTFIT, FASTA, and TFASTA in the Wisconsin Genetics Software Package, Genetics Computer Group, 575 Science Dr., Madison, Wis.), or by manual alignment and visual inspection (see, e.g., Current Protocols in Molecular Biology (Ausubel et al., eds. 1995 supplement)).

An exemplary algorithm for sequence comparison is PILEUP. PILEUP creates a multiple sequence alignment from a group of related sequences using progressive, pairwise alignments to show relationship and percent sequence identity. It also plots a tree or dendogram showing the clustering relationships used to create the alignment. PILEUP uses a simplification of the progressive alignment method of Feng & Doolittle, J. Mol. Evol. 35:351-360 (1987). The method used is similar to the method described by Higgins & Sharp, CABIOS 5:151-153 (1989). The program can align up to 300 sequences, each of a maximum length of 5,000 nucleotides or amino acids. The multiple alignment procedure begins with the pairwise alignment of the two most similar sequences, producing a cluster of two aligned sequences. This cluster is then aligned to the next most related sequence or cluster of aligned sequences. Two clusters of sequences are aligned by a simple extension of the pairwise alignment of two individual sequences. The final alignment is achieved by a series of progressive, pairwise alignments. The program is run by designating specific sequences and their amino acid or nucleotide coordinates for regions of sequence comparison and by designating the program parameters. Using PILEUP, a reference sequence is compared to other test sequences to determine the percent sequence identity relationship using the following parameters: default gap weight (3.00), default gap length weight (0.10), and weighted end gaps. PILEUP can be obtained from the GCG sequence analysis software package, e.g., version 7.0 (Devereaux et al., Nuc. Acids Res. 12:387-395 (1984).

Another example of algorithm that is suitable for determining percent sequence identity and sequence similarity are the BLAST and BLAST 2.0 algorithms, which are described in Altschul et al., Nuc. Acids Res. 25:3389-3402 (1977) and Altschul et al., J. Mol. Biol. 215:403-4ID (1990), respectively. Software for performing BLAST analyses is publicly available through the National Center for Biotechnology Information. This algorithm involves first identifying high scoring sequence pairs (HSPs) by identifying short words of length W in the query sequence, which either match or satisfy some positive-valued threshold score T when aligned with a word of the same length in a database sequence. T is referred to as the neighborhood word score threshold (Altschul et al., supra). These initial neighborhood word hits act as seeds for initiating searches to find longer HSPs containing them. The word hits are extended in both directions along each sequence for as far as the cumulative alignment score can be increased. Cumulative scores are calculated using, for nucleotide sequences, the parameters M (reward score for a pair of matching residues; always >0) and N (penalty score for mismatching residues; always <0). For amino acid sequences, a scoring matrix is used to calculate the cumulative score. Extension of the word hits in each direction are halted when: the cumulative alignment score falls off by the quantity X from its maximum achieved value; the cumulative score goes to zero or below, due to the accumulation of one or more negative-scoring residue alignments; or the end of either sequence is reached. The BLAST algorithm parameters W, T, and X determine the sensitivity and speed of the alignment. The BLASTN program (for nucleotide sequences) uses as defaults a wordlength (W) of 11, an expectation (E) or ID, M=5, N4 and a comparison of both strands. For amino acid sequences, the BLASTP program uses as defaults a wordlength of 3, and expectation (E) of ID, and the BLOSUM62 scoring matrix (see Henikoff & Henikoff, Proc. Natl. Acad. Sci. USA 89:ID915 (1989)) alignments (B) of 50, expectation (E) of ID, M=5, N=4, and a comparison of both strands.

The BLAST algorithm also performs a statistical analysis of the similarity between two sequences (see, e.g., Karlin & Altschul, Proc. Nat'l. Acad. Sci. USA 90:5873-5787 (1993)). One measure of similarity provided by the BLAST algorithm is the smallest sum probability (P(N)), which provides an indication of the probability by which a match between two nucleotide or amino acid sequences would occur by chance. For example, a nucleic acid is considered similar to a reference sequence if the smallest sum probability in a comparison of the test nucleic acid to the reference nucleic acid is less than about 0.2, more preferably less than about 0.01, and most preferably less than about 0.001.

An indication that two nucleic acid sequences or polypeptides are substantially identical is that the polypeptide encoded by the first nucleic acid is immunologically cross reactive with the antibodies raised against the polypeptide encoded by the second nucleic acid, as described below. Thus, a polypeptide is typically substantially identical to a second polypeptide, for example, where the two peptides differ only by conservative substitutions. Another indication that two nucleic acid sequences are substantially identical is that the two molecules or their complements hybridize to each other under stringent conditions, as described below. Yet another indication that two nucleic acid sequences are substantially identical is that the same primers can be used to amplify the sequence.

The phrase "selectively (or specifically) hybridizes to" refers to the binding, duplexing, or hybridizing of a molecule only to a particular nucleotide sequence under stringent hybridization conditions when that sequence is present in a complex mixture (e.g., total cellular or library DNA or RNA). In general, two nucleic acid sequences are said to be "substantially identical" when the two molecules or their complements selectively or specifically hybridize to each other under stringent conditions.

The phrase "stringent hybridization conditions" refers to conditions under which a probe will hybridize to its target subsequence, typically in a complex mixture of nucleic acid, but to no other sequences. Stringent conditions are sequence-dependent and will be different in different circumstances. Longer sequences hybridize specifically at higher temperatures. An extensive guide to the hybridization of nucleic acids is found in Tijssen, Techniques in Biochemistry and Molecular Biology-Hybridization with Nucleic Probes, "Overview of principles of hybridization and the strategy of nucleic acid assays" (1993). Generally, stringent conditions are selected to be about 5-10° C. lower than the thermal melting point ($T_m$) for the specific sequence at a defined ionic strength pH. The $T_m$ is the temperature (under defined ionic strength, pH, and nucleic concentration) at which 50% of the probes complementary to the target hybridize to the target sequence at equilibrium (as the target sequences are present in excess, at $T_m$, 50% of the probes are occupied at equilibrium). Stringent conditions will be those in which the salt concentration is less than about 1.0 M sodium ion, typically about 0.01 to 1.0 M sodium ion concentration (or other salts) at pH 7.0 to 8.3 and the temperature is at least about 30° C. for short probes (e.g., 10 to 50 nucleotides) and at least about 60° C. for long probes (e.g., greater than 50 nucleotides). Stringent conditions may also be achieved with the addition of destabilizing agents such as formamide. For high stringency hybridization, a positive signal is at least two times background, preferably 10 times background hybridization. Exemplary high stringency or stringent hybridization conditions include: 50% formamide, 5×SSC and 1% SDS incubated at 42° C. or 5×SSC and 1% SDS incubated at 65° C., with a wash in 0.2×SSC and 0.1% SDS at 65° C. However, other high stringency hybridization conditions known in the art can be used.

Nucleic acids that do not hybridize to each other under stringent conditions are still substantially identical if the polypeptides that they encode are substantially identical. This occurs, for example, when a copy of a nucleic acid is created using the maximum codon degeneracy permitted by the genetic code. In such cases, the nucleic acids typically hybridize under moderately stringent hybridization conditions. Exemplary "moderately stringent hybridization conditions" include a hybridization in a buffer of 40% formamide, 1 M NaCl, 1% SDS at 37° C., and a wash in 1×SSC at 45° C. A positive hybridization is at least twice background. Those of ordinary skill will readily recognize that alternative hybridization and wash conditions can be utilized to provide conditions of similar stringency.

I. Introduction

Plant biotechnology has the potential to significantly improve agricultural crop productivity and utilization properties, and to facilitate production of novel products and optimize biomass for biofuels production. An important component in the implementation of biotechnological crop improvement is the use of various gene expression. Unfortunately, biotechnologists seeking to limit gene expression to non-seed tissues of genetically engineered cereal crops have only a few choices of well characterized organ-specific promoters. Thus, what is needed in the art are tissue and organ specific promoters that enable precise, localized expression of transgenes in biotechnology-derived crops and limit the potential of unintended impacts on plant physiology and the environment.

The rice Leaf Panicle 2 gene (LP2, Os02g40240) encodes a leucine-rich repeat (LRR)-receptor kinase-like protein that is strongly expressed in leaves and other photosynthetic tissues. Thus, the rice LP2 promoter is highly responsive to light and is therefore useful for controlling gene expression in the green tissues of plants. Indeed, as will be demonstrated hereinbelow, transgenic rice plants comprising an isolated rice LP2 promoter operably linked to a GUS::GFP bifunctional reporter gene display an organ-specific pattern of expression with strong β-glucuronidase (GUS) activity observed in histochemically stained mesophyll cells, as well as in other green tissues and leaf cell types including e.g., epidermal cells.

The LP2 promoter confers strong expression in leaf mesophyll cells, and uniquely, it also directs gene expression in multiple other cell types present in the leaf including e.g., the epidermal and vascular cells. This aspect of leaf cell type specificity distinguishes and broadens the usefulness of the LP2 promoter as a transgene expression control element relative to other available promoters. Thus, if expression is desired in leaf epidermal cells or the leaf vascular tissue (in addition to leaf mesophyll cells), for example to confer foliar disease resistance, the LP2 promoter provides organ-specific expression capability in those cells types.

Thus, in an exemplary embodiment the invention provides isolated rice LP2 promoter sequences which consist of a nucleic acid sequence that is at least about 90% identical to SEQ ID NO:3, or a segment or fragment thereof, wherein the promoter is capable of initiating transcription in a plant. In one exemplary embodiment, the segment or fragment of SEQ ID NO:3 is SEQ ID NO:2. In another exemplary embodiment, the segment or fragment of SEQ ID NO:3 is SEQ ID NO:1. In still another exemplary embodiment, the segment or fragment of SEQ ID NO:3 is SEQ ID NO:4.

In another exemplary embodiment, the isolated rice LP2 promoter is at least about 95% identical SEQ ID NO:3, or a segment or fragment thereof, wherein the promoter is capable of initiating transcription in a plant. In another exemplary embodiment, the isolated rice LP2 promoter has a nucleic acid sequence identical to SEQ ID NO:3.

In other exemplary embodiments the invention provides expression vectors comprising isolated rice LP2 promoter sequences, transgenic plants comprising isolated rice LP2 promoter sequences, and methods for expressing heterologous nucleic acids in plants, wherein the heterologous nucleic acid is operably linked to an isolated rice LP2 promoter sequence.

II. Isolating Rice LP2 Promoter Sequences and Constructing Expression Vectors

A. General Recombinant DNA Methods

This invention utilizes routine techniques in the field of recombinant genetics. Basic texts disclosing the general methods of use in this invention include Sambrook et al., Molecular Cloning—A Laboratory Manual (2nd Ed.), Vol. 1-3, Cold Spring Harbor Laboratory, Cold Spring Harbor, N.Y., 1989; Kriegler, Gene Transfer and Expression: A Laboratory Manual (1990); and Current Protocols in Molecular Biology (Ausubel et al., eds., 1994)). Unless otherwise noted, technical terms are used according to conventional usage. Definitions of common terms in molecular biology maybe found in e.g., Benjamin Lewin, Genes V, published by Oxford University Press, 1994 (ISBN 0-19-854287-9); Kendrew et al. (eds.), The Encyclopedia of Molecular Biology, published by Blackwell Science Ltd., 1994 (ISBN 0-632-02182-9); and Robert A. Meyers (ed.), Molecular Biology and Biotechnology: a Comprehensive Desk Reference, published by VCH Publishers, Inc., 1995 (ISBN 1-56081-569-8).

For nucleic acids, sizes are given in either kilobases (kb) or base pairs (bp). Estimates are typically derived from agarose or acrylamide gel electrophoresis, from sequenced nucleic acids, or from published DNA sequences. For proteins, sizes are given in kilodaltons (kDa) or amino acid residue numbers. Proteins sizes are estimated from gel electrophoresis, from sequenced proteins, from derived amino acid sequences, or from published protein sequences.

Oligonucleotides that are not commercially available can be chemically synthesized e.g., according to the solid phase phosphoramidite triester method first described by Beaucage & Caruthers, Tetrahedron Letts. 22:1859-1862 (1981), using an automated synthesizer, as described in Van Devanter et al., Nucleic Acids Res. 12:6159-6168 (1984). Purification of oligonucleotides is by either native acrylamide gel electrophoresis or by anion-exchange HPLC as described in Pearson & Reanier, J. Chrom. 255:137-149 (1983).

The sequence of the cloned genes and synthetic oligonucleotides can be verified after cloning using, e.g., the chain termination method for sequencing double-stranded templates of Wallace et al., Gene 16:21-26 (1981).

B. Methods for the Isolation of Nucleic Acids Comprising Isolated Rice LP2 Promoter Sequences Isolated rice LP2 promoters can be isolated using any of a variety of methods known to those of skill in the art which may be used for isolation of plant promoters. For example, isolated rice LP2 promoters can be isolated from genomic DNA fragments encoding a rice LP2 gene. The term "isolated rice LP2 gene" as used herein, refers to a plant genomic DNA molecule that comprises the entire isolated rice LP2 promoter region operably linked to the entire coding region (including exons and introns) for the rice Leaf Panicle 2 (LP2) protein and which may also include the adjacent 3' flanking region which encodes the 3' non-translated mRNA. Exemplary "isolated rice LP2 gene" is shown in FIG. 9. The term "isolated rice LP2 gene fragment" or "isolated rice LP2 gene fragment" refers to a portion of the isolated rice LP2 gene which is less than the entire promoter and coding regions of the gene. An isolated rice LP2 gene fragment may comprise a promoter region operably linked to a portion of the coding region of the gene. An exemplary "isolated rice LP2 gene fragment" is shown in FIG. 3. Genomic fragments encoding isolated rice LP2 genes and isolated rice LP2 gene fragments can be prepared as disclosed below.

In an exemplary embodiment, the nucleic acid sequences comprising isolated rice LP2 promoter sequences and related nucleic acid sequences are cloned from genomic DNA libraries using labeled oligonucleotide probes. In another exemplary embodiment, the nucleic acid sequences comprising isolated rice LP2 promoter sequences and related nucleic acid sequences are cloned from genomic DNA libraries using amplification techniques and labeled oligonucleotide primers.

In an exemplary embodiment, isolated rice LP2 promoters having organ or tissue-specific expression are identified using transcript profiling approaches to examine gene expression. Transcript profiling is known in the art (see e.g., J. D. Hoheisel (2006) Nature Reviews Genetics 7, 200-210). In an exemplary embodiment, transcripts identified using transcript profiling are used to design PCR primers for amplification and identification of full length isolated rice LP2 gene cDNAs.

Isolated rice LP2 promoter sequences typically comprise sequences that are identical to, or show substantial sequence identity (as defined above) to SEQ ID NO:2 and consist of a nucleotide sequence according to SEQ ID NO:3 or segment or fragment thereof. Thus, in exemplary embodiments, an isolated rice LP2 promoter sequence is a member selected from the group consisting of SEQ ID NO:1, SEQ ID NO:2, SEQ ID NO:3, SEQ ID NO:4 variants thereof, and fragments thereof. In another exemplary embodiment, variants of isolated rice LP2 promoters have at least about 80% sequence identity, at least about 85% sequence identity or at least about 90%, 90%, 91%, 92%, 93%, 94%, 95%, 96%, 97%, 98%, 99%, or 100%, sequence identity to SEQ ID NO:2 and consist of a nucleotide sequence according to SEQ ID NO:3 or segment or fragment thereof. In still other exemplary embodiments variants of isolated rice LP2 promoters comprise deletion mutations that remove some or all of nucleotides comprising the intron or alternatively spliced intron as illustrated in FIG. 1.

Thus, isolated rice LP2 promoter sequences typically hybridize to SEQ ID NO:2 under stringent hybridization conditions.

To prepare a genomic library, typically DNA is extracted from plant tissue and either mechanically sheared or enzymatically digested to yield fragments of about 15-20 kb. The fragments are then separated by gradient centrifugation from undesired sizes and are constructed in bacteriophage lambda vectors. These vectors and phage are packaged in vitro, as described e.g., in Sambrook, et al. supra. Recombinant phage are analyzed by plaque hybridization as described in Benton and Davis, Science, 196:180-182 (1977). Colony hybridization is carried out as generally described in M. Grunstein et al. Proc. Natl. Acad. Sci. USA., 72:3961-3965 (1975). DNA encoding plant isolated rice LP2 genes and/or isolated rice LP2 gene fragments is identified in genomic libraries by its ability to hybridize with labeled nucleic acid probes that comprise isolated rice LP2 promoter sequences, e.g., on Southern blots. The hybridizing DNA regions are isolated by standard methods familiar to those of skill in the art. See e.g., Sambrook, et al. supra.

In an exemplary embodiment, isolated rice LP2 promoter sequences are isolated by screening plant DNA libraries with labeled oligonucleotide probes having sequences derived from of the DNA sequence of japonica isolated rice LP2 promoter shown in FIG. 2, SEQ ID NO:2.

Other methods known to those of skill in the art can also be used to isolate plant DNA fragments comprising isolated rice LP2 promoters. See e.g., Sambrook, et al. for a description of other techniques for the isolation of DNAs related to DNA molecules of known sequence.

In exemplary embodiments, deletion analysis and a promoterless reporter gene (e.g., GUS) are used to identify those regions which can drive expression of a structural gene. Sequences characteristic of promoter sequences can also be used to identify the promoter. Indeed, sequences controlling eukaryotic gene expression have been extensively studied. For instance, promoter sequence elements include the TATA box consensus sequence (TATAAT), which is usually 20 to 30 base pairs upstream of the transcription start site. In plants, further upstream from the TATA box, at positions −80 to −100, there is typically a promoter element with a series of adenines surrounding the trinucleotide G (or T) N G, see e.g., J. Messing et al., (1983) in Genetic Engineering in Plants, pp. 221-227 Kosage, Meredith and Hollaender, eds.

However, typically, isolated rice LP2 promoters do not contain a match for the TATA box consensus sequence CTATAWAWA, where W=A or T (Civan and Svec, (2009) Genome 52, 294-297). Instead, isolated rice LP2 promoters comprise a T/A-rich sequence from −31 to −24 bp upstream of the transcription start site, the typical location of a TATA box (see e.g., FIG. 1). Furthermore, isolated rice LP2 promoters typically comprise a "Y patch" (C/T pyrimidine-rich sequence at +97 to +108, FIG. 1), a feature that is present in the 5' UTR of many rice transcripts (Civan and Svec, 2009, supra).

Another typical feature of isolated rice LP2 promoters is a 353 bp directly repeated sequence (FIG. 1). The two repeat sequences are 93% identical and A+T rich (70% A+T), but do not match other sequences in the rice genome and are not transposon-derived repeat elements.

Once a putative isolated rice LP2 promoter sequence is identified, it can be tested for promoter activity, e.g, tested for the ability to direct transcription of an operably linked nucleic acid sequence in plants, in a tissue-specific manner characteristic of an isolated rice LP2 promoter. Methods for testing the activity of promoters and putative promoters in plant cells are known in the art see e.g., L. Szabados et al. (1995) Molecular Breeding 1(4):419-423 and Y. Yang et al. (2000) The Plant Journal, 22(6): 543-551.

In one exemplary embodiment, plant promoters are characterized in vivo by generating a transgenic plant which comprises an expression vector comprising a putative promoter operably linked to a heterologous nucleic acid that acts as a reporter gene e.g., a nucleic acid encoding GUS activity. The transgenic plant is then evaluated for expression of the reporter gene.

In another exemplary embodiment, Agrobacterium mediated transient transfection is used to assay promoter activity see e.g., Y. Yang et al. (2000) supra. As is known in the art Agrobacterium mediated transient transfection provides a reliable transient expression assay. Typically, a binary expression vector comprising a putative promoter and an operably linked heterologous reporter gene e.g., GUS, is introduced into an appropriate Agrobacterium strain, and the resulting Agrobacterium is used to mediate transient transformation in planta, and activity of the reporter gene, e.g., GUS is evaluated by methods well known in the art.

In another exemplary embodiment, ballistic transient transformation of plant cells or organs is used to analyse plant promoter activity (see e.g., Baum, K., et al. (1997). Plant J. 12, 463-469). In still another exemplary embodiment, promoter activity is tested by observing the ability of a nucleic acid sequence to drive the expression of green florescent protein see e.g., Harper, B. K. and Stewart JR. C. N. (2000) Plant Molecular Biology Reporter 18: 141a-141i; and Moseyko, N & L. J. Feldman (2001) Plant, Cell and Environment 24, 557-563.

Thus, sequences isolated from genomic libraries (or any other source) by virtue of their ability to hybridize to isolated rice LP2 promoter sequences, can be tested for promoter activity by methods known in the art.

Sequence Features of Isolated Rice LP2 Promoter Sequences

The full length isolated rice LP2 cDNA gene from japonica rice typically comprises about 3475 nucleotides. However, a shorter cDNA derived from an alternatively spliced LP2 transcript is also found. This alternatively spliced cDNA is about 3420 nucleotides. A full length isolated rice LP2 promoter comprising the 5' regulatory sequences is also shown as SEQ ID NO:1 in FIG. 1 and as SEQ ID NO:3 in FIG. 3.

In one exemplary embodiment, an isolated rice LP2 promoter sequence controls transcription of heterologous nucleic acids in transgenic plants and transgenic plant cell lines wherein the transgenic plant or plant cell line comprise a heterologous nucleic acid operably linked to an isolated rice LP2 promoter as shown in SEQ ID NO:1, and FIG. 1. In another exemplary embodiment, isolated rice LP2 promoter sequence, wherein the alternatively spliced intron has been deleted, is shown in FIG. 4 as SEQ ID NO:4 [controls transcription of heterologous nucleic acids in transgenic plants and transgenic plant cell lines wherein the transgenic plant or plant cell line comprises a heterologous nucleic acid operably linked to an isolated rice LP2 promoter sequence, wherein the alternatively spliced intron has been deleted.

Various modifications can be made to the isolated rice LP2 promoters disclosed herein to provide promoters with different properties (e.g., tissue specificity, promoter strength, and the like). In an exemplary embodiment, truncated forms of an isolated rice LP2 promoter are constructed by mapping restriction enzyme sites in the promoter and then using the constructed map to determine appropriate restriction enzyme cleavage to excise a subset of the sequence. In an exemplary embodiment, modified promoters are inserted into a suitable vector and tested for their ability to drive expression of a marker gene. Tissue specificity of the modified promoters can be tested in regenerated plants.

Tissue Specific Expression of Operably Linked Nucleic Acids

Isolated rice LP2 promoters are highly responsive to light. Thus, in one exemplary embodiment, an isolated rice LP2 promoter drives tissue specific expression of an operably linked gene in photosynthetic tissues of a plant. As noted above, rice LP2 promoters confer strong expression in leaf mesophyll cells. Rice LP2 promoters also direct gene expression in other leaf cell types including e.g., the epidermal and vascular cells. Thus, in exemplary embodiments an isolated rice LP2 promoter controls transgene expression in leaf epidermal cells or the leaf vascular tissue. Thus, in some exemplary embodiments, a rice LP2 promoter is operably linked to a nucleotide sequence that encodes a protein or nucleic acid that confers foliar disease resistance, and the operably linked nucleotide sequence is expressed in leaf epidermal cells or leaf vascular tissue thereby conferring foliar disease resistance.

In other exemplary embodiments, light sensitive isolated rice LP2 promoter sequences are operably linked to photosynthetic genes or gene fragments, and transformed into plants. Expression of the photosynthetic genes or gene fragments under control of the rice LP2 promoter sequence enhances photosynthetic capacity of the transformed plant thereby increasing the productivity of the transformed plant.

C. Construction of Vectors Comprising Isolated Rice LP2 Promoter Sequences

Once an isolated rice LP2 promoter region has been isolated, various methods may be used to construct expression cassettes, vectors and other DNA constructs. Expression cassettes comprising isolated rice LP2 promoter sequence can be constructed in a variety of ways. The skilled artisan is well aware of the genetic elements that must be present on an expression construct/vector in order to successfully transform, select and propagate the expression construct in host cells. Techniques for manipulation of nucleic acids encoding plant isolated rice LP2 promoter sequences such as subcloning nucleic acid sequences into expression vectors, labeling probes, DNA hybridization, and the like are described generally in Sambrook, et al., supra.

In an exemplary embodiment, an isolated rice LP2 promoter sequence and a heterologous DNA sequence encoding a desired gene product are cloned into an expression vector via suitable restriction endonuclease sites such that the promoter is upstream of and in-frame with the DNA sequence. In another exemplary embodiment, various procedures, such as site directed mutagenesis are used to introduce a restriction site in an isolated rice LP2 promoter sequence. In another exemplary embodiment, various procedures, such as site directed mutagenesis are used to introduce a restriction site into heterologous DNA sequence such that the sequence can be cloned into an expression vector downstream and in-frame with the isolated rice LP2 promoter sequence. Thus, heterologous DNA sequences can be linked to the isolated rice LP2 promoter such that the expression of the heterologous sequences is controlled by the isolated rice LP2 promoter.

DNA constructs comprising an isolated rice LP2 promoter operably linked to heterologous DNA sequences can be inserted into a variety of vectors (e.g., pGPro1, see e.g., Thilmony et al. (2006) *Plant Mol. Biol. Rep.* 24, 57-69).

Typically, the vector chosen is an expression vector that is useful in the transformation of plants and/or plant cells. The expression vector may be a plasmid, virus, cosmid, artificial chromosome, nucleic acid fragment, or the like. Such vectors can be constructed by the use of recombinant DNA techniques well known to those of skill in the art. The expression vector comprising an isolated rice LP2 promoter sequence may then be transfected/transformed into the target host cells. Successfully transformed cells are then selected based on the presence of a suitable marker gene as disclosed below.

A number of recombinant vectors are available to those of skill in the art for use in the stable transfection of plant cells or for the establishment of transgenic plants (see e.g., Weissbach and Weissbach, (1989) *Methods for Plant Molecular Biology*, Academic Press; Gelvin et al., (1990) *Plant Molecular Biology Manual; Genetic Engineering of Plants, an Agricultural Perspective*, A. Cashmore, Ed.; Plenum: NY, 1983; pp 29 38; Coruzzi, G. et al., The Journal of Biological Chemistry, 258: 1399 (1983); and Dunsmuir, P. et al., Journal of Molecular and Applied Genetics, 2:285 (1983). As is known in the art, the choice of a vector is influenced by the method that will be used to transform host plants, and appropriate vectors are readily chosen by one of skill in the art. In an exemplary embodiment, known vectors are used to create expression constructs comprising isolated rice LP2 promoter sequences.

Typically, plant transformation vectors include one or more cloned plant genes (or cDNAs) operably linked to promoter sequences, e.g., isolated rice LP2 promoter sequences, and a selectable marker. Such plant transformation vectors also typically include a transcription initiation start site, a heterologous nucleic acid the control of whose expression is desired, a ribosome binding site, an RNA processing signal, a transcription termination site, and/or a polyadenylation signal.

In some exemplary embodiments, plant transformation vectors may also include additional regulatory sequences from the 3'-untranslated region of plant genes, e.g., a 3' terminator region to increase mRNA stability of the mRNA, such as the PI-II terminator region of potato or the octopine or nopaline synthase (NOS) 3' terminator regions.

(i) Regulatory Elements

In addition to an isolated rice LP2 promoter or a derivative thereof, expression constructs prepared as disclosed may comprise additional elements. In an exemplary embodiment, expression constructs comprising an isolated rice LP2 promoter operably linked to a heterologous coding region also comprise an enhancer sequence such that the expression of the heterologous protein may be enhanced. As is known in the art, enhancers are typically found 5' to the start of transcription, they can often be inserted in the forward or reverse orientation, either 5' or 3' to the coding sequence. In one exemplary embodiment, the intron region of an isolated rice LP2 promoter (see e.g., FIG. 1 showing SEQ ID NO:1) comprises an enhancer sequence. In one exemplary embodiment, isolated rice LP2 promoter sequences are operably linked to a coding sequence in the sense orientation, such that expression with the isolated rice LP2 promoter produces the respective sense strand RNA.

In some exemplary embodiments, isolated rice LP2 promoter sequences are operably linked to a coding sequence in antisense orientation, such that accumulation of the respective protein encoded by the sense transcript is eliminated or decreased upon expression with the isolated rice LP2 promoter.

(ii) Terminators

Expression constructs prepared as disclosed herein typically include a sequence that acts as a signal to terminate transcription and allow for the poly-adenylation of the mRNA produced by coding sequences operably linked to the isolated rice LP2 promoter. Termination sequences are typically located in the 3' flanking sequence of a coding sequence, which will typically comprise the proper signals for transcription termination and polyadenylation. Thus, in an exemplary embodiment, termination sequences are ligated into the expression vector 3' of the heterologous coding sequences to provide polyadenylation and termination of the mRNA. Terminator sequences and methods for their identification and isolation are known to those of skill in the art, see e.g., Albrechtsen, B. et al. (1991) Nucleic Acids Res. April 25; 19(8): 1845-1852, and WO/2006/013072. In one exemplary embodiment, the transcription termination sequences comprising the expression constructs, are associated with known genes from the host organism.

(iii) Marker Genes

As noted above, plant transformation vectors typically include a selectable and/or screenable marker gene to allow for the ready identification of transformants. Exemplary selectable marker genes include, but are not limited to those encoding antibiotic resistance (e.g. resistance to hygromycin, kanamycin, bleomycin, G418, streptomycin or spectinomycin) and herbicide resistance genes (e.g., phosphinothricin acetyltransferase). Exemplary screenable markers include e.g., green florescent protein.

In an exemplary embodiment, a selectable or screenable marker gene is employed as, or in addition to, a particular gene of interest, to provide or enhance the ability to identify transformants. As is known in the art, "marker genes" are genes that impart a distinct phenotype to cells expressing the marker gene, such that transformed cells can be distinguished from cells that do not have the marker. In one exemplary embodiment, marker genes encode a selectable marker which one can "select" for by chemical means, e.g., through the use of a selective agent (e.g., a herbicide, antibiotic, or the like). In another exemplary embodiment, marker genes encode a screenable marker, which is identified through observation or testing, e.g., by "screening" (e.g., the green fluorescent protein).

Numerous selectable marker genes are known to the art. Some exemplary selectable markers are disclosed in e.g., Potrykus et al., (1985) Mol. Gen. Genet., 199:183-188; Stalker et al., (1988) Science, 242:419 422; Thillet et al., (1988) J. Biol. Chem., 263:12500 12508; Thompson et al., (1987), EMBO J. 6:2519-2523; Deblock et al. (1987), EMBO J. 6:2513-2518; U.S. Pat. No. 5,646,024; U.S. Pat. No. 5,561,236; U.S. Patent application Publication 20030097687; and Boutsalis, P., and Powles, S. B. (1995) Weed Research 35: 149-155.

Some exemplary screenable markers include, but are not limited to a β-glucuronidase (GUS) or uidA gene, see e.g., U.S. Pat. No. 5,268,463, U.S. Pat. No. 5,432,081 and U.S. Pat. No. 5,599,670; a β-gene, see e.g., Sutcliffe, (1978) Proc. Natl. Acad. Sci. USA, 75:3737-3741); β-galactosidase; and luciferase (lux) gene (see e.g., Ow et al., (1986) Science, 234:856-859; Sheen et al., (1995) Plant J., 8(5):777-784; and WO 97/41228).

Exemplary selectable or screenable marker genes also include genes which encode a "secretable marker" whose secretion can be detected as a means of identifying or selecting for transformed cells. Exemplary secretable markers include but are not limited to secretable antigens that can be identified by antibody interaction, e.g., small, diffusible proteins detectable, e.g., by ELISA; and/or secretable enzymes which can be detected by their catalytic activity. E.g., small active enzymes detectable in extracellular solution (e.g., α-amylase, β-lactamase, phosphinothricin acetyltransferase); and proteins that are inserted or trapped in the cell wall (e.g., proteins that include a leader sequence such as that found e.g., in the expression unit of extensin or tobacco PR-S).

The choice of a particular marker gene is readily made by the skilled practitioner according to the needs and considerations of the particular application or use.

(iv) Other Vector Components

In some exemplary embodiments, an expression vector further comprises sequences that are joined to the coding sequence of an expressed heterologous nucleic acid, which are removed post-translationally from the initial translation product. In one exemplary embodiment, post-translationally removed sequences facilitate the transport of the protein into or through intracellular or extracellular membranes, thereby facilitating the transport of the protein into compartments inside and/or outside the cell. In an exemplary embodiment, post-translationally removed sequences protect a nascent protein from intracellular proteolytic degradation. In one exemplary embodiment, a nucleic acid segment encoding a leader peptide sequence upstream and in reading frame with a selected coding sequence is used in recombinant expression of the coding sequence in a host cell.

In another exemplary embodiment, an expression construct comprises a bacterial origin of replication, e.g., a colE1 origin. In still another exemplary embodiment, an expression construct/vector comprises a bacterial selectable marker e.g., an ampicillin, tetracyclin, hygromycin, neomycin or chloramphenicol resistance gene.

As is well known in the art, expression constructs typically comprise restriction endonuclease sites to facilitate vector construction. Exemplary restriction endonuclease recognition sites include, but are not limited to recognition site for the restriction endonucleases NotI, AatII, SacII, PmeI HindIII, PstI, EcoRI, and BamHI.

D. Plant Hosts, Plant Transformation and Plant Selection and Regeneration Techniques DNA constructs comprising an isolated rice LP2 promoter operably linked to a heterologous DNA sequence can be used to transform plant cells and produce transgenic plants with desired phenotypic characteristics.

Exemplary plants for transformation with expression constructs comprising isolated rice LP2 promoter sequences include, but are not limited to; dicotyledonous species, such as e.g., tobacco (*Nicotiana* spp.), tomato (*Solanum* spp.), potato (*Solanum* spp.), hemp (*Cannabis* spp.), sunflower (*Helianthus* spp.), sorghum (*Sorghum vulgare*), wheat (*Triticum* spp.), maize (*Zea mays*), rice (*Oryza sativa*), rye (*Secale cereale*), oats (*Avena* spp.), barley (*Hordeum vulgare*), rapeseed (*Brassica* spp.), broad bean (*Vicia faba*), french bean (*Phaseolus vulgaris*), other bean species (*Vigna* spp.), lentil (*Lens culinaris*), soybean (*Glycine max*), arabidopsis (*Arabidopsis thaliana*), guayule (*Parthenium argentatum*), cotton (*Gossypium hirsutum*), petunia (*Petunia hybrida*), flax (*Linum usitatissimum*), and carrot (*Daucus carota sativa*).

Transformation and regeneration of monocotyledonous and dicotyledonous plant cells is well known in the art, see e.g., Weising et al. Ann. Rev. Genet. 22:421-477 (1988); U.S. Pat. No. 5,679,558; *Agrobacterium Protocols* Kevan M. A. Gartland ed. (1995) Humana Press Inc. and Wang, M., et al. (1998) Acta Hort. (ISHS) 461:401-408. The choice of method varies with the type of plant to be transformed, the particular application and/or the desired result. The appropriate transformation technique is readily chosen by the skilled practitioner.

Exemplary transformation/transfection methods available to those skilled in the art include, but are not limited to: direct uptake of foreign DNA constructs (see e.g., EP 295959); techniques of electroporation (see e.g., Fromm et al., (1986) Nature (London) 319:791) high-velocity ballistic bombardment with metal particles coated with the nucleic acid constructs (see e.g., Kline et al., Nature (London) 327:70 (1987), and U.S. Pat. No. 4,945,050); methods to transform foreign genes into commercially important crops, such as rapeseed (see De Block et al., Plant Physiol. 91:694 701 (1989)), sunflower (Everett et al., Bio/Technology 5:1201 (1987)), soybean (McCabe et al., Bio/Technology 6:923 (1988); Hinchee et al., Bio/Technology 6:915 (1988); Chee et al., Plant Physiol. 91:1212 1218 (1989); Christou et al., Proc. Natl. Acad. Sci. USA 86:7500 7504 (1989); EP 301749), rice (Hiei et al., Plant J. 6:271 282 (1994)), corn (Gordon-Kamm et al., Plant Cell 2:603 618 (1990); Fromm et al., Biotechnology 8:833 839 (1990)), and Hevea (Yeang, H. Y., et al., In, Engineering Crop Plants for Industrial End Uses. Shewry, P. R., Napier, J. A., David, P. J., Eds.; Portland: London, 1998; pp 55 64). Other known methods are disclosed in e.g., U.S. Pat. Nos. 5,597,945; 5,589,615; 5,750,871; 5,268,526; 5,262,316; and 5,569,831.

Another exemplary method includes: transformation with DNA employing *Agrobacterium tumefaciens* or *Agrobacterium rhizogenes* as the transforming agent, electroporation, particle acceleration, etc. (see, e.g., EP 295959 and EP 138341). In one exemplary embodiment, Ti-derived vectors are used to transform a wide variety of higher plants, including dicotyledonous plants, such as e.g., potato, soybean, cotton, rape, tobacco, and rice (see e.g., Pacciofti et al., Bio/Technology 3:241 (1985); Byme et al., Plant Cell, Tissue and Organ Culture 8:3 (1987); Sukhapinda et al., Plant Mol. Biol. 8:209 216 (1987); Lorz et al., Mol. Gen. Genet. 199:178 (1985); Potrykus, (1985) supra; Park et al., J. Plant Biol. 38(4):365 71 (1995); and Hiei et al., Plant J. 6:271 282 (1994)).

*Agrobacterium tumefaciens*-meditated transformation techniques are well described in the scientific literature. See, e.g., Horsch et al. Science (1984) 233:496-498, and Fraley et al. (1983) Proc. Natl. Acad. Sci. USA 80:4803. Typically, a plant cell, an explant, a meristem or a seed is infected with *Agrobacterium tumefaciens* transformed with the expression vector/construct which comprises an isolated rice LP2 promoter sequence. Under appropriate conditions known in the art, the transformed plant cells are grown to form shoots, roots, and develop further into plants. The nucleic acid segments can be introduced into appropriate plant cells, for example, by means of the Ti plasmid of *Agrobacterium tumefaciens*. The Ti plasmid is transmitted to plant cells upon infection by *Agrobacterium tumefaciens*, and is stably integrated into the plant genome (Horsch et al., (1984) "Inheritance of Functional Foreign Genes in Plants," Science, 233: 496-498; Fraley et al., (1983) Proc. Nat'l. Acad. Sci. U.S.A. 80:4803.

All plant cells which can be transformed by *Agrobacterium* and whole plants regenerated from the transformed cells can also be transformed so as to produce transformed whole plants which contain the transferred expression vector/construct which comprises an isolated rice LP2 promoter sequence.

There are various ways to transform plant cells with *Agrobacterium*, including:
 (1) co-cultivation of *Agrobacterium* with cultured isolated protoplasts,
 (2) transformation of cells or tissues with *Agrobacterium*, or
 (3) transformation of seeds, apices or meristems with *Agrobacterium*.

Method (1) requires an established culture system that allows culturing protoplasts and plant regeneration from cultured protoplasts. Method (2) requires (a) that the plant cells or tissues can be transformed by *Agrobacterium* and (b) that the transformed cells or tissues can be induced to regenerate into whole plants. Method (3) requires micropropagation.

In the binary system, to have infection, two plasmids are needed: a T-DNA containing plasmid and a vir plasmid. Any one of a number of T-DNA containing plasmids can be used, the only requirement is that one be able to select independently for each of the two plasmids.

After transformation of the plant cell or plant, those plant cells or plants transformed by the Ti plasmid so that the desired DNA segment is integrated can be selected by an appropriate phenotypic marker. These phenotypic markers include, but are not limited to, antibiotic resistance, herbicide resistance or visual observation. Other phenotypic markers are known in the art and may also be used.

Transformed plant cells which are derived by any of the above transformation techniques can be cultured to regenerate a whole plant which possesses the desired transformed phenotype. Such regeneration techniques rely on manipulation of certain phytohormones in a tissue culture growth medium, typically relying on a biocide and/or herbicide marker which has been introduced together with the desired nucleotide sequences. Plant regeneration from cultured protoplasts is described in Evans et al., Protoplasts Isolation and Culture, Handbook of Plant Cell Culture, pp. 124-176, MacMillan Publishing Company, New York, 1983; and Binding, Regeneration of Plants, Plant Protoplasts, pp. 21-73, CRC Press, Boca Raton, 1985, all of which are incorporated herein by reference. Regeneration can also be obtained from plant callus, explants, organs, or parts thereof. Such regeneration techniques are described generally in Klee et al. Ann. Rev. of Plant Phys. 38:467-486 (1987).

One of skill will recognize that, after an expression cassette comprising isolated rice LP2 promoter sequences is stably incorporated in transgenic plants and confirmed to be operable, it can be introduced into other plants by sexual crossing. Any of a number of standard breeding techniques can be used, depending upon the species to be crossed.

The skilled artisan will recognize that different independent transformation events will result in different levels and patterns of expression (Jones et al., EMBO J. 4:2411 2418 (1985); De Almeida et al., Mol. Gen. Genetics 218:78 86 (1989)), and thus that multiple events will likely need to be screened in order to obtain lines displaying the desired expression level and pattern. Exemplary method for screening transformation events may be accomplished e.g., by Southern analysis of DNA blots (Southern, (1975) J. Mol. Biol. 98: 503), Northern analysis of mRNA expression (Kroczek, J., (1993) Chromatogr. Biomed. Appl., 618(1 2): 133 145), Western analysis of protein expression, and/or phenotypic analysis e.g., resistance to an herbicide can be detected by treatment with the herbicide. Expression of the heterologous DNA can also be detected by measurement of the specific RNA transcription product. This can be done by, for example, RNAse protection or Northern blot procedures. If heterologous DNA sequences encode a novel protein, the protein product may be assayed, for instance, by its function or by a variety of immunoassay techniques. Alternatively, a novel protein product with enzymatic activity can be measured in an enzyme assay. In another exemplary embodiment, protein expression is quantitated and/or detected in different plant tissues using a reporter gene, e.g., GUS.

Once transgenic plants have been obtained, they may be grown to produce plant tissues or parts having the desired phenotype. The plant tissue or plant parts may be harvested, and/or the seed collected. The seed may serve as a source for growing additional plants with tissues or parts having the desired characteristics.

E. Expression of Heterologus Nucleic Acids in Transformed Plants

The introduction of expression vectors into plants and plant cells as disclosed herein is useful for the introduction of one or more new traits to a host plant cell. There are a variety of different approaches one can use to produce a desired phenotype in transgenic plants. In an exemplary embodiment, using methods described herein, one can operably link a heterologous gene to an isolated rice LP2 promoter sequence and transform plant cells. Transgenic plants can be produced from the transformed plant cells so that the heterologous gene product is produced in certain tissues (e.g., photosynthetic tissues, e.g., leaves) of a transgenic plant. In this context, the term "heterologous gene" refers to a gene that is not normally present in a plant or which, if present, is not normally expressed in a particular plant cell tissue. The expression of the gene can result in the production of a protein that confers an altered phenotype on a transgenic plant. In some exemplary embodiments, an isolated rice LP2 promoter sequence operably linked to a heterologous gene is used to create transgenic plants in which heterologous nucleic acid sequences are expressed at higher or lower levels than normal. In another exemplary embodiment a heterologous nucleic acid operably linked to isolated rice LP2 promoter sequences, is introduced into a transgenic plant to modify the rate, timing, amount and/or quality of the expression of the heterologous nucleic acid.

A variety of genes capable of altering a plant phenotype can be expressed under control of isolated rice LP2 promoter sequences. Suitable genes include, but are not limited to: genes for herbicide resistance; genes for fungal disease resistance (e.g., chitinases and glucanases); genes for bacterial disease resistance (e.g., cecropins); and genes for insect resistance (e.g., *B. thuringiensis* toxin). Since, in some exemplary embodiments, an isolated rice LP2 promoter sequence provides light-regulated as well as general expression, genes affecting leaf development or photosynthesis could also be usefully expressed. For example, in an exemplary embodiment, an isolated rice LP2 promoter sequence is operably linked to, e.g., genes for photosynthesis; genes for the expression of anthocyanin or other pigmentation. In some exemplary embodiments, a plant expressing a pigment or anthocyanin gene under control of an isolated rice LP2 promoter is useful for creating new varieties of colorful houseplants and/or other nursery stocks.

In other exemplary embodiments, an isolated rice LP2 promoter sequence is operably linked to a gene functional in pest resistance. A plant expressing a pest resistance gene under control of an isolated rice LP2 promoter is useful for creating new varieties of plants that are able to increase their ability to ward off pests, in response to attack by a pest.

One of skill will recognize that proteins have different domains which perform different functions. Thus, gene sequences operably linked to an isolated rice LP2 promoter sequence need not be full length, so long as the desired functional domain of the protein is expressed. Modified protein chains can also be readily designed utilizing various recombinant DNA techniques well known to those skilled in the art. For example, the chains can vary from the naturally occurring sequence at the primary structure level by amino acid substitutions, additions, deletions, and the like. These modifications can be used in a number of combinations to produce the final modified protein chain.

DNA constructs containing an isolated rice LP2 promoter sequence operably linked to a heterologous DNA sequence can also be used in a number of techniques to suppress expression of endogenous plant genes, e.g., sense or antisense suppression. In antisense technology, a nucleic acid segment from the desired plant gene is cloned and operably linked to an isolated rice LP2 promoter sequence such that the antisense strand of RNA will be transcribed. The construct is then transformed into plants and the anti-sense strand of RNA is produced. In plant cells, it has been shown that anti-sense RNA inhibits gene expression; see, e.g., Sheehy et al., Proc. Nat. Acad. Sci. USA, 85:8805-8809 (1988), and Hiatt et al., U.S. Pat. No. 4,801,340 which are incorporated herein by reference.

The nucleic acid segment to be introduced in antisense suppression generally will be substantially identical to at least a portion of the endogenous gene or genes to be repressed, but need not be identical. The vectors of the present invention can be designed such that the inhibitory effect applies to other proteins within a family of genes exhibiting homology or substantial homology to the target gene. Segments from a gene can be used (1) directly to inhibit expression of homologous genes in different plant species, or (2) as a means to obtain the corresponding sequences, which can be used to suppress the gene.

The introduced sequence also need not be full length relative to either the primary transcription product or fully processed mRNA. Generally, higher homology can be used to compensate for the use of a shorter sequence. Furthermore, the introduced sequence need not have the same intron or exon pattern, and homology of non-coding segments will be equally effective. Normally, a sequence of between about 30 or 40 nucleotides and about 2,000 nucleotides is used, though in some exemplary embodiments a sequence of at least about 100 nucleotides is used. In other exemplary embodiments, a sequence of at least about 200 nucleotides is used, and in still other exemplary embodiments, a sequence of at least about 500 nucleotides is used.

In an exemplary embodiment catalytic RNA molecules are expressed under control of an isolated rice LP2 promoter sequence. Catalytic RNA molecules or ribozymes also have been reported to have use as a means to inhibit expression of endogenous plant genes. It is possible to design ribozymes that specifically pair with virtually any target RNA and cleave the phosphodiester backbone at a specific location, thereby functionally inactivating the target RNA. In carrying out this cleavage, the ribozyme is not itself altered, and is thus capable of recycling and cleaving other molecules, making it a true enzyme. The inclusion of ribozyme sequences within antisense RNAs confers RNA-cleaving activity upon them, thereby increasing the activity of the constructs.

A number of classes of ribozymes have been identified. One class of ribozyme is derived from a number of small circular RNAs which are capable of self-cleavage and replication in plants. The RNAs replicate either alone (viroid RNAs) or with a helper virus (satellite RNAs). Examples include RNAs from avocado sunblotch viroid and the satellite RNAs from tobacco ringspot virus, lucerne transient streak virus, velvet tobacco mottle virus, solanum nodiflorum mottle virus and subterranean clover mottle virus. The design and use of target RNA-specific ribozymes is disclosed in e.g., Haseloff et al. Nature, 334:585-591 (1988).

An exemplary method of suppression is sense suppression. Introduction of a nucleic acid configured in the sense orientation has been shown to be an effective means by which to block the transcription of target genes. For examples of the use of this method to modulate expression of endogenous genes see, Napoli et al., The Plant Cell 2:279-289 (1990), and U.S. Pat. No. 5,034,323. In an exemplary embodiment, sense suppression is used as a method for ripening control (e.g., Acc oxidase or Acc synthase), sweetness control (e.g., ADPG pyrophosphorylase), or color modification (e.g., chalcone synthase); see e.g., U.S. Pat. No. 5,034,323.

Generally, in sense suppression, some transcription of the introduced sequence occurs. The effect may also occur where the introduced sequence contains no coding sequence per se, but only intron or untranslated sequences homologous to sequences present in the primary transcript of the endogenous sequence. The introduced sequence generally will be substantially identical to the endogenous sequence intended to be repressed. This minimal identity will typically be greater than about 65%, but a higher identity is useful to exert a more effective repression of expression of the endogenous sequences. Substantially greater identity of more than about 80% is preferred, though about 95% to absolute identity would be most preferred. The effect may be applied to other proteins within a similar family of genes exhibiting homology or substantial homology. Segments from a gene can be used (1) directly to inhibit expression of homologous genes in different plant species, or (2) as a means to obtain the corresponding sequences, which can be used to suppress the gene.

In sense suppression, the introduced sequence whose expression is under transcriptional control of an isolated rice LP2 promoter sequence, needing less than absolute identity, also need not be full length, relative to either the primary transcription product or fully processed mRNA. A higher identity in a shorter than full length sequence compensates for a longer, less identical sequence. Furthermore, the introduced sequence need not have the same intron or exon pattern, and identity of non-coding segments may be equally effective. A sequence of a size of at least 50 base pairs is preferred, with greater length sequences being more preferred; see U.S. Pat. No. 5,034,323.

In one exemplary embodiment, the heterologous nucleic acid sequences under regulatory control of the isolated rice LP2 promoter sequences are constitutively expressed. In another exemplary embodiment, heterologous nucleic acid sequences under regulatory control of the isolated rice LP2 promoter sequences are induced. In still another exemplary embodiment, the heterologous nucleic acid sequences under regulatory control of the isolated rice LP2 promoter sequences which are induced are upregulated. In another exemplary embodiment, the heterologous nucleic acid sequences under regulatory control of isolated rice LP2 promoter sequences are upregulated in response to wounding.

The increase in transgene expression in response to injury (see e.g., FIGS. 8 A, and B), provides a means for minimizing or curing disorders associated with plant injury. For example, a variety of economically significant disorders of crop plants are linked to plant injury e.g., in potato, tuber injury can result in bacterial and fungal infection. Thus, directly depositing a heterologous gene product at sites of injury, wherein the gene product protects against diseases and disorders associated with an injury, is but one of many useful applications for which isolated rice LP2 promoters are utilized.

Thus, in an exemplary embodiment, an expression vectors comprising an isolated rice LP2 promoter operably linked to a heterologous nucleic acid encoding a protective gene product is used to directly deposit the protective gene product at sites of injury. In one exemplary embodiment, a protective gene product is an antimicrobial gene product. Exemplary "antimicrobial gene products" include, but are not limited to: lytic peptides as disclosed in e.g., U.S. Pat. No. 6,084,156; plant antimicrobial peptides (see e.g., Broekaert, W. F., et al. (1997 Crit. Rev. Plant Sci. 16:297-323) and synthetic antimicrobial peptides (see e.g., Bessalle, R., et al. (1993). J. Med. Chem. 36:1203-1209; Arrowood, M. J., et al., (1991) J. Protozool. 38: 161s; and Jaynes, J. M., et al., (1988) FASEB J. 2: 2878).

Kits

In an exemplary embodiment, kits comprising isolated rice LP2 expression vectors are provided for expressing heterologous nucleic acids in plant cells. The kits typically include, inter alia, an expression vector comprising an isolated rice LP2 promoter and written instructions for using the kit to express heterologous nucleic acid sequences in plants and/or plant cells.

The following examples are offered to illustrate, but not to limit the invention.

EXAMPLES

Example 1

Materials and Methods for Example 1

Plant Materials, Growth Conditions and Transformation

Nipponbare rice (*Oyzae sativa*, japonica type, GSOR #100) was obtained from the Genetic Stocks—Oryza Collection at the Dale Bumpers National Rice Research Center in Stuttgart, Ark. Rice plants were grown in a greenhouse environment under a mean temperature of 28° C. and supplemented with 16 hours per day of sodium lamp light. Seeds and transplanted seedlings were potted in Sunshine mix #1 (Sun-Grow Horticulture Distribution, Bellevue Wash.) with slow release fertilizer Osmocote Plus 15-9-12 plus micronutrients (Scotts-Sierra Horticultural Products, Marysville, Ohio) added. The six inch pots were partly submerged in trays of water and Peter's liquid fertilizer 20-20-20 plus micronutrients (Scotts-Sierra Horticultural Products, Marysville, Ohio) was added once each week to the twice daily watering regime.

Rice was transformed via *Agrobacterium*-mediated transformation according to a method derived from Sallaud et al. (2003) *Theor. Appl. Gen.* 106, 1396-1408 and Yang et al. (2004) *Plant Science* 167, 281-288 as previously described (see e.g., Thilmony et al., (2006) *Plant Mol. Biol. Rep.* 24, 57-69). Regenerated $T_0$ plants were transferred to soil and grown in the greenhouse as described above. Harvested $T_1$ and $T_2$ transgenic rice seed was dried for five days at 50° C., de-hulled and then surface sterilized (placed in 70% ethanol for five minutes, transferred to a solution of 30% bleach with 0.1% Triton X-100 for 20 minutes, and then rinsed five times with sterile water) prior to sowing. The seed was then either sown in sterilized sand, or placed on germination media containing 4.33 g/L MS basal salts, 2.6 g/L Phytagel, 0.5 mg/L 6-benzylaminopurine and 40 mg/L hygromycin and then incubated in a growth chamber at 28° C. under a 16 hour light/8 hour dark cycle. Seedlings were scored for antibiotic resistance after 2-3 weeks of growth.

Young leaves and root tissue for RNA analysis were harvested from approximately two-week old sand-grown seedlings. Mature leaf tissue and reproductive tissues were harvested from greenhouse plants. For the light-dark expression analysis, seed was grown in sterile sand in a growth chamber either exposed to the 16 hour light/8 hour dark cycle with an approximate light intensity of 250 $\mu mol/m^2/sec$ provided by fluorescent and incandescent bulbs or kept in complete darkness within a light-tight container. Both leaf and root tissues were harvested approximately two weeks after germination. All plant material was immediately frozen in liquid nitrogen, then stored at −80° C.

LP2 Cloning and Vector Construction

A partial LP2 cDNA was amplified from rice leaf RNA using Reverse Transcriptase-PCR with the following primers: OligoT$_{23}$V (an anchored oligo-dT primer for reverse transcription, V=A, C or G), Os5867F1 5'-AGGTAACATGGGC-CTCACG-3' (SEQ ID NO:6) and Os5867R15'-GGCAC-CATAGACACCAAGCA-3' (SEQ ID NO:7). The 744 bp PCR product was cloned using the Invitrogen TOPO TA cloning kit (Carlsbad, Calif.) and sequenced. The cloned LP2 cDNA was 99.6% identical to the rice Os02g40240 gene, and has less than 70% nucleotide identity with other genes in the rice genome.

The LP2 upstream promoter, 5' intron and 5' portion of the first coding exon (−1807 to +414) was amplified from Nipponbare genomic DNA with high fidelity polymerase using the following primers: Os5867gF2_BamHI 5'-CGCGGATC-CGCACGAACCAGCTTTGTGG-3' (SEQ ID NO:8) and Os5867gR2_NcoI 5'-CGCCCATGGAATCGACGTTGC-CAATCCCA-3' (SEQ ID NO:9). This 2220 bp LP2 genomic fragment was digested and cloned into the BamHI and NcoI sites of pCAMBIA1303 (GenBank Accession AF234299) binary vector making a translational fusion to the gusA:: mGFP5 reporter gene (see FIG. 5 for T-DNA map of the pC1303-LP2 vector). The LP2 upstream promoter, 5' intron and 5' portion of the first coding exon (−1936 to +336) was amplified from Nipponbare genomic DNA with high fidelity polymerase using the following primers: Os5867gF3_SacII 5'-CCGCGGATTGAATCCATGAGGATGGTGGG-3' (SEQ ID NO:10) and Os5867gR3_NcoI 5'-CCATGGACGTGAG-GCCCATGTTACC-3' (SEQ ID NO:11). This 2271 bp LP2 genomic fragment was cloned into the SacII and NcoI sites of the pGPro 1 (see Thilmony et al., 2006, supra) binary vector making a translational fusion to the GUS::eGFP reporter gene (see FIG. 5 for T-DNA map of the pGPro1-LP2 vector). The pGPro1-35S vector was constructed by inserting a 819 bp double-enhanced CaMV 35S promoter fragment from pCAMBIA1303 into the SacII and NcoI restriction sites of pGPro1 (see FIG. 5 for T-DNA map of the pGPro1-CaMV35S vector). After DNA sequencing to confirm their structures, each binary vector plasmid was isolated with the Fermentas GeneJET Plasmid Miniprep Kit (Glen Burnie, MD), electroporated into *Agrobacterium tumefaciens* strain AGL1 (Lazo et al., (1991) *Bio/Technol.* 9, 963-967) and used to generate transgenic Nipponbare rice plants.

DNA and RNA Gel Blot Analyses

Rice genomic DNA was isolated from leaves of greenhouse grown plants using a miniprep procedure (Dellaporta et al., (1983) *Plant Mol. Biol. Rep.* 1, 19-21). Ten µg of rice genomic DNA was digested with NcoI or KpnI, separated on an 0.8% agarose gel and blotted onto Hybond N+ (Amersham Biosciences, Piscataway, N.J.) positively charged nylon membrane using 0.4M sodium hydroxide. RNA was isolated from rice callus, leaf, root, and reproductive tissues using Trizol reagent (Invitrogen, Carlsbad, Calif.) with chloroform washes. Isopropanol and sodium acetate were used to pellet the RNA. The pellet was rinsed with 70% ethanol and resuspended in RNase-free water. Three µg of each RNA or two µg of light or dark grown leaf and root RNA were separated on an 0.8% agarose gel and transferred onto Hybond N+ (Amersham Biosciences, Piscataway, N.J.) membrane using 20×SSC buffer (Sambrook et al., 1989, supra). DNA and RNA blots were cross-linked using the UV Stratalinker 2400 (Stratagene, La Jolla, Calif.).

A 496 bp gusA DNA fragment called GUS5 (shown in FIG. 5) was used as a probe in DNA and RNA blot analyses. The 744 bp LP2 partial cDNA was used as a gene-specific probe in RNA blot hybridization analysis. Probes were radioactively labeled using $\alpha P^{32}$-dCTP with the Rediprime II Random Prime Labeling System and purified through ProbeQuant G-50 microcolumns from Amersham Biosciences (Piscataway, N.J.). Blot hybridizations were performed using the Sigma PerfectHyb™ Plus hybridization buffer (Sigma-Aldrich, St. Louis, Mo.) as recommended by the manufacturer. Hybridized blots were washed to 1×SSC 0.1% SDS at 50° C. and exposed to X-ray film.

The radioactive signal present on the light-dark RNA blot was quantified using storage phosphor autoradiography with a Molecular Dynamics Storm 820 Phosphoimager™ (Sunnyvale, Calif.). Image Quant software measured the radioactive signal intensity using equal sized boxes placed over the regions of the blot containing the RNA transcript for each of the samples. The background signal was calculated by averaging the signal for the four nontransgenic samples. The signal intensity measured for each sample was then divided by this background value to generate the quantified transcript levels.

Detection of β-Glucuronidase Activity

Histochemical staining for β-glucuronidase activity was performed as previously described (see e.g., Jefferson, (1987) *Plant Mol. Biol. Rep.* 5, 387-405; Rueb and Hensgens, (1989) *Rice Genetics Newsletter* 6, 168). Briefly, the samples were prewashed in 0.07% (v/v) Liqui-Nox soap (ALCONOX, Inc. New York) in 0.1 M phosphate buffer and vacuum-infiltrated in GUS staining solution for approximately 10 minutes to promote substrate penetration (Rueb and Hensgens, 1989, supra). The GUS staining solution contains 0.1 M sodium phosphate pH 7.0, 0.5 mM potassium ferrocyanide, 0.5 mM potassium ferricyanide, 1.5 g/L X-Gluc (5-bromo-4-chloro-3-indolyl-β-D-glucronic acid) and 0.5% (v/v) Triton X-100. The plant tissue samples were typically incubated in staining solution at 37° C. for approximately 12 hours. Occasionally, incubation was performed at 55° C. (Hansch et al., (1995) *Plant Sci.* 105, 63-69) instead of 37° C. if background staining was observed in nontransgenic control tissue samples at the lower temperature. When incubation was performed at 55° C., background staining in wild type control samples was not observed, allowing the histochemical detection of reporter gene-mediated β-glucuronidase activity.

Fluorometric analysis of β-glucuronidase activity in leaf and/or root tissues was performed using the TKO 100 DNA Fluorometer (Hoefer Scientific Instruments, San Francisco, Calif.). β-glucuronidase enzymatically converts the substrate MUG (4-Methylumbelliferyl β-D-glucuronide hydrate) to the fluorescent product MU (4-Methylumbelliferone). Crude protein extract was prepared from ground tissue samples according to Serres et al. (1997) *Plant Cell Rep.* 16, 641-646. The fluorometer was calibrated with 0.5 pmol MU (Sigma-Aldrich, St. Louis, Mo.) equal to 1000 U and two µl of protein extract was added to 500 µl of 1 mM MUG (Sigma-Aldrich, St. Louis, Mo.) assay buffer. Aliquots of the reaction were sampled every 15 minutes and the quantity of MU produced over a 60 minute reaction per µg of crude protein was calculated. Protein extract quantification was performed using the Bio-Rad Protein Micro Assay (Bio-Rad Laboratories, Hercules, Calif.).

Microscopy, Sectioning, and Photography

GUS reporter gene expression was visualized under bright field conditions using an Olympus BX51 microscope system, and images were documented using the attached DP70 digital camera (Olympus, Melville, N.Y.). Microscopic images between 2× and 10× were documented using a Leica MZ16F stereomicroscope (Leica Microsystems, Bannockburn, Ill.) with attached Retiga 2000R FAST Cooled Color 12 bit digital camera (Q Imaging, Pleasanton, Calif.). GFP fluorescence was examined with the addition of an XCite 120 Fluorescence Illumination System (EXFO Life Sciences, Mississauga, Ontario, Canada) to the Leica stereomicroscope with the following fluorescence filter set: excitation: 450-490 nm and barrier/long pass 515 nm. Five-ten μm thin sections of GUS stained rice leaves and roots were produced using a Leica CM3000 (Leica Microsystems, Bannockburn, Ill.) cryomicrotome at −18° C. The sections were adhered to glass slides and examined for cell-localized GUS expression.

Sequence Analysis and Cis Element Identification

Sequences were examined using the Gramene website BLAST search and Contig Viewer (Ware et al., (2002) *Plant Physiol.* 130, 1606-1613). Putative promoter cis regulatory elements were analyzed using the Plant C is Acting Regulatory Element search for CARE tool (PlantCARE Lescot et al., (2002) *Nucl. Acids Res.* 30, 325-327), the Plant Promoter Analysis Navigator (PlantPAN Chang et al., (2008) *BMC Genomics* 9, 561), and the Database of Plant Cis-acting Regulatory DNA Elements (PLACE Higo et al., (1999) *Nucl. Acids Res.* 27, 297-300). The presence of several known cis elements that were not included within the above websites' databases, i.e. LPSE2 and other motifs present in the rice green tissue specific D540 promoter (Cai et al. (2007) *Plant Biotech. J.* 5, 664-674), the PBX and TBX elements (Regad et al., (1994) *J. Mol. Biol.* 239, 163-169; Tremousaygue et al., (2003) *Plant J.* 33, 957-966; Michael et al., (2008) *PLoS Genet.* 4, e14, and the rice Intron Mediated Enhancement (IME) motif (Rose et al., (2008) *Plant Cell* 20, 543-551) were queried and annotated manually within the LP2 sequence.

Results for Example 1

Identification and Isolation of a Rice Gene Expressed Primarily in Leaves and Other Green Tissues.

To identify rice promoters that have organ- or tissue-specific expression patterns of potential use in crop biotechnology, transcript profiling approaches were used to examine gene expression. Using a rice cDNA microarray (Bohnert Lab, 192 ERML, 1201 W. Gregory Drive, Plant Biology/Crop Sciences Departments, University of Illinois, Urbana-Champaign, Urbana, Ill. 61801, USA), we identified an Expressed Sequence Tag (EST; GenBank accession CA753991) that exhibited substantial levels of expression in Nipponbare rice seedling leaf and flowering panicle samples. This same microarray element exhibited little or no detectable expression in seedling root, immature panicle (non-green tissue dissected from the boot), stamen, and developing seed samples. Based on the CA753991 EST sequence, primers were designed and a 744 base pair (bp) partial cDNA was amplified with reverse transcriptase-PCR using Nipponbare leaf RNA as template. The amplified cDNA was cloned, sequenced and compared to the publicly available rice genome sequence. The cloned cDNA sequence matched the 5' end of a novel LRR-receptor kinase-like gene (LOC_Os02g40240). We named this gene Leaf Panicle 2 (LP2) based on its organ-specific expression pattern. Several other rice genes had modest nucleotide sequence similarity to the cloned LP2 cDNA fragment, but each contained less than 70% overall nucleotide identity and thus were unlikely to have cross-hybridized with this sequence.

The steady-state transcript levels of LP2 in various tissues were further examined using RNA blot analysis. Using the 744 bp LP2 cDNA as a probe, a transcript approximately 3.5 kb in length was detected in seedling leaf and flowering panicle RNA samples. Little or no transcript was detectable in RNA from seedling roots, stamens (prior to anthesis), developing seeds at the soft-dough stage, undifferentiated callus tissue grown in the dark, and immature panicle tissue prior to emergence from the boot. The leaf and flowering panicle samples used for RNA blot analysis include chlorophyll-containing tissues (leaf blade or the lemma, palea and rachis respectively), while the other samples did not, suggesting that LP2 was specifically expressed in photosynthetically active green tissues.

To further validate the organ-specific expression pattern of the LP2 gene, we also examined global transcriptional profiling data that had recently become publicly available. The steady state LP2 transcript levels detected on the rice Affymetrix GeneChip™ arrays were visualized using the Genevestigator MetaProfile Analysis tool (see Zimmermann et al., (2008) *Molecular Plant* 1, 851-857). Using the anatomy analysis scatterplot visualization feature, significant signal for the probe set representing the LP2 gene (Os.11890.1.S1_at) is exclusively detected in the leaf and shoot samples. Only background levels of signal are observed in the other organ/tissue types currently represented in the Genevestigator database. The green-tissue expression specificity of the LP2 gene was similarly supported from analysis performed with the rice gene expression atlas (RiceGE Salk Institute Genomic Laboratory,) and Massively Parallel Signature Sequence tags (MPSS; Nobuta et al., (2007) *Nature Biotech.* 25, 473-477). Interestingly, it became clear from these analyses that LP2 transcript expression was only detected in leaf and shoot samples of japonica rice, but not in samples from indica rice. Genome sequence analysis suggests that the region of chromosome 2 containing the LP2 gene is absent or highly divergent in indica rice, thus explaining the failure to detect LP2 expression in the indica samples. Overall, these results support the conclusion that the LP2 gene is strongly and specifically expressed within leaves and other photosynthetic shoot tissues of japonica rice plants.

The observed size of the LP2 transcript on the RNA blot is consistent with expectations based on the available full-length cDNA and partial EST sequences present in the database. A full length cDNA (GenBank Accession AK065018) 3475 bp in length has been cloned and sequenced (Kikuchi et al., (2003) *Science* 301, 376-379), but sequences from other partial cDNA clones suggest that a shorter LP2 transcript 3420 bases in length is also expressed. These two LP2 transcripts differ in length by 55 bases due to alternative splicing of an intron within the 5' untranslated region (UTR) upstream of the translational start site (FIG. 1). Determining whether one or both of these two LP2 transcripts are detected via RNA blot hybridization was difficult since the difference in length is small relative to the total transcript size and thus unlikely to be resolved on the gel. The shorter LP2 transcript is represented by 54 EST sequences in the database, while the longer transcript is supported by only 24 ESTs, (see Quackenbush et al., (2001) *Nucl. Acids Res.* 29, 159-164). These EST abundances suggest that the shorter 3420 base transcript accumulates to higher levels, at least in those samples used to generate the various EST libraries. The predominant transcription start site, designated +1 in FIG. 1 (323 bp upstream of the translation start codon) was deduced based on alignment of the guanine capped, full length cDNA (AK065018) and the available 5' EST sequences with the rice genome sequence.

Isolation of the LP2 Promoter and Generation of Reporter Gene Fusion Constructs.

To examine the ability of the LP2 promoter to control organ/tissue-specific transgene expression in rice, we used PCR to amplify a 2221 bp region of sequence upstream of the translation start codon. Initially we made a translational fusion of this fragment (from −1807 to +414 numbered relative to the transcription start site) to the GUS::mGFP5 reporter gene in the pCAMBIA1303 binary vector (GenBank Accession AF234299). This LP2 promoter fragment includes 91 bp of coding sequence, the entire 323 bp 5' UTR including the alternatively spliced 5' intron and 1807 bp of upstream promoter sequence (FIG. 1). Although the LP2 promoter does not contain a match for the TATA box consensus sequence CTATAWAWA, where W=A or T (Civan and Svec, 2009, supra), it does contain a T/A-rich sequence from −31 to −24 bp upstream of the transcription start site, the typical location of a TATA box (FIG. 1). It also contains a "Y patch" (C/T pyrimidine-rich sequence at +97 to +108, FIG. 1), which is present in the 5' UTR of many rice transcripts (Civan and Svec, 2009, supra). Another feature of the LP2 promoter is a 353 bp directly repeated sequence (FIG. 1). The two repeat sequences are 93% identical and A+T rich (70% A+T), but do not match other sequences in the rice genome and are not transposon-derived repeat elements. The structure of the resulting binary vector (pC1303-LP2) was confirmed by DNA sequencing and the plasmid was introduced into *Agrobacterium tumefaciens* strain AGL1. A diagram of the pC1303-LP2 T-DNA region is shown in FIG. 5.

We constructed pGPro1, a novel binary vector well suited for promoter analysis in monocot plants (Thilmony et al., 2006, supra). A 2272 bp LP2 promoter and partial coding region from −1936 to +336 (FIG. 1) was amplified and translationally fused to the GUS::eGFP bifunctional reporter gene in the pGPro1 binary vector. This LP2 promoter fragment includes 13 bp of coding sequence, the entire 323 bp 5' UTR including the alternatively spliced 5' intron and 1936 bp of upstream promoter sequence (FIG. 1). The pGPro1-LP2 vector was sequenced to confirm its structure and introduced into *Agrobacterium tumefaciens* strain AGL1 (Lazo et al., 1991, supra). A diagram of the T-DNA region of the pGPro1-LP2 binary vector is shown in FIG. X. A positive control binary vector (pGPro1-CaMV35S) carrying the double enhanced CaMV35S promoter fused to the GUS:: eGFP reporter gene (FIG. 5) was also constructed.

Generation of LP2 Promoter-Reporter Transgenic Rice.

Transgenic rice plants were generated using the pC1303-LP2 and pGPro1-LP2 constructs via *Agrobacterium tumefaciens* transformation (see Experimental Procedures). A total of 23 pC1303-LP2 plant lines and ten pGPro1-LP2 plant lines were regenerated and grown to maturity in the greenhouse. Reporter gene expression was examined in the leaves of the $T_0$ plants using histochemical staining. 27 of the 29 lines tested exhibited O-glucuronidase activity. The two transgenic pC1303-LP2 plant lines that lacked detectable activity in leaves were not characterized further. Southern blot hybridization analysis was performed on seven $T_1$ plant lines, five pC1303-LP2 and two pGPro1-LP2 lines. Genomic DNA was digested with either NcoI or KpnI restriction enzymes, which each cut only once within the T-DNAs. Genomic DNA from pC1303-LP2 transgenic lines digested with NcoI or KpnI and hybridized with a GUS probe (shown in FIG. 5) are expected to produce bands greater than 2.9 kb or 5.1 kb respectively for intact T-DNAs. Likewise, genomic DNA from pGPro1-LP2 transgenic lines that contain complete T-DNAs are expected to produce bands greater than 5.7 kb for the NcoI digest or 5.6 kb for the KpnI digest when hybridized with a GUS probe. The blot hybridization results illustrate that the seven lines contain one to four copies of the T-DNA. Each transgenic line contains one or more GUS hybridizing bands of different sizes larger than the expected T-DNA fragment, indicating that each line is independent with a likely intact reporter transgene cassette(s) integrated at a unique genomic location (s).

LP2 Promoter Drives High Expression in Leaves of Transgenic Rice Seedlings.

The plant lines examined by Southern blot analysis were fully fertile, and thus were selected for further characterization of reporter gene expression in the $T_1$ and $T_2$ generations. Detection of β-glucuronidase activity allowed easy and reliable documentation of reporter gene expression, but we also evaluated whether we could utilize visualization of fluorescence in live plant tissues mediated by the GUS::Green Fluorescent Protein bifunctional reporters fused to the LP2 promoter in the pC1303-LP2 and pGPro1-LP2 vectors. Several $T_1$ hygromycin-resistant seedlings for each line were examined under ultraviolet and blue light to visualize GFP fluorescence. No green fluorescence was detected in seedling roots of either the pC1303-LP2 or pGPro-LP2 construct lines suggesting the LP2 promoter, as expected, does not confer detectable levels of GFP expression in seedling roots. Unfortunately, GFP fluorescence in seedling leaves was somewhat difficult to detect using the available visualization systems because it was masked by chlorophyll (red) autofluorescence. We have found that detection of GFP fluorescence in leaves of other transgenic rice lines expressing the bifunctional reporters controlled by strong constitutive promoters (e.g. CaMV35S and rice Act1) was also challenging. Only a few LP2 and 35S promoter transgenic lines with unusually high levels of expression reproducibly exhibited levels of GFP fluorescence that were distinguishable from chlorophyll autofluorescence in green tissues and were clearly different from wild type controls. For these reasons, we chose to utilize detection of β-glucuronidase activity to further examine and document LP2 promoter-mediated reporter gene expression in subsequent experiments.

Seedlings of the seven lines were grown for two weeks in sand and then histochemically stained for GUS activity. Representative results for two of the LP2 promoter transgenic lines compared to non-transgenic and CaMV35S control plants. Both roots and leaves of the seedling containing the pGPro1-CaMV35S promoter construct stained strongly for β-glucuronidase activity, while no background staining was observed in wild type Nipponbare seedlings under our staining conditions. GUS staining observed in both the pC1303-LP2 and pGPro1-LP2 transgenic lines was the strongest in the leaf blade with weaker staining in the leaf sheath and little or no staining visible in the roots. Similar results were observed for the other LP2 transgenic lines, and although the strength of staining varied among the lines, the five pC1303-LP2 and two pGPro1-LP2 independent transgenic lines all exhibited the same organ-specific pattern of expression. The two pGPro1-LP2 lines (#2 and #3) tended to exhibit quantitatively darker staining in the seedling leaf blade and sheath compared to the pC1303-LP2 lines (#7, 32, 51, 55 and 62). The pC1303-LP2 line #7 had the weakest staining in the seedling leaf blade and exhibited little or no GUS staining in the leaf sheath. These results demonstrate that both the pC1303-LP2 and pGPro1-LP2 binary vector constructs generated multiple transgenic rice lines with organ-specific reporter gene expression despite containing different T-DNA components in different orientations relative to the borders and the selectable marker expression cassette.

LP2 Promoter Exhibits Green Tissue-Specific Expression in Adult Transgenic Rice Plants.

The organ-specific expression pattern conferred by the LP2 promoter was further characterized spatially and temporally throughout plant development. β-glucuronidase activity was examined in various tissues of pC1303-LP2 and pGPro1-LP2 transgenic rice plants grown in the greenhouse. Histochemical staining was strong in both seedling and mature leaves, but exhibited distinctly different spatial GUS staining patterns depending on leaf maturity. Two-week-old seedling leaves stained evenly throughout the blade, while mature leaves from greenhouse grown plants typically stained most strongly at the cut edges and along the longitudinal veins. GUS staining away from the cut edges was usually much weaker than near the cut edges. This staining pattern in mature leaves is likely an artifact of the failure of the X-Gluc substrate solution to evenly penetrate the hydrophobic surfaces of the mature rice leaves. We attempted to improve the uniformity of staining by vacuum infiltrating the GUS staining solution, but even with these additional measures, staining of LP2 and CaMV35S control transgenic lines was typically weak or not detected more than a few millimeters from the cut edge of the leaf. In mature leaf blade cross-sections, the darkest GUS staining occurs within the mesophyll cells while lighter staining was visible in the other cell types of the leaf including the epidermal, xylem, phloem and bulliform.

GUS activity was detected histochemically also in leaf sheaths, and non-reproductive green tissues of the panicle in both the pC1303-LP2 and pGPro1-LP2 transgenic lines. The lemma, palea, awn and pedicel each exhibited GUS activity with the strongest staining typically observed in the pedicel and along the ribs of the lemma. The stamen and pistil reproductive structures do not show detectable GUS activity. The (green) pericarp of immature seeds also showed GUS activity, but the immature embryo or endosperm did not stain. Imbibed mature seeds did not display detectable β-glucuronidase activity in the embryo, endosperm or the pericarp. Whole roots from greenhouse grown plants did not exhibit GUS staining activity nor contain any visibly blue cells when examined following sectioning. Hygromycin-resistant callus was generated from the $T_1$ seed of several of the transgenic lines and then examined for β-glucuronidase activity. Most of the calli pieces did not exhibit blue staining, but occasionally some sectors of individual calli had weak GUS activity.

LP2 Promoter is Light-Induced in Seedling Leaves.

Since the native LP2 gene exhibited expression in photosynthetic tissues and the LP2 promoter conferred reporter gene expression in these same locations, we further investigated whether expression was regulated in response to light. Homozygous $T_2$ seed of control and transgenic lines were germinated in sterile sand in the dark or under a 16L:8D light regime in the growth chamber at 28° C. After two weeks, individual seedlings were either stained for β-glucuronidase activity or the leaf and root tissues were harvested for RNA or protein extraction. Dark grown LP2 seedlings, compared to the light grown individuals, had much lower levels of GUS staining in the aerial parts and reproducible staining was observed only in the tips of the coleoptile and first true leaves. In contrast, GUS activities in the light and dark grown pGPro1-CaMV35S plants were similar to one another, although the leaves and the roots of the light grown seedlings tended to stain more darkly than the dark grown plants.

β-glucuronidase activity was also measured using a fluorimetric substrate to quantify the histochemical staining results. CaMV35S and LP2 promoters exhibited similar levels of activity in light-grown seedling leaves, while leaves of the LP2 dark grown seedlings exhibited detectable activity at levels approximately 7-fold lower. The GUS activity in the LP2 seedling was more than 150-fold higher in the light grown leaves than the roots, which had levels of activity essentially indistinguishable from background. The CaMV35S promoter also exhibited a modest light-responsive induction (~2-3 fold) in leaves.

Reporter gene transcript levels in the light and dark grown seedlings were also examined using RNA blot analysis. RNA transcript was not detected in light or dark grown seedling roots or dark grown seedling leaves of the LP2 transgenic lines, while approximately 40 fold higher levels of transcript were detected in light grown LP2 transgenic leaves compared to the background signal detected on the blot for the dark grown leaves, consistent with the observed reporter gene activity. This level of transcript was similar to that observed in light grown leaves of a CaMV35S transgenic line. Negligible activity was detected in nontransgenic leaf and root samples as well as root samples from LP2 expression lines.

The light-responsive expression mediated by the LP2 promoter could be dependent on light-stimulus in a diurnal fashion or potentially regulated via the plant circadian clock. We further examined the light-dependent pattern of expression of the LP2 gene using the Diurnal website (Mockler et al., (2007) Cold Spring Harbor Symposium on Quantitative Biology 72, 353-363). The LP2 gene exhibited diurnal cycling with the normalized transcript levels varying 3-4 fold between day and night in the "LDHH" and "LDHC" samples. The LDHH samples were grown under a 12L:12D with a constant temperature of 31° C., while the LDHC samples were grown under a 12L:12D with a daytime temperature of 31° C. and a nighttime temperature of 20° C. Surprisingly, the peak expression levels were detected at midnight, while the lowest transcript levels were observed from dawn to midday in the diurnal time-course experiments.

Discussion of Results for Example 1

We have demonstrated that the LP2 promoter confers strong organ-specific reporter gene expression in leaves and other green tissues of transgenic rice plants. LP2-mediated reporter gene expression was either weak or not detected in roots, seeds (with the exception of the green pericarp during seed development) or the non-green reproductive structures. Multiple independent transgenic plants containing either the pC1303-LP2 or pGPro1-LP2 T-DNAs, located in different genomic positions with different copy numbers, displayed a consistent pattern of organ-specific expression despite the differences between the composition and structure of the two constructs.

The pattern of expression conferred by the LP2 promoter in transgenic rice plants was entirely consistent with the expression pattern of the native LP2 gene. This suggests that the important control elements responsible for organ-specific and light-responsive expression of the LP2 gene are present within the approximately 2.2 kb upstream fragment fused to the reporter genes in our transformation constructs.

The LP2 sequence in the transformation constructs tested included approximately 1.8 kb of promoter sequence (upstream of the transcription start site) containing two 353 bp direct repeats, the entire 5' UTR, the 5' intron, and a portion of the first coding exon translationally fused to the reporter gene (FIG. 5). When this portion of sequence was analyzed for the presence of cis regulatory elements using various web-based analysis programs (see Experimental Procedures), numerous motifs were found that are consistent with the LP2 promoter exhibiting light-responsive expression. The sequence contains 20 different putative light-responsive cis elements (FIG. 6). These 20 elements occur 37 times within the LP2 sequence due to multiple appearances of some sequences. Several of these elements are seven, eight or nine nucleotides in length and are exact matches for known motifs (FIG. 6). For example, the LP2 promoter contains exact matches for the nine nucleotide ATC-motif (start position −490), the eight nucleotide AE-box (start position −421) and I-box (start position −81) elements. Each of these elements is associated with light-responsiveness in numerous plant species (see e.g., Arguello-Astorga and Herrera-Estrella, 1996, *Plant Physiol.* 112, 1151-1166; Park et al., 1996, *Plant Phys.* 112, 1563-1571). The 5′ intron also contains three light responsive cis elements including an exact eight nucleotide match for the chs-CMA2a light response element (see e.g., Arguello-Astorga and Herrera-Estrella, 1996 *Plant Phys.* 112, 1563-1571) at position +135, and two seven nucleotide matches for the Box-I element (see e.g., Kuhlemeier et al., 1988, *Proc. Natl. Acad. Sci. U.S.A.* 85, 4662-4666) at positions +180 and +213 (FIG. 3). Sequences further upstream, although not identical to the known light-responsive motifs, match 10/11 nucleotides of the GATA-motif (see e.g., Lam and Chua, 1989, *Plant Cell* 1, 1147-1156), 10/11 nucleotides of 3-AF1 binding site (see e.g., Lam et al., 1990), 9/10 nucleotides of the ATCT-motif (see e.g., Conley et al., 1994, *Mol. Cell. Biol.* 14, 2525-2533) and 11/13 nucleotides of the LPSE2 motif (see e.g., Cai et al., 2007, *Plant Biotech. J.* 5, 664-674) (FIG. 6). The LPSE2 motif is present in the rice D540 promoter and was shown to have positive regulatory function for leaf expression and negative regulatory function for root expression (Cai et al., 2007 supra).

The LP2 RNA transcript displays light-responsive diurnal changes in transcript abundance with peak levels detected in the middle of the dark cycle. The significance of this light-regulated cycling with peak expression at midnight is unknown, but it is not surprising that the LP2 transcript cycles, since 89% of reliably detected *Arabidopsis* transcripts have been shown to cycle under at least one environmental condition (Michael et al., 2008, *PLoS Genet.* 4, e14). Consistent with the diurnal expression pattern of the LP2 gene, sequences similar to the PBX protein box (Michael et al., 2008, supra) and TBX telo-box motifs (see e.g., Tremousaygue et al., 2003, Plant J. 33, 957-966) are present twice and seven times, respectively, within the promoter sequence (FIG. 6). The PBX box is identical in sequence to the FORC$^A$ response element which is associated with light signaling and defense responses in *Arabidopsis* (see e.g., Evrard et al., 2009).

The LP2 5′ intron sequence was examined via bioinformatics to estimate the likelihood that it contributes to intron mediated enhancement (IME) of expression (see e.g., Rose et al., 2008). Despite the modest size of the larger intron (230 bases), it contains two exact matches for the six nucleotide IME motif which is typically present within rice introns that enhance expression (see e.g., Rose et al., 2008 supra; FIG. 1, FIG. 3., FIG. 9). When this intron is analyzed using the IMEter tool, it achieves a 10.8 score. Positive IMEter scores correlate with intron mediated enhancement capability. For example, the IMEter score was 218 for the 462 base rice Act1 first intron and 51 for the 535 base maize Adh1 first intron, both expression-enhancing introns. In contrast, the IMEter score was −14 for the 89 base non-enhancing rice glutelin first intron (see e.g., Rose et al., 2008 supra). Thus, IMEter predicts that the LP2 first intron is a modest enhancer of gene expression. It will be interesting in the future to determine experimentally whether the 5′ intron, the direct repeats, the 5′ UTR, or specific cis elements in the promoter sequence are responsible for the observed expression pattern.

The LP2 gene encodes a LRR-receptor kinase-like protein of the LRR-XII subfamily (see e.g., Dardick and Ronald, 2006, *PLOS Path.* 1, e2). The N-terminus of the protein is predicted to contain a signal sequence targeting the protein for secretion. Bioinformatics analyses predict that the LP2 protein is plasma membrane localized with an extracellular LRR domain, a single transmembrane domain and an intercellular kinase domain (see e.g., Lee et al., 2006, *Nucl. Acids Res.* 34, W99-W103). The LP2 protein contains a cysteine residue in place of the conserved arginine residue in kinase domain VI, classifying LP2 as a non-RD receptor-like kinase. Non-RD receptor kinases of known function in plants are pathogen recognition receptors involved in innate immunity (Dardick and Ronald, 2006, supra), suggesting a potential involvement of LP2 in plant-pathogen interactions. Indeed, the LP2 protein is 41% identical and 58% similar to the Xa21 (see e.g., Song et al., 1995, *Science* 270, 1804-1806), and 33% identical and 50% similar to the Xa26/Xa3 (see e.g., Sun et al., 2004, *Plant J.* 4, 517-27; Xiang et al., 2006, *Theor. Appl. Genet.* 7, 1347-55) bacterial blight resistance proteins. The LP2 protein also contains conserved Ser686 and Ser689, but not the Thr688 (residues numbered based on Xa21 sequence), autophosphorylation sites required for Xa21 protein stability and disease resistance (see e.g., Xu et al., 2006, *Plant J.* 45, 740-751). Recently, two potential downstream targets, a MYB-like DNA-binding protein (Os01g74020) and a NAD dependent epimerase/dehydratase-like protein (Os02g54890) have been shown to interact with the LP2 kinase domain in the yeast two-hybrid system (see e.g., Ding et al., 2009, *Plant Physiol.* 149, 1478-1492).

Although the LP2 transcript is abundantly expressed in Nipponbare leaves, its expression appears to be further enhanced in leaves upon challenge with virulent and avirulent *Magnaporthe oryzae* and *Xanthomonas oryzae* pv. *oryzae* (Xoo) pathogens which cause blast and bacterial blight of rice respectively (see e.g., Shimono et al., 2003, *J. Gen. Plant Pathol.* (2003) 69, 76-82). Probenazole, a chemical inducer of disease resistance, also enhanced LP2 expression in leaves (see e.g., Shimono et al., 2003 supra; sequence ID S12429). Interestingly, the LP2 gene is transcriptionally induced approximately 5-fold in Nipponbare rice roots four days after inoculation with the parasitic plant *Striga hermonthica* compared to the mock inoculated control (see e.g., Swarbrick et al., 2008, *Striga hermonthica. New Phytol.* 179, 515-29). Although these results show that Nipponbare plant roots that are resistant to Striga parasitism have significantly increased LP2 expression compared to the control, the induced expression level is still approximately 100-fold lower than the levels detected in green leaf tissue samples (see e.g., Swarbrick et al., 2008, supra). The number of LP2MPSS tags also increases 2-3 fold in water weevil (*Lissorhoptrus oryzophilus*) damaged leaves 24 hours after exposure compared to untreated leaves.

The LP2 transcript also has also been shown to be to be responsive to abiotic stresses. Leaves from salt stressed rice plants six days after treatment exhibited a 5-fold down regulation of LP2 expression (see e.g., Kim et al., 2007, *Mol. Cells.* 24, 45-59; sequence ID AK065018). Rice plant leaves exposed to cold stress (4° C. for 24 hours) generated no MPSS tags for the LP2 gene, suggesting a substantial reduction in transcript abundance elicited by cold treatment.

Consistent with LP2 regulation by abiotic and biotic stresses, its promoter sequence contains five putative stress or pathogen response elements (FIG. 6). There are two 9/10 matches for the ABRE abscisic acid response element (see e.g., Ono et al., 1996, *Plant Physiol.* 112, 483-491) at positions −1248 and −883, one 9/10 match for a TCA salicylic acid response element (see e.g., Pastuglia et al., 1997, *Plant Cell* 9, 1-13) at position −724, and a perfect match for the seven nucleotide tobacco EIRE elicitor responsive element (see e.g., Shah and Klessig, 1996, *Plant J.* 10, 1089-1101) located at position −604 (FIG. 6). Taken collectively, our experimental and bioinformatics results, and the published data demonstrate that the LP2 transcript accumulates specifically in leaves and other green-tissues, and is responsive to various biotic and environmental stresses in Nipponbare rice plants.

In summary, we have shown that the 2.2 kb LP2 promoter exhibits consistent organ-specific light-responsive expression specificity in multiple independent transgenic rice plants, demonstrating that this promoter will be a useful tool for rice biotechnology and potentially other crop plants.

Example 2

The following example illustrates an that isolated rice LP2 promoter drives expression of an operably linked gene in a heterologous monocotyledonous plant.

We have transformed Brachypodium distachyon was transformed with a plasmid vector comprising a GUS reporter construct operably linked to an isolated rice LP2 promoter. The vector comprising the GUS reporter construct is described above in Example 1. Brachypodium is a cool season grass that is a good model for several monocot crops and biofuels-related species (e.g. wheat, barley and other Pooideae subfamily species including several cool-season forage and biofuels-related grasses). The LP2 promoter appears to drive organ-specific expression in Brachypodium as it does in rice, indicating that the promoter is useful for controlling gene expression in numerous crops and forage grass species.

Example 3

Figure 7:
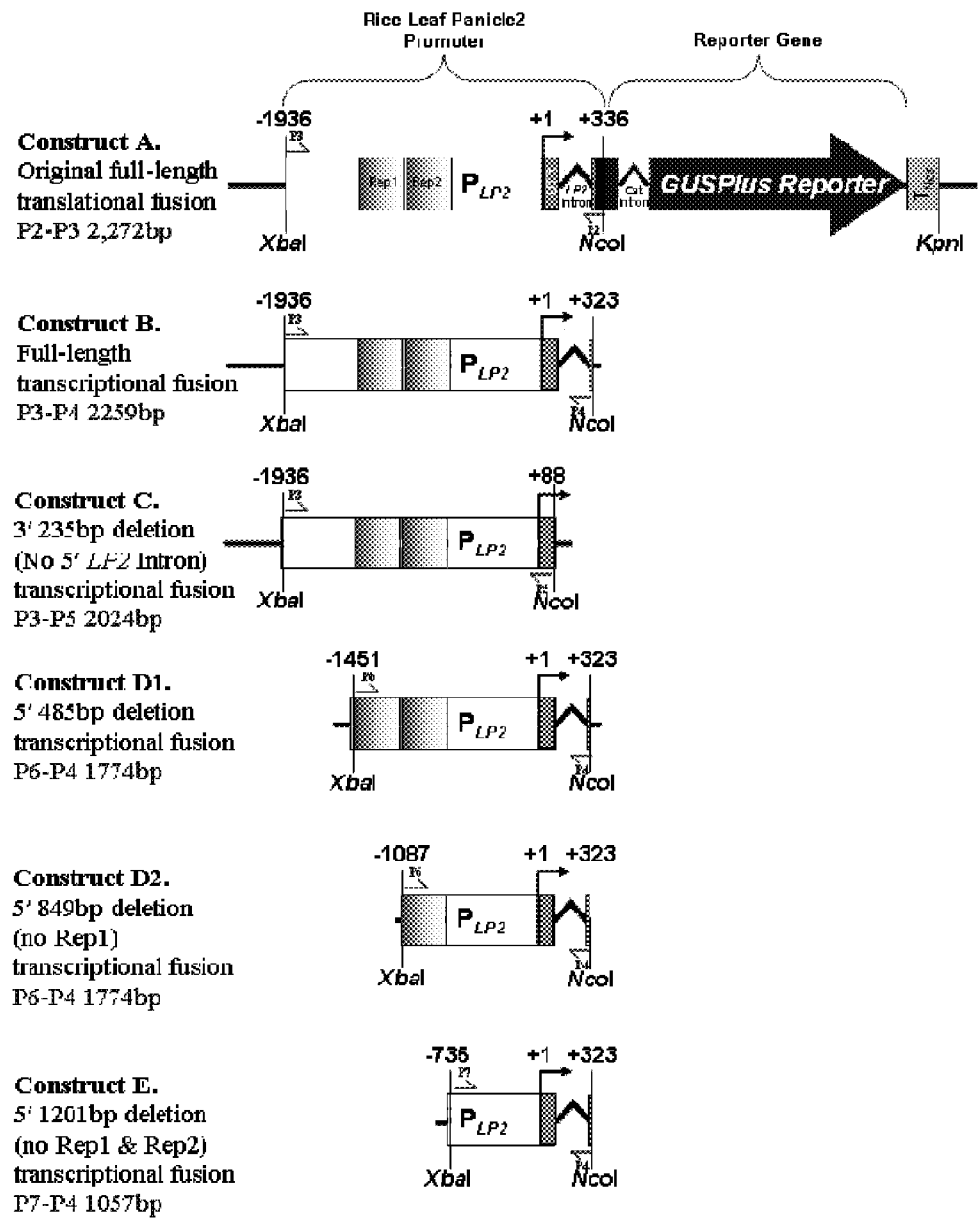
FIG. 7. Illustrates some exemplary constructs for deletion analysis of the rice LP2 promoter.

The following Example illustrates constructs for deletion analysis of the rice LP2 promoter. This analysis will reveal which regions of the LP2 promoter are of functional relevance and/or to what degree the presence or absence of the element effects promoter function/activity. Constructs for the experiments are shown in FIG. 7.

Constructs are cloned into expression vectors and tested for expression as described in Example 1. Transcriptional activity relative to that promoted by the rice LP2 promoter shown in FIG. 1 as SEQ ID NO:1, is measured.

Example 4

Figure 8:
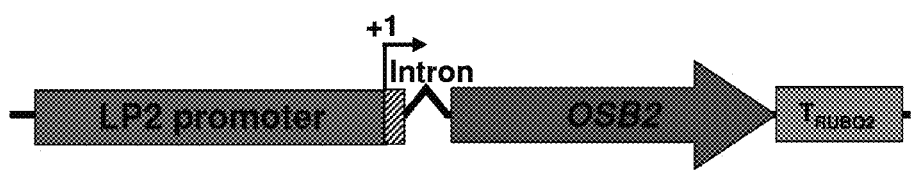
FIG. 8. Construct for OSB2 expression. The intragenic reporter gene cassette shown below contains the rice LP2 promoter driving expression of the OSB2 anthocyanin activating transcription factor and is terminated by the Rice Ubiquitin2 (RUBQ2) 3' terminator.

The following Example illustrates that the LP2 promoter is able to control expression of a rice gene called OSB2. This gene encodes a transcription factor that activates anthocyanin accumulation in certain rice plant genotypes. Anthocyanins are plant flavonoid pigments (typically red or purple in rice) that typically color flowers, fruits and leaves in numerous species. Construct for OSB2 expression is shown in FIG. 8.

Example 5

The following example illustrates that an LP2 promoter+intron sequence which further comprises coding sequence for the LP2 Signal Peptide, targets the native LP2 protein for import in the Endoplasmic Reticulum (ER) and secretion and thus can be used in for to subcellular localization of a protein of interest for secretion. An exemplary LP2 promoter nucleic acid comprising an LP2 Signal peptide is shown in FIG. 3. as SEQ ID NO:3.

The LP2 promoter+intron sequence used in the translational fusion in one of our constructs (pC1303-LP2) included 92 bp of the LP2 coding sequence. This region encodes the amino terminal 30 amino acids and includes the predicted Signal Peptide which likely targets the native LP2 protein for import in the Endoplasmic Reticulum (ER) and secretion (the LP2 protein is expected to be a plasma membrane localized receptor). Thus the LP2 promoter used in combination with this 5' coding sequence could potentially used to subcellularly localize the protein of interest for secretion (necessary for localization to the ER, golgi, vacuole, plasma membrane or cell wall/apoplast). It is known that to have plants accumulate high levels of the introduced proteins that subcellular localization to places other than the cytoplasm may be advantageous.

Example 6

The following example illustrates that isolated rice LP2 promoter fragment without the 5' intron region drives/controls gene expression in Nicotiana benthamiana, a dicotyledonous plant.

A rice LP2 promoter construct was cloned into an expression vector as described in Example 1. The isolated rice promoter sequence comprising the expression vector is shown in FIG. 4 as SEQ ID NO:4.

Transcription/expression was assayed as described in Example 1. The results from the assay show that the isolated rice LP2 promoter fragment with the 5' intron removed (SEQ ID NO:4) expresses well in Nicotiana benthamiana leaves. In contrast, when the LP2 promoter includes the 5' rice intron, only low level expression is detected. These experiments demonstrate that the LP2 promoter, without the intron, is useful for expressing genes in a wide array of dicot crop species.

It is understood that the examples and embodiments described herein are for illustrative purposes only and that various modifications or changes in light thereof will be suggested to persons skilled in the art and are to be included within the spirit and purview of this application and scope of the appended claims.

What is claimed is:

1. An isolated rice LP2 promoter consisting of a nucleic acid sequence selected from the group consisting of:
   a nucleic acid sequence that is at least 95% sequence identical to SEQ ID NO:3 or a segment or fragment thereof, wherein the segment or fragment thereof comprises a nucleic acid sequence that is at least 95% sequence identical to the full length SEQ ID NO:2, and
   a nucleic acid sequence that is at least 95% sequence identical to SEQ ID NO:4; and
   wherein the isolated rice LP2 promoter controls transcription of an operably linked nucleic acid in a plant; and
   wherein said rice LP2 promoter is operably linked to a heterologous nucleic acid sequence.

2. The isolated rice LP2 promoter of claim 1, wherein the nucleic acid sequence is at least about 95% identical to SEQ ID NO:3.

3. The isolated rice LP2 promoter of claim 1, wherein the nucleic acid sequence is 100% identical to SEQ ID NO:1.

4. The isolated rice LP2 promoter of claim 1, wherein the nucleic acid sequence is 100% identical to SEQ ID NO:3.

5. An expression cassette comprising an isolated rice LP2 promoter operably linked to a heterologous nucleic acid sequence, wherein the isolated rice LP2 consists of a nucleic acid sequence selected from the group consisting of:
a nucleic acid sequence that is at least 95% sequence identical to SEQ ID NO:3 or a segment or fragment thereof, wherein the segment or fragment thereof comprises a nucleic acid sequence that is at least 95% sequence identical to the full length SEQ ID NO:2, and
a nucleic acid sequence that is at least 95% sequence identical to SEQ ID NO:4; and
wherein the isolated rice LP2 promoter controls transcription of an operably linked nucleic acid in a plant.

6. An expression vector comprising the expression cassette of claim 5.

7. A method for making a transgenic plant, the method comprising:
(i) transforming a plant, plant part, or plant cell with an expression vector comprising an isolated rice LP2 promoter operably linked to a heterologous nucleic acid, wherein the isolated rice LP2 promoter consists of a nucleic acid sequence selected from the group consisting of:
a nucleic acid sequence that is at least 95% sequence identical to SEQ ID NO:3 or a segment or fragment thereof; wherein the segment of or fragment thereof comprises a nucleic acid sequence that is at least 95% sequence identical to the full length SEQ ID NO:2, and
a nucleic acid sequence that is at least 95% sequence identical to SEQ ID NO:4; and
wherein the isolated rice LP2 promoter controls transcription of the heterologous nucleic acid in a plant,
(ii) selecting transformants comprising the expression vector which comprises the isolated rice LP2 promoter operably linked to the heterologous nucleic acid, and
(iii) growing the transformed plant, plant part, or plant cell into a whole plant, thereby producing a transgenic plant.

8. The method of claim 7, wherein the method further comprises:
(iv) conducting a sexual cross with the transgenic plant,
(v) obtaining seed from the sexual cross,
(vi) growing the seed from the sexual cross, and
(vii) selecting plants grown from the seed of the sexual cross which comprise the expression vector comprising an isolated rice LP2 promoter sequence operably linked to the heterologous nucleic acid sequence,
thereby producing a transgenic plant.

9. A transgenic plant comprising an isolated rice LP2 promoter operably linked to a heterologous nucleic acid sequence wherein the isolated rice LP2 promoter consists of a nucleic acid sequence selected from the group consisting of:
a nucleic acid sequence that is at least 95% sequence identical to SEQ ID NO:3 or a segment or fragment thereof, wherein the segment or fragment thereof comprises a nucleic acid sequence that is at least 95% sequence identical to the full length SEQ ID NO:2, and
a nucleic acid sequence that is at least 95% sequence identical to SEQ ID NO:4; and
wherein the isolated rice LP2 promoter controls transcription of an operably linked nucleic acid in a plant.

10. The transgenic plant of claim 9, wherein the plant is a dicotyledonous plant.

11. The transgenic plant of claim 10, wherein the dicotyledonous plant is a member selected from the group consisting of: alfalfa (*Medicago saliva*), sunflower (*Helianthus annus*), soybean (*Glycine max*), tobacco (*Nicotiana tabacum*), potato (*Solanum tuberosum*), peanuts (*Arachis hypogaea*), cotton (*Gossypium hirsutum*), sugar beets (*Beta vulgaris*), apple (*Malus pumila*), blackberry (*Rubus*), strawberry (*Fragaria*), walnut (*Juglans regia*), grape (*Vitis vinifera*), apricot (*Prunus armeniaca*), cherry (*Prunus*), peach (*Prunus persica*), plum (*Prunus domestica*), pear (*Pyrus communis*), watermelon (*Citrullus vulgaris*), tomatoes; (*Solanum lycopersicum*), and lettuce (*Lactuea sativa*).

12. The transgenic decendants of the transgenic plant of claim 9.

13. The transgenic plant of claim 9, wherein the plant is a monocotyledonous plant.

14. The transgenic plant of claim 13, wherein the monocotyledonous plant is a member selected from the group consisting of: rice (*Oryza sativa*), wheat (*Triticum aestivum*), durum (*Triticum durum*), barley (*Hordeum vulgare*), switchgrass (*Panicum virgatum*), corn (*Zea mays*), sorghum, (*Sorghum bicolor*), sugarcane (*Saccharum* sp.), rye (*Secale cereale*), oat (*Avena sativa*), banana (*Musa* sp.), millet (*Pennisetum* sp.), onion (*Allium cepa*) and garlic (*Allium sativum*).

15. A method for controlling transcription of a heterologous nucleic acid in a plant or plant cell, the method comprising:
(i) transforming a plant or plant cell with an expression vector comprising an isolated rice LP2 promoter operably linked to the heterologous nucleic acid wherein the isolated rice LP2 promoter consists of a nucleic acid sequence selected from the group consisting of:
a nucleic acid sequence that is at least 95% sequence identical to SEQ ID NO:3 or a segment or fragment thereof, wherein the segment or fragment thereof comprises a nucleic acid sequence that is at least 95% sequence identical to the full length SEQ ID NO:2, and
a nucleic acid sequence that is at least 95% sequence identical to SEQ ID NO:4;
wherein the isolated rice LP2 promoter controls transcription of the operably linked heterologous nucleic acid in a plant, thereby producing a transformed plant or plant cell; and
(ii) growing the transformed plant or plant cell under conditions where the isolated rice LP2 promoter controls transcription of the heterologous nucleic acid in the plant or plant cell.

16. The method of claim 15, wherein the expression of the heterologous nucleic acid is induced in response to light.

17. The method of claim 15, wherein the expression of the heterologous nucleic acid is induced in response to pest attack.

18. The method of claim 15, wherein the heterologous nucleic acid encodes an antimicrobial gene product.

19. The method of claim 15, wherein the heterologous nucleic acid encodes a transcription factor that activates genes for the expression of anthocyanin or pigment accumulation.

20. The method of claim 15, wherein the expression of the heterologous nucleic acid up-regulates the expression of a nucleic acid that encodes a gene product that functions in photosynthesis.

21. The method of claim 15, wherein the expression of the heterologous nucleic acid down-regulates the expression of an endogenous nucleic acid.

22. A kit comprising an expression vector comprising an isolated rice LP2 promoter wherein the isolated rice LP2 promoter consists of a selected from the group consisting of:

a nucleic acid sequence nucleic acid sequence that is at least 95% sequence identical to SEQ ID NO:3 or a segment or fragment thereof, wherein the segment or fragment thereof comprises a nucleic acid sequence that is at least 95% sequence identical to the full length SEQ ID NO:2, and a nucleic acid sequence that is at least 95% sequence identical to SEQ ID NO:4;

wherein the isolated rice LP2 promoter controls transcription of an operably linked nucleic acid in a plant and written instructions for using the kit to express heterologous nucleic acid sequences in plants and plant cells.

23. The isolated rice LP2 promoter of claim 1, wherein the nucleic acid sequence is at least 99% sequence identical to SEQ ID NO:3.

24. The isolated rice LP2 promoter of claim 1, wherein the nucleic acid sequence of claim 1 is at least 99% sequence identical to SEQ ID NO:3 or a segment or fragment thereof, wherein the segment or fragment thereof comprises a nucleic acid sequence that is at least 99% sequence identical to SEQ ID NO:2.

* * * * *

SEQUENCE LISTING

```
<160> NUMBER OF SEQ ID NOS: 11

<210> SEQ ID NO 1
<211> LENGTH: 2272
<212> TYPE: DNA
<213> ORGANISM: Oryza sativa

<400> SEQUENCE: 1
attgaatcca tgaggatggt ggggtggaca ccagcatacc taagaaaata aaaagaagt      60 tatggtataa actatgtatc aatggcccaa aagatttgat gggatactgc acaaactgaa    120
ctacaagagg cacgaaccag ctttgtgggc ataatagcaa gaagaaaaat aaatattagg    180
```

-continued

```
caaaatataa aaagaaaaat attaggcaga tttcacgaga aaaaaagcaa aaatattcgg      240
ccttaaattt tcgaattaac ttggtctaat ttttttttg ctaccattat atatggctta       300
tgatggttta aaaaaacgtg aatattaagg aaagacctaa tatcaaataa atataagagg     360
tgatgtttcg aatctatacc aactagtcca ctaccttgtg aagctagcca gaagatctct     420
gggcgtttct ctgtcttacg atggttaaca catcgtcgtc atggcaccaa aattagctag     480
acaatgtttg ctctagtcac tcgaaattat tatcctaata gagaaaaaaa agaaagcatt     540
atatcgtgtg atataaatag ttcatattac aatctggttg atcgatttat ataattgtat    600
ataagatgtg attgtactta atttagttag cataatttac atgatactat ctactaccta    660
aaatagatct taacacgcat ttgcacatgc cacgctgcta gttaaagtga tacaataaca    720
aaaatatttc ttgtagtgta acacttaatt gaattcaatc tccaacttga ttgtgaagta    780
caaaaccata ggtccagagt agtgaaagca atataaggga cttggaaaaa aaaaaccacc   840
ctcgaaaacg tttgctctag tcactcaaaa ttattatctt aatagagcaa aaaagaaagc   900
attatatcgt gtgatataaa taattcatat tacaatctga tagatcaatc tatatataat   960
tgtatataag atatgattgt acttaatta gttagcataa tttgcatgat actacctact    1020
acctaaaata gatcttacca cgcatttgca caggccacgc tgctagttaa actgatacaa   1080
taacaaaggt atttcttgta gtgtaacact taattgaatt caatctccaa cttgactgtg    1140
aagtacaaaa ccagagatcc agagtaggga gagcaatata agggacttgg aaaaaaaaac   1200
cattctctcg cctttccttc tcctgtcatt aaatatgaact tgattttat aaatgtgatg    1260
aactacgcca agactatgca cgcaactatt ccagacatc tggtattgat ttcatattca    1320
aaccaacgtg ctttcgacct gttcattggg ttggtggtca cggctgatat ttccaccactt   1380
cctgagatat tcatataatc agtatggtga catagccgtg gatgacacgg cattcgtatg   1440
tagcactgct atccaaatcg aatacataca agtttgctag acccgctgct ctgtcaacga   1500
acgaatcctg accgcagaaa caaattctgg aagaaccaaa atgaatttgt ggaacgagaa   1560
tcttgaaagg taaaccgttc atgtgctcaa agcttatctg catacaagcc ttcgagaccg   1620
gtcgcggctg tcgcatatca gcgcagaatt tctctgtccg gttccggctg aaaagtaggg   1680
ggatagatga atagtacggc catcggattc gaggttcgag ctggacatgc cgcaacaacc   1740
ttgtccagat caaacaggga cagcagcgtt tggtgatgag ccgacgaggt gaaaagttgc    1800
agtaactggc aggtttgacg gactccaggt cttgcctcta gtggcggtca agctgagata   1860
aggagtgaca attaagtgag tggatgcgac aatgctgtaa aaccgttttt aaaccccccgg   1920
gacctgggag gctgctgagc aaagttcaga gttcacaaac caccacaccc agcggcacca   1980
tagacaccaa gcagaacagg ctgctgagct ccggccgacc gaaggtgctc cattctctct    2040
cctcatcatt attgatattt gcaggatcga tcacttgagg taaatcatag aagctcaaag   2100
tgaagtgcga atattttga aaaattgagt tttgttctgc ttttaagctt tgaaaagtca    2160
gatgtgttcg tggatgatca cataagcgac catttgcctc gatcggttag cataggcagc  2220
atgccataat gttcatggtt gtatatttt gcaggtaaca tgggcctcac gt            2272
```

<210> SEQ ID NO 2
<211> LENGTH: 822
<212> TYPE: DNA
<213> ORGANISM: Oryza sativa

<400> SEQUENCE: 2

```
ttctctcgcc tttcttctc ctgtcattaa tatgaacttg attttataa atgtgatgaa      60 ctacgccaag actatgcacg caactatttc cagacatctg gtattgattt catattcaaa    120
ccaacgtgct ttcgacctgt tcattgggtt ggtggtcacg gctgatattt caccacttcc    180
tgagatattc atataatcag tatggtgaca tagccgtgga tgacacggca ttcgtatgta    240
gcactgctat ccaaatcgaa tacatacaag tttgctagac ccgctgctct gtcaacgaac    300
gaatcctgac cgcagaaaca aattctggaa gaaccaaaat gaatttgtgg aacgagaatc    360
ttgaaaggta aaccgttcat gtgctcaaag cttatctgca tacaagcctt cgagaccggt    420
cgcggctgtc gcatatcagc gcagaatttc tctgtccggt tccggctgaa aagtaggggg    480
atagatgaat agtacggcca tcggattcga ggttcgagct ggacatgccg caacaacctt    540
gtccagatca aacagggaca gcagcgtttg gtgatgagcc gacgaggtga aaagttgcag    600
taactggcag gtttgacgga ctccaggtct tgcctctagt ggcggtcaag ctgagataag    660
gagtgacaat taagtgagtg gatgcgacaa tgctgtaaaa ccgttttaa acccccggga    720 cctgggaggc tgctgagcaa agttcagagt tcacaaaacca ccacacccag cggcaccata   780
gacaccaagc agaacaggct gctgagctcc ggccgaccga ag                       822

<210> SEQ ID NO 3
<211> LENGTH: 2350
<212> TYPE: DNA
<213> ORGANISM: Oryza sativa

<400> SEQUENCE: 3
attgaatcca tgaggatggt ggggtggaca ccagcatacc taagaaaata aaaagaagt      60 tatggtataa actatgtatc aatggcccaa agatttgat gggatactgc acaaactgaa    120
ctacaagagg cacgaaccag ctttgtgggc ataatagcaa aagaaaaat aaatattagg    180 caaatataa aagaaaaat attaggcaga tttcacgaga aaaaagcaa aaatattcgg      240 ccttaaattt tcgaattaac ttggtctaat ttttttttg ctaccattat atatggctta    300
tgatggttta aaaaacgtg aatattaagg aaagacctaa tatcaaataa atataagagg    360
tgatgtttcg aatctatacc aactagtcca ctaccttgtg aagctagcca gaagatctct    420
gggcgtttct ctgtcttacg atggttaaca catcgtcgtc atggcaccaa aattagctag    480
acaatgtttg ctctagtcac tcgaaattat tatcctaata gagaaaaaaa agaaagcatt    540
atatcgtgtg atataaatag ttcatattac aatctggttg atcgatttat ataattgtat    600
ataagatgtg attgtactta atttagttag cataatttac atgatactat ctactaccta    660
aaatagatct taacacgcat ttgcacatgc cacgctgcta gttaaagtga tacaataaca    720 aaatatttc ttgtagtgta acacttaatt gaattcaatc tccaacttga ttgtgaagta    780
caaaaccata ggtccagagt agtgaaagca atataaggga cttggaaaaa aaaaccacc    840 ctcgaaaacg tttgctctag tcactcaaaa ttattatctt aatagagcaa aaaagaaagc   900
attatatcgt gtgatataaa taattcatat tacaatctga tagatcaatc tatatataat   960
tgtatataag atatgattgt acttaatta gttagcataa tttgcatgat actacctact   1020
acctaaaata gatcttacca cgcatttgca caggccacgc tgctagttaa actgatacaa   1080
taacaaaggt atttcttgta gtgtaacact taattgaatt caatctccaa cttgactgtg   1140
aagtacaaaa ccagagatcc agagtaggga gagcaatata agggacttgg aaaaaaaaac   1200
cattctctcg ccttttcttc tcctgtcatt aatatgaact tgatttttat aaatgtgatg   1260
aactacgcca agactatgca cgcaactatt tccagacatc tggtattgat ttcatattca   1320
```

```
aaccaacgtg ctttcgacct gttcattggg ttggtggtca cggctgatat ttcaccactt    1380
cctgagatat tcatataatc agtatggtga catagccgtg gatgacacgg cattcgtatg    1440
tagcactgct atccaaatcg aatacataca agtttgctag acccgctgct ctgtcaacga    1500
acgaatcctg accgcagaaa caaattctgg aagaaccaaa atgaatttgt ggaacgagaa    1560
tcttgaaagg taaaccgttc atgtgctcaa agcttatctg catacaagcc ttcgagaccg    1620
gtcgcggctc tcgcatatca gcgcagaatt tctctgtccg gttccggctg aaaagtaggg    1680
ggatagatga atagtacggc catcggattc gaggttcgag ctggacatgc cgcaacaacc    1740
ttgtccagat caaacaggga cagcagcgtt tggtgatgag ccgacgaggt gaaaagttgc    1800
agtaactggc aggtttgacg gactccaggt cttgcctcta gtggcggtca agctgagata    1860
aggagtgaca attaagtgag tggatgcgac aatgctgtaa aaccgttttt aaaccccgg    1920 gacctgggag gctgctgagc aaagttcaga gttcacaaac caccacaccc agcggcacca    1980
tagacaccaa gcagaacagg ctgctgagct ccggccgacc gaaggtgctc cattctctct    2040
cctcatcatt attgatattt gcaggatcga tcacttgagg taaatcatag aagctcaaag    2100
tgaagtgcga atattttga aaaattgagt tttgttctgc ttttaagctt tgaaaagtca    2160
gatgtgttcg tggatgatca cataagcgac catttgcctc gatcggttag cataggcagc    2220
atgccataat gttcatggtt gtatatttt gcaggtaaca tgggcctcac gtgtgataca    2280
caaactgcaa aactggccat tatactacta gcattcatac tgctatgtca tgggattggc    2340
aacgtcgatt                                                            2350

<210> SEQ ID NO 4
<211> LENGTH: 2024
<212> TYPE: DNA
<213> ORGANISM: Oryza sativa

<400> SEQUENCE: 4
attgaatcca tgaggatggt ggggtggaca ccagcatacc taagaaaata aaaagaagt      60 tatggtataa actatgtatc aatggcccaa aagatttgat gggatactgc acaaactgaa    120
ctacaagagg cacgaaccag ctttgtgggc ataatagcaa gaagaaaaat aaatattagg    180
caaaatataa aaagaaaaat attaggcaga tttcacgaga aaaaagcaa aaatattcgg    240 ccttaaattt tcgaattaac ttggtctaat tttttttttg ctaccattat atatggctta    300
tgatggttta aaaaaacgtg aatattaagg aaagacctaa tatcaaataa atataagagg    360
tgatgtttcg aatctatacc aactagtcca ctaccttgtg aagctagcca gaagatctct    420
gggcgtttct ctgtcttacg atggttaaca catcgtcgtc atggcaccaa aattagctag    480
acaatgtttg ctctagtcac tcgaaattat tatcctaata gagaaaaaa agaaagcatt    540 atatcgtgtg atataaatag ttcatattac aatctggttg atcgatttat ataattgtat    600
ataagatgtg attgtactta atttagttag cataatttac atgatactat ctactaccta    660
aaatagatct taacacgcat ttgcacatgc cacgctgcta gttaaagtga tacaataaca    720
aaaatatttc ttgtagtgta acacttaatt gaattcaatc tccaacttga ttgtgaagta    780
caaaaccata ggtccagagt agtgaaagca atataaggga cttggaaaaa aaaaccacc    840 ctcgaaaacg tttgctctag tcactcaaaa ttattatctt aatagagcaa aaagaaagc    900 attatatcgt gtgatataaa taattcatat tacaatctga tagatcaatc tatatataat    960
tgtatataag atatgattgt acttaattta gttagcataa tttgcatgat actacctact   1020
```

-continued

| | | |
|---|---|---|
| acctaaaata gatcttacca cgcatttgca caggccacgc tgctagttaa actgatacaa | 1080 |
| taacaaaggt atttcttgta gtgtaacact taattgaatt caatctccaa cttgactgtg | 1140 |
| aagtacaaaa ccagagatcc agagtaggga gagcaatata agggacttgg aaaaaaaaac | 1200 |
| cattctctcg ccttttcttc tcctgtcatt aatatgaact tgattttat aaatgtgatg | 1260 |
| aactacgcca agactatgca cgcaactatt ccagacatc tggtattgat ttcatattca | 1320 |
| aaccaacgtg ctttcgacct gttcattggg ttggtggtca cggctgatat ttcaccactt | 1380 |
| cctgagatat tcatataatc agtatggtga catagccgtg gatgacacgg cattcgtatg | 1440 |
| tagcactgct atccaaatcg aatacataca agtttgctag acccgctgct ctgtcaacga | 1500 |
| acgaatcctg accgcagaaa caaattctgg aagaaccaaa atgaatttgt ggaacgagaa | 1560 |
| tcttgaaagg taaaccgttc atgtgctcaa agcttatctg catacaagcc ttcgagaccg | 1620 |
| gtcgcggctg tcgcatatca gcgcagaatt tctctgtccg gttccggctg aaaagtaggg | 1680 |
| ggatagatga atagtacggc catcggattc gaggttcgag ctggacatgc cgcaacaacc | 1740 |
| ttgtccagat caaacaggga cagcagcgtt tggtgatgag ccgacgaggt gaaaagttgc | 1800 |
| agtaactggc aggtttgacg gactccaggt cttgcctcta gtggcggtca agctgagata | 1860 |
| aggagtgaca attaagtgag tggatgcgac aatgctgtaa aaccgttttt aaaccccgg | 1920 |
| gacctgggag gctgctgagc aaagttcaga gttcacaaac caccacaccc agcggcacca | 1980 |
| tagacaccaa gcagaacagg ctgctgagct ccggccgacc gaag | 2024 |

<210> SEQ ID NO 5
<211> LENGTH: 5693
<212> TYPE: DNA
<213> ORGANISM: Oryza sativa

<400> SEQUENCE: 5

| | | |
|---|---|---|
| attgaatcca tgaggatggt ggggtggaca ccagcatacc taagaaaata aaaagaagt | 60 |
| tatggtataa actatgtatc aatggcccaa aagatttgat gggatactgc acaaactgaa | 120 |
| ctacaagagg cacgaaccag ctttgtgggc ataatagcaa gaagaaaaat aaatattagg | 180 |
| caaaatataa aagaaaaat attaggcaga tttcacgaga aaaaaagcaa aaatattcgg | 240 |
| ccttaaattt tcgaattaac ttggtctaat ttttttttttg ctaccattat atatggctta | 300 |
| tgatggttta aaaaaacgtg aatattaagg aaagacctaa tatcaaataa atataagagg | 360 |
| tgatgtttcg aatctatacc aactagtcca ctaccttgtg aagctagcca gaagatctct | 420 |
| gggcgtttct ctgtcttacg atggttaaca catcgtcgtc atggcaccaa aattagctag | 480 |
| acaatgtttg ctctagtcac tcgaaattat tatcctaata gagaaaaaa agaaagcatt | 540 |
| atatcgtgtg atataaatag ttcatattac aatctggttg atcgatttat ataattgtat | 600 |
| ataagatgtg attgtactta atttagttag cataatttac atgatactat ctactaccta | 660 |
| aaatagatct taacacgcat ttgcacatgc cacgctgcta gttaaagtga tacaataaca | 720 |
| aaaatatttc ttgtagtgta acacttaatt gaattcaatc tccaacttga ttgtgaagta | 780 |
| caaaaccata ggtccagagt agtgaaagca atataaggga cttggaaaaa aaaaccacc | 840 |
| ctcgaaaacg tttgctctag tcactcaaaa ttattatctt aatagagcaa aaagaaagc | 900 |
| attatatcgt gtgatataaa taattcatat tacaatctga tagatcaatc tatatataat | 960 |
| tgtatataag atatgattgt acttaattta gttagcataa tttgcatgat actacctact | 1020 |
| acctaaaata gatcttacca cgcatttgca caggccacgc tgctagttaa actgatacaa | 1080 |
| taacaaaggt atttcttgta gtgtaacact taattgaatt caatctccaa cttgactgtg | 1140 |

```
aagtacaaaa ccagagatcc agagtaggga gagcaatata agggacttgg aaaaaaaaac    1200
cattctctcg ccttttcttc tcctgtcatt aatatgaact tgattttat aaatgtgatg     1260 aactacgcca agactatgca cgcaactatt ccagacatc tggtattgat ttcatattca     1320
aaccaacgtg ctttcgacct gttcattggg ttggtggtca cggctgatat ttcaccactt    1380
cctgagatat tcatataatc agtatggtga catagccgtg gatgacacgg cattcgtatg    1440
tagcactgct atccaaatcg aatacataca agtttgctag acccgctgct ctgtcaacga    1500
acgaatcctg accgcagaaa caaattctgg aagaaccaaa atgaatttgt ggaacgagaa    1560
tcttgaaagg taaaccgttc atgtgctcaa agcttatctg catacaagcc ttcgagaccg    1620
gtcgcggctg tcgcatatca gcgcagaatt tctctgtccg gttccggctg aaaagtaggg    1680
ggatagatga atagtacggc catcggattc gaggttcgag ctggacatgc cgcaacaacc    1740
ttgtccagat caaacaggga cagcagcgtt tggtgatgag ccgacgaggt gaaaagttgc    1800
agtaactggc aggtttgacg gactccaggt cttgcctcta gtggcggtca agctgagata    1860
aggagtgaca attaagtgag tggatgcgac aatgctgtaa aaccgttttt aaaccccgg     1920 gacctgggag gctgctgagc aaagttcaga gttcacaaac caccacccc agcggcacca     1980 tagacaccaa gcagaacagg ctgctgagct ccggccgacc gaaggtgctc cattctctct    2040
cctcatcatt attgatattt gcaggatcga tcacttgagg taaatcatag aagctcaaag    2100
tgaagtgcga atatttttga aaaattgagt tttgttctgc ttttaagctt tgaaaagtca    2160
gatgtgttcg tggatgatca cataagcgac catttgcctc gatcggttag cataggcagc    2220
atgccataat gttcatggtt gtatatttt gcaggtaaca tgggcctcac gtgtgataca    2280
caaactgcaa aactggccat tatactacta gcattcatac tgctatgtca tgggattggc    2340
aacgtcgatt gccgtgggaa cagagccgat cagctctcac tgcttgattt caagaagggc    2400
atcaccaacg atccatatgg agccttggcc acttggaaca ccagcacaca tttctgtagg    2460
tggcaaggtg tcaagtgcac ctccactggg ccatggcgcg tcatggcgct caatctctcc    2520
agccaaagtt tgacaggcca aataaggtcc tctctcggaa acctatcctt ccttaatata    2580
cttgacctcg gcgataataa cttacttggc tccttacctc gccttggcaa tcttaagcaa    2640
cttcaggcac tctatctgta taaaaacaat ttgacaggga taattcctga tgaacttaca    2700
aattgttcca gcttaacgta catagacctc tcaggaaatg ccctaactgg tgcacttcct    2760
ccaaatttag gctctctgtc caatctagct tatctttatc tttctgcgaa caagctaact    2820
ggaaccatcc cgcaggccct tggcaacatc accaccttgg tagaaatcta tcttgataca    2880
aatcgattcg aaggggcat tccagacaag ctttggcaat tgccgaactt gacaattttg     2940
gccctaggtc aaaacatgct atcgggtgat atcccattta acttctccag cctttctctt    3000
caacttttaa gcttggaata caatatgttc ggcaaggtat tgccacaaaa cattagtgat    3060
atggtaccta atctccaaat tcttcgcttg gattacaata tgttccaagg tcaaatccca    3120
tcttctctag gaaatgcttt gcagctaaca gaaataagta tggcaaacaa ctacttcacc    3180
gggcaaattc ctagctcttt cggaaagctt tctaaactct cctatattag tctcgaaaat    3240
aatagcctag aggcttctga tggccaaggc tgggagttcc tacacgcgtt gagaaactgt    3300
agtaatctag aactgttgtc actggctcaa aatcagctac aaggagaaat accgaattca    3360 attgggacc ttccgctcaa acttcaacag ctagtgctga gtgaaaataa gctatcagga     3420
gaagttccag caagcatagg aaaccttcag ggcctgttta ggttaagtct agatttgaac    3480
```

-continued

```
aatcttactg gcaaaataga tgagtgggtt ccaaagctta caaaactgca aaaattactt    3540
ctccacagga acaactttag cgggtcgatt ccatcgtcta tagcagagct tcctcgtttg    3600
tcaacgcttt cactagcata taatgcattt gatggtccca taccatcctc attgggaaac    3660
ctttcaggac tccagaagtt atatctaagt cataataatc tcgaaggtgt catacctcca    3720
gagcttagtt accttaaaca actaataaat ctaagtttat cagaaaacaa gcttactggg    3780
gagatccctg gcactttgag ccagtgtaaa gacctggcaa acatccaaat gggcaataac    3840
ttccttactg gcaatatccc agtaaccttt ggcgacctaa agagcctggg cgtactcaat    3900
ctttcccata acagcttgtc gggcacaatt ccgactacac taaatgatct accagtcatg    3960
agcaaactgg acctttcata caatcgtctc caaggaaaaa taccaatgac tggaatattt    4020
gcaaatccta ctgttgtttc ggtccaggga acataggac tatgtggagg agtgatggat    4080
ctccgtatgc ccccatgcca agttgttccc cagagaagaa aaacacagta ctatttgatt    4140
agagtattga tccctatatt tggcttcatg tcactcatat tagtggtcta cttcttactt    4200
cttgagaaga tgaagccaag agaaaaatat atatcctcgc aatcttttgg tgagaatttc    4260
cttaaagtct catataatga tctagctcaa gccacaagaa acttctcgga ggctaacctt    4320
attggcaaag gaagctatgg tacgtgtac agaggtaagt tgaaggaatg taagttggaa    4380
gtagccgtga aggttttga ccttgagatg cgaggtgccg aaagaagctt catatcggaa    4440
tgtgaagctc tcagaagcat tcaacataga aatcttcttc caatcataac tgcatgctcg    4500
accgtggaca gtacgggcaa cgttttcaaa gctttagttt acgagtacat gcctaatggc    4560
aacttggaca cttggataca tgacaaagag ggtgggaaag ctcccggacg tttgggttta    4620
agacaaacaa ttagcatatg tgttaacata gccgatgcac tggactattt acaccatgaa    4680
tgcggaagaa caactatcca ttgtgatttg aaacccagca atatacttt agctgatgac    4740 atgaatgctc ttttgggaga ttttggcatt gcaagatttt atatcgactc ttggtcgaca    4800
tcaacaggtt cgaatagtac agtcggtgtt aagggtacca tagggtatat tcctccaggt    4860
aattaatatg gctacttctg agttcagttt cagcttttgt tatagacagc taaatagata    4920
actgtacttt ctcttcatac ctatgtagag tacgcgggag gtggtcatcc atctacttct    4980
ggggatgttt atagtttcgg gatagtgatc ctggagctta taacaggaaa aagaccgact    5040
gatcctatgt tcaaagacgg actcgacatt atcagctttg tcgagagtaa ctttccacac    5100
cagatatttc aagtgattga tgctcgactc gcagaaaagt ccatggactc caatcaaaca    5160
aatatgacac tggaaaatgc tgtccaccag tgcttgatat ctctgctaca acttgcgctt    5220
tcttgtacgc gcaaattacc aagtgatcgc atgaacatga acaaatagc caacaagatg    5280 cattcaatca agacgacata tgttggattg gaagctaaga aatatggtcc ggcatgtaat    5340
gaacaagatg catgaaaccc cacgcgttat tacaggcgac cctgagtcgc gcacaacaat    5400
tgcaacatat tgataagtgt atagtccaac aagaagaaaa tggttcttgt gtgttagaag    5460
ttaagataat taaggtgata atatgaagca ccaaagcgta ccttctaacg gtgataatat    5520
gaagattggt gattgtgact ttatgtcatg gtttatttat aacaatatat tacttcaata    5580
atgtaatagt atatgtatac gtagataatg atgttgtacc tagcatgatc ttgtattata    5640
tgcaagttga actaataaaa aaccatttct gcaggcaccc ctgctttatt ttc           5693
```

<210> SEQ ID NO 6
<211> LENGTH: 19
<212> TYPE: DNA
<213> ORGANISM: Artificial Sequence

```
<220> FEATURE:
<223> OTHER INFORMATION: Primer

<400> SEQUENCE: 6
aggtaacatg ggcctcacg                                                  19

<210> SEQ ID NO 7
<211> LENGTH: 20
<212> TYPE: DNA
<213> ORGANISM: Artificial Sequence
<220> FEATURE:
<223> OTHER INFORMATION: Primer

<400> SEQUENCE: 7
ggcaccatag acaccaagca                                                 20

<210> SEQ ID NO 8
<211> LENGTH: 28
<212> TYPE: DNA
<213> ORGANISM: Artificial Sequence
<220> FEATURE:
<223> OTHER INFORMATION: Primer

<400> SEQUENCE: 8
cgcggatccg cacgaaccag ctttgtgg                                        28

<210> SEQ ID NO 9
<211> LENGTH: 29
<212> TYPE: DNA
<213> ORGANISM: Artificial Sequence
<220> FEATURE:
<223> OTHER INFORMATION: Primer

<400> SEQUENCE: 9
cgcccatgga atcgacgttg ccaatccca                                       29

<210> SEQ ID NO 10
<211> LENGTH: 29
<212> TYPE: DNA
<213> ORGANISM: Artificial Sequence
<220> FEATURE:
<223> OTHER INFORMATION: Primer

<400> SEQUENCE: 10
ccgcggattg aatccatgag gatggtggg                                       29

<210> SEQ ID NO 11
<211> LENGTH: 25
<212> TYPE: DNA
<213> ORGANISM: Artificial Sequence
<220> FEATURE:
<223> OTHER INFORMATION: Primer

<400> SEQUENCE: 11
ccatggacgt gaggcccatg ttacc                                           25
```